United States Patent [19]

Shiokawa et al.

[11] Patent Number: 5,387,710

[45] Date of Patent: Feb. 7, 1995

[54] ETHANOLAMINE DERIVATIVES HAVING SYMPATHOMIMETIC AND ANTI-POLLAKIURIA ACTIVITIES

[75] Inventors: Youichi Shiokawa, Tsukuba; Masanobu Nagano, Kawanishi; Kiyoshi Taniguchi, Kobe; Kazuhiko Take, Tondabayashi; Takeshi Kato, Nishinomiya; Kazunori Tsubaki, Suita, all of Japan

[73] Assignee: Fujisawa Pharmaceutical Co., Ltd., Osaka, Japan

[21] Appl. No.: 117,163

[22] PCT Filed: Feb. 1, 1993

[86] PCT. No.: PCT/JP93/00113

§ 371 Date: Sep. 17, 1993

§ 102(e) Date: Sep. 17, 1993

[87] PCT Pub. No.: WO93/15041

PCT Pub. Date: Aug. 5, 1993

[30] Foreign Application Priority Data

Feb. 3, 1992 [GB] United Kingdom ............. 9202236
Aug. 24, 1992 [GB] United Kingdom ............. 9217991

[51] Int. Cl.[6] ................. C07C 229/40; A01N 33/02
[52] U.S. Cl. ............................................ 560/43
[58] Field of Search ........................ 514/647; 560/43

[56] References Cited

U.S. PATENT DOCUMENTS 4,707,497 11/1987 Cecchi et al. ................ 514/647

Primary Examiner—José G. Dees
Assistant Examiner—Joseph M. Conrad, III
Attorney, Agent, or Firm—Oblon, Spivak, McClelland, Maier & Neustadt

[57] ABSTRACT

This invention relates to new ethanolamine derivatives having gut selective sympathomimetic and anti-pollakiuria activities and represented by the general formula [I]:

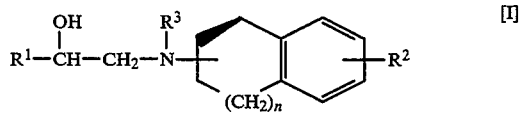

wherein $R^1$ is aryl or a heterocyclic group, each of which may be substituted with halogen, etc., $R^2$ is hydrogen, halogen, nitro, hydroxy, lower alkyl optionally substituted with acyl, lower alkenyl optionally substituted with acyl, lower alkoxy optionally substituted with acyl, or amino optionally substituted with acyl(lower)alkyl, $R^3$ is hydrogen, an N-protective group, or lower alkyl optionally substituted with lower alkylthio, n is an integer of 0 to 3, and a heavy solid line means a single bond or a double bond, provided that when n is 1, then 1) $R^1$ is a condensed aromatic hydrocarbon group or a heterocyclic group, each of which may be substituted with halogen, etc., and the like, and pharmaceutically acceptable salts thereof to processes for the preparation thereof and to a pharmaceutical composition comprising the same.

7 Claims, No Drawings

ETHANOLAMINE DERIVATIVES HAVING SYMPATHOMIMETIC AND ANTI-POLLAKIURIA ACTIVITIES

TECHNICAL FIELD

This invention relates to new ethanolamine derivatives and pharmaceutically acceptable salts thereof which are useful as a medicament.

BACKGROUND ART

Some ethanolamine derivatives having spasmolytic activity and relaxing activity on smooth muscle contraction have been known as described, for example, in European Patent Application Publication Nos. 0 211 721, 255 415 and 0 383 686.

DISCLOSURE OF INVENTION

This invention relates to new ethanolamine derivatives and pharmaceutically acceptable salts thereof.

More particularly, it relates to new ethanolamine derivatives and pharmaceutically acceptable salts thereof which have gut selective sympathomimetic and anti-pollakiuria activities, to processes for the preparation thereof, to a pharmaceutical composition comprising the same and to a method of using the same therapeutically in the treatment and/or prevention of gastrointestinal disorders caused by smooth muscle contractions in human beings or animals, and more particularly to a method for the treatment and/or prevention of spasm or hyperanakinesia in case of irritable bowel syndrome, gastritis, gastric ulcer, duodenal ulcer, enteritis, cholecystopathy, cholangitis, urinary calculus and the like; and for the treatment and/or prevention of dysuria such as pollakiuria, urinary incontinence or the like in case of nervous pollakiuria, neurogenic bladder dysfunction, nocturia, unstable bladder, cystospasm, chronic cystitis, chronic prostatitis or the like. Additionally, the object compound is expected to be useful as therapeutical and/or preventive agents for obesity and glaucoma.

One object of this invention is to provide new and useful ethanolamine derivatives and pharmaceutically acceptable salts thereof which have gut selective sympathomimetic and anti-pollakiuria activities.

Another object of this invention is to provide processes for the preparation of said ethanolamine derivatives and salts thereof.

A further object of this invention is to provide a pharmaceutical composition comprising, as an active ingredient, said ethanolamine derivatives and pharmaceutically acceptable salts thereof.

Still further object of this invention is to provide a therapeutical method for the treatment and/or prevention of aforesaid diseases in human beings or animals, using said ethanolamine derivatives and pharmaceutically acceptable salts thereof.

The object ethanolamine derivatives of this invention are new and can be represented by the following general formula [I]:

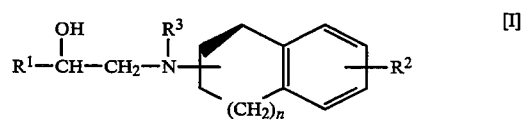

wherein $R^1$ is aryl or a heterocyclic group, each of which may be substituted with halogen, hydroxy, protected-hydroxy, aryloxy, lower alkoxy, halo(lower)alkoxy, nitro, cyano, amino or acylamino, $R^2$ is hydrogen, halogen, nitro, hydroxy, lower alkyl optionally substituted with acyl, lower alkenyl optionally substituted with acyl, lower alkoxy optionally substituted with acyl, or amino optionally substituted with acyl(lower)alkyl, $R^3$ is hydrogen, an N-protective group, or lower alkyl optionally substituted with lower alkylthio, n is an integer of 0 to 3, and a heavy solid line means a single bond or a double bond, provided that when n is 1, then 1) $R^1$ is a condensed aromatic hydrocarbon group or a heterocyclic group, each of which may be substituted with halogen, hydroxy, protected hydroxy, aryloxy, lower alkoxy, halo(lower)alkoxy, nitro, cyano, amino or acylamino, or 2) $R^2$ is halogen, nitro, lower alkyl optionally substituted with acyl, lower alkenyl optionally substituted with acyl, or amino optionally substituted with acyl(lower)alkyl, or 3) $R^3$ is an N-protective group or lower alkyl optionally substituted with lower alkylthio, or 4) a heavy solid line means a double bond, and pharmaceutically acceptable salts thereof.

The object compound [I] or its salt can be prepared by the following processes.

Process 1

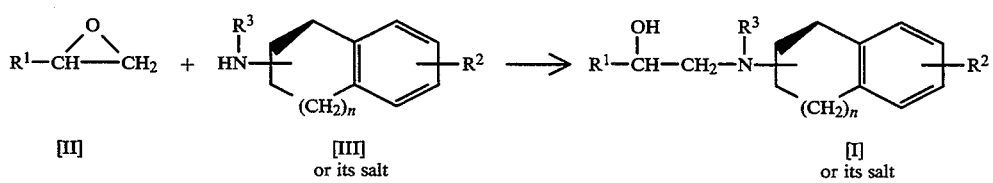

Process 2

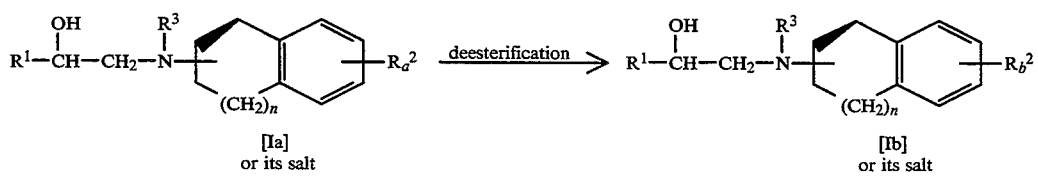

Process 3

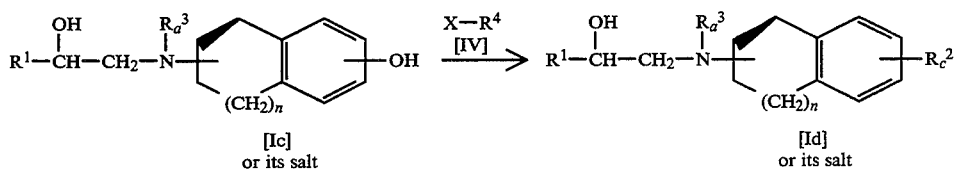

[Ic] or its salt → [Id] or its salt

Process 4

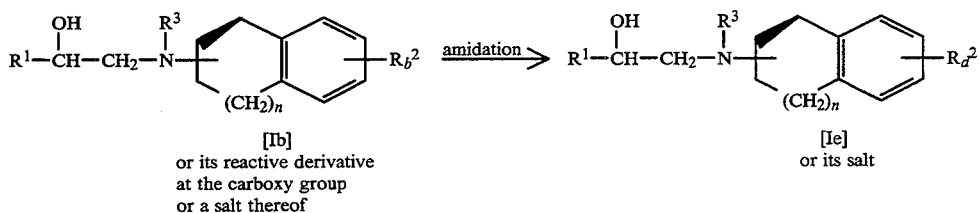

[Ib] or its reactive derivative at the carboxy group or a salt thereof → [Ie] or its salt Process 5

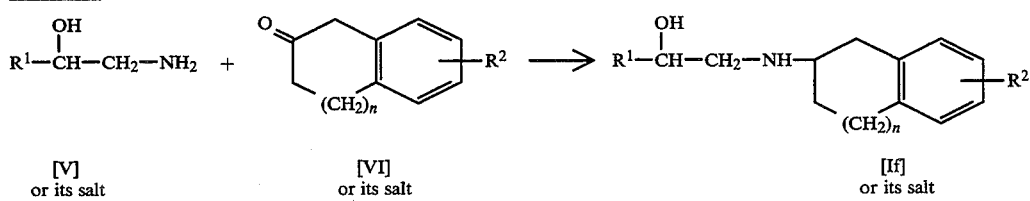

[V] or its salt + [VI] or its salt → [If] or its salt

Process 6

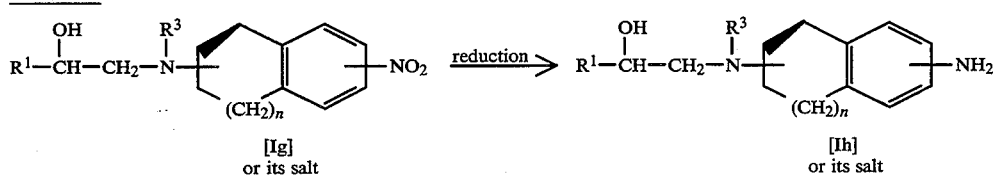

[Ig] or its salt → [Ih] or its salt

Process 7

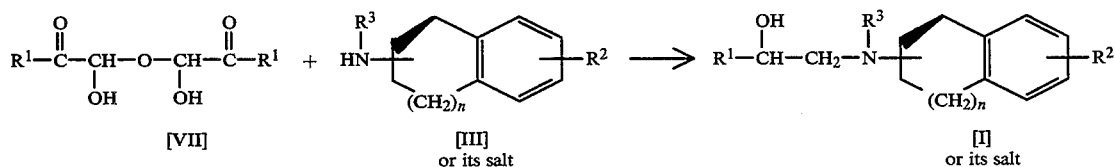

[VII] + [III] or its salt → [I] or its salt

Process 8

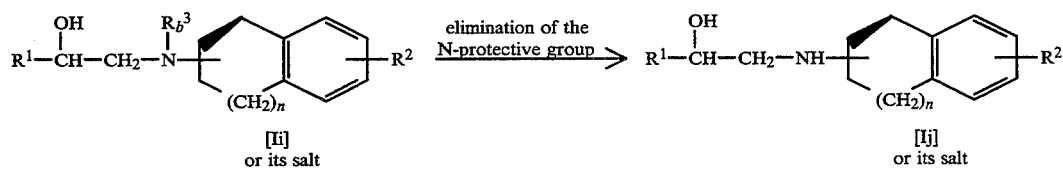

[Ii] or its salt → [Ij] or its salt wherein $R^1$, $R^2$, $R^3$, n and a heavy solid line are each as defined above, $R_a^2$ is lower alkyl substituted with esterified carboxy, lower alkenyl substituted with esterified carboxy, lower alkoxy substituted with esterified carboxy, or amino substituted with esterified carboxy(lower)alkyl, $R_b^2$ is lower alkyl substituted with carboxy, lower alkenyl substituted with carboxy, lower alkoxy substituted with carboxy, or amino substituted with carboxy(lower)alkyl, $R_a^3$ is an N-protective group or lower alkyl optionally substituted with lower alkylthio, $R_c^2$ is lower alkoxy optionally substituted with acyl, $R^4$ is lower alkyl optionally substituted with acyl, X is acid residue, $R_d^2$ is lower alkyl lower alkenyl lower alkoxy, each of which is substituted with carbamoyl optionally substituted with lower alkyl, lower alkoxy(lower)alkyl, arylsulfonyl, lower alkylsulfonyl or a heterocyclic group, or amino substituted with carbamoyl(lower)alkyl, carbamoyl in which may be substituted with lower alkyl, lower alkoxy(lower)alkyl, arylsulfonyl, lower alkylsulfonyl or a heterocyclic group, and $R_b^3$ is an N-protective group.

In the above and subsequent description of the present specification, suitable examples of the various definition to be included within the scope of the invention are explained in detail in the following.

The term "lower" is intended to mean a group having 1 to 6 carbon atom(s), unless otherwise provided.

Suitable "halogen" and halo in the term "halo(lower)alkoxy" may be fluorine, chlorine, bromine, and iodine, in which preferable one is chlorine or bromine.

Suitable "lower alkyl" and lower alkyl moiety in the terms "acyl(lower)alkyl" and "lower alkylthio" may be a straight or branched one such as methyl, ethyl, propyl, isopropyl, butyl, isobutyl, tert-butyl, pentyl, isopentyl, hexyl or the like, in which preferable one is methyl or ethyl.

Suitable "lower alkenyl" may be a straight or branched one such as ethenyl, propenyl, pentenyl, isopropenyl, butenyl, hexenyl or the like, in which preferable one is ethenyl.

Suitable "lower alkoxy" and lower alkoxy in the term "halo(lower)alkoxy" may a straight or branched one such as methoxy, ethoxy, propoxy, isopropoxy, butoxy, pentyloxy or the like, in which preferable one is methoxy, ethoxy, propoxy or pentyloxy.

Suitable "protected hydroxy" may be substituted lower alkoxy such as lower alkoxy(lower)alkoxy [e.g. methoxymethoxy, etc.], lower alkoxy(lower)alkoxy(lower)alkoxy [e.g. methoxyethoxymethoxy, etc.], substituted or unsubstituted ar(lower)alkoxy [e.g. benzyloxy, nitrobenzyloxy, etc.], etc., acyloxy such as lower alkanoyloxy [e.g. acetoxy, propionyloxy, pivaloyloxy, etc.], aroyloxy [e.g. benzoyloxy, fluorenecarbonyloxy, etc.], lower alkoxycarbonyloxy [e.g. methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy, etc.], substituted or unsubstituted ar(lower)alkoxycarbonyloxy [e.g. benzyloxycarbonyloxy, bromobenzyloxycarbonyloxy, etc.] etc., tri(lower)alkylsilyloxy [e.g. trimethylsilyloxy, etc.] and the like.

Suitable "aryl" and aryl moiety in the terms "aryloxy" and "arylsulfonyl" may be uncondensed or condensed aromatic hydrocarbon group such as phenyl, naphthyl, phenyl substituted with lower alkyl [e.g. tolyl, xylyl, mesityl, cumenyl, di(tert-butyl)phenyl, etc.], indenyl, indanyl or the like, in which preferable one is phenyl, naphthyl or indanyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 6-membered heteromonocyclic group containing 1 to 4 nitrogen atoms [e.g. pyrrolidinyl, imidazolidinyl, piperidino, piperazinyl, etc.]; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.; unsaturated 3 to 6-membered heteromonocyclic group containing an oxygen atom, for example, pyranyl, furyl, etc.; unsaturated, 3 to 6-membered heteromonocyclic group containing 1 to 2 sulfur atoms, for example, thienyl, etc.; unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.; saturated 3 to 6-membered heteromonocyclic group containing 1 to 2 oxygen atoms and 1 to 3 nitrogen atoms [e.g. morpholinyl, etc.]; unsaturated condensed heterocyclic group containing 1 to 2 oxygen atoms and 1 to 3 nitrogen atoms [e.g. benzofurazanyl, benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.; saturated 3 to 6-membered heteromonocyclic group containing 1 to 2 sulfur atoms and 1 to 3 nitrogen atoms [e.g., thiazolidinyl, etc.]; unsaturated condensed heterocyclic group containing 1 to 2 sulfur atoms and 1 to 3 nitrogen atoms [e.g., benzothiazolyl, benzothiadiazolyl, etc.]; unsaturated condensed heterocyclic group containing 1 to 2 oxygen atoms [e.g. benzofuranyl, benzodioxolyl, etc.] and the like.

Preferable one in said heterocyclic group is pyridyl, benzofurazanyl or benzodioxolyl.

Suitable "acyl" and acyl moiety in the terms "acylamino" and "acyl(lower)alkyl" may be carboxy; esterified carboxy; carbamoyl optionally substituted with lower alkyl, lower alkoxy(lower)alkyl, arylsulfonyl, lower alkylsulfonyl or a heterocyclic group; lower alkanoyl; aroyl; a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is lower alkoxycarbonyl.

The carbamoyl substituted with lower alkyl may be methylcarbamoyl, ethylcarbamoyl, propylcarbamoyl, dimethylcarbamoyl, diethylcarbamoyl, N-methyl-N-ethylcarbamoyl and the like.

The carbamoyl substituted with lower alkoxy(lower)alkyl may be methoxymethylcarbamoyl, methoxyethylcarbamoyl, ethoxymethylcarbamoyl, ethoxyethylcarbamoyl and the like, in which preferable one is methoxyethylcarbamoyl.

The carbamoyl substituted with arylsulfonyl may be phenylsulfonylcarbamoyl, tolylsulfonylcarbamoyl and the like.

The carbamoyl substituted with lower alkylsulfonyl may be methylsulfonylcarbamoyl, ethylsulfonylcarbamoyl and the like.

The carbamoyl substituted with a heterocyclic group may be one substituted with a heterocyclic group as mentioned above.

The lower alkanoyl may be substituted or unsubstituted one such as formyl, acetyl, propionyl, butyryl, isobutyryl, valeryl, isovaleryl, pivaloyl, hexanoyl, trifluoroacetyl or the like, in which preferable one is acetyl, propionyl,butyryl or pivaloyl.

The aroyl may be benzoyl, naphthoyl, toluoyl, di(-tert-butyl)benzoyl and the like.

The heterocyclic moiety in the term "a heterocycliccarbonyl" may be one mentioned above as a heterocyclic group.

Suitable "N-protective group" may be substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like, in which preferable one is benzyl.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Preferable compound [I] is one which has phenyl optionally substituted with halogen for $R^1$, lower alkoxy substituted with carboxy or esterified carboxy for $R^2$, hydrogen for $R^3$, 0, 2 or 3 for n and a single bond for a heavy solid line.

More preferable compound [I] is one which has phenyl substituted with halogen for $R^1$, methoxy substituted with esterified carboxy (more preferably lower alkoxycarbonyl) for $R^2$, hydrogen for $R^3$, 0, 2 or 3 for n, and a single bond for a heavy solid line.

Most preferable compound [I] is one which has phenyl substituted with halogen for $R^1$, methoxy substituted with lower alkoxycarbonyl for $R^2$, hydrogen for $R^3$, 2 for n, and a single bond for a heavy solid line.

Suitable pharmaceutically acceptable salts of the object compound [I] are conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartrate, methanesulfonate, benzenesulfonate, toluenesulfonate, etc.], an alkali metal salt [e.g. sodium salt, potassium salt, etc.] or the like.

The processes for preparing the object compound [I] is explained in detail in the following.

Process 1

The object compound [I] or its salt can be prepared by reacting a compound [II] with a compound [III] or its salt.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower)alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or its salt can be prepared by subjecting a compound [Ia] or its salt to deesterification reaction.

Suitable salt of the compound [Ia] may be an inorganic or organic acid addition salt as exemplified for the compound [I].

Suitable salt of the compound [Ib] may be the same as those exemplified for the compound [I].

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reaction is not critical and the reaction is usually carried out under cooling to warming.

In this reaction, in case that the compound [Ia] having an N-protective group for $R^3$ and/or a double bond for a heavy solid line is used as a starting compound, the compound [Ib] having hydrogen for $R^3$ and/or a single bond for a heavy solid line may be obtained according to reaction conditions. This case is included within the scope of the present reaction.

Process 3

The object compound [Id] or its salt can be prepared by reacting a compound [Ic] or its salt with a compound [IV].

Suitable salts of the compounds [Ic] and [Id] may be the same as those exemplified for the compound [I].

When the compound [IV] having halogen for X is used in this reaction, the reaction is preferably carried out in the presence of a base such as alkali metal [e.g. lithium, sodium, potassium, etc.], the hydroxide or carbonate or bicarbonate, thereof [e.g. sodium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like, or alkali metal iodide [e.g. sodium iodide, potassium iodide, etc.] and said base.

This reaction is usually carried out in a conventional solvent such as tetrahydrofuran, dioxane, N,N-dimethylformamide, acetone, a mixture thereof, or any other solvent which does not adversely influence the reaction. Additionally, in case that the compound [IV] is in liquid, it can also be used as a solvent.

The reaction temperature is not critical, and the reaction is usually carried out under cooling to heating.

Process 4

The object compound [Ie] or its salt can be prepared by reacting a compound [Ib] or its reactive derivative at the carboxy group or a salt thereof with an amine.

Suitable salts of the compounds [Ie] and [Ib] and its reactive derivative at the carboxy group may be the same as those exemplified for the compound [I].

Suitable amine may be ammonia, arenesulfonamide, amine substituted with a heterocyclic group.

The arenesulfonamide may be benzenesulfonamide, methylbenzenesulfonamide, ethylbenzenesulfonamide, naphthalenesulfonamide and the like, in which preferable one is methylbenzenesulfonamide.

The amine substituted with a heterocyclic group may be one substituted with a heterocyclic group as mentioned above such as aminothiazole, aminothiadiazole, aminotriazole, aminotetrazole or the like, in which preferable one is aminotetrazole.

Suitable reaction derivative at the carboxy group of the compound [Ib] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with 1,1'-carbonyl diimidazole or an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound [Ib] is used in a free acid from in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like. The reaction is also preferably carried out in the presence of a conventional base such as triethylamine, pyridine, sodium hydroxide or the like.

The reaction temperature is not critical, and the reaction can be carried out under cooling to heating.

Process 5

The object compound [If] or its salt can be prepared by reacting a compound [V] or its salt with a compound [VI] or its salt in the presence of a reducing agent.

Suitable salt of the compound [V] may be an inorganic or organic acid addition salt as exemplified for the compound [I].

Suitable salt of the compound [VI] may be the same as those exemplified for the compound [I].

Suitable reducing agent may be diborane, borane-organic amine complex [e.g. borane-pyridine complex, etc.], alkali metal cyanoborohydride [e.g. sodium cyanoborohydride, lithium cyanoborohydride, etc.] and the like.

The reaction is usually carried out in a conventional solvent such as an alcohol [e.g. methanol, ethanol, etc.], dioxane, tetrahydrofuran or any other organic solvent which does not adversely influence the reaction.

The reaction may also be carried out in an acidic condition [e.g. presence of acetic acid, etc.] and the reaction temperature is not critical, and the reaction is usually carried out under cooling to warming.

Process 6

The object compound [Ih] or its salt can be prepared by subjecting a compound [Ig] or its salt to reduction.

Suitable salts of the compounds [Ig] and [Ih] may be the same as those exemplified for the compound [I].

The present reduction is carried out by chemical reduction, catalytic reduction, or the like.

Suitable reduction agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc..], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, ethyl acetate, tetrahydrofuran, etc., or a mixture thereof.

The reaction temperature of this reduction is not critical and the reaction is usually carried out under cooling to warming.

In this reaction, in case that the compound [Ig] having an N-protective group for $R^3$ and/or a double bond for a heavy solid line is used as a starting compound, the compound [Ih] having hydrogen for $R^3$ and/or a single bond for a heavy solid line may be obtained according to reaction conditions. This case is included within the scope of the present reaction.

Process 7

The object compound [I] or its salt can be prepared by reacting a compound [VII] with a compound [III] or its salt in the presence of a reducing agent.

Suitable salts of the compounds [I] and [III] may be the same as those exemplified for the compound [I].

Suitable reducing agent may be borohydride compound such as alkali metal borohydride [e.g. sodium borohydride, sodium cyanoborohydride, lithium cyanoborohydride, lithium triethylborohydride, etc.], tetrabutylammonium cyanoborohydride or the like, in which preferable one is alkali metal borohydride.

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower)alkylamine [e.g. trimethylamine, triethylamine, etc.], picoline or the like.

The reaction is usually carried out in a conventional solvent, such as water, an alcohol [e.g. methanol, ethanol, propanol, isopropanol, etc.], dioxane, or any other organic solvent which does not adversely influence the reaction, or a mixture thereof.

The reaction temperature is not critical, and the reaction can be carried out under cooling to heating.

Process 8

The object compound [Ij] or its salt can be prepared by subjecting a compound [Ii] or its salt to elimination reaction of the N-protective group.

Suitable salts of the compounds [Ili and [Ij] may be the same as those exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

In this reaction, in case that the compound [Ii] having lower alkyl, lower alkenyl or lower alkoxy, each of which is substituted with esterified carboxy, amino substituted with esterified carboxy(lower)alkyl, or nitro for $R^2$ and/or a double bond for a heavy solid line is used as a starting compound, the compound [Ij] having lower alkyl, lower alkenyl or lower alkoxy, each of which is substituted with carboxy, amino substituted with carboxy(lower)alkyl,or amino for $R^2$ and/or a single bond for a heavy solid line may be obtained according to reaction conditions. This case is included within the scope of the present reaction.

The starting compounds [II], [IIIa], [IIIb], [IIIc], [IIId] and [VII] or a salt thereof can be prepared by the following processes.

Process A

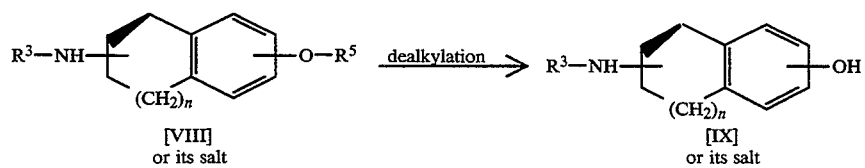

Process B

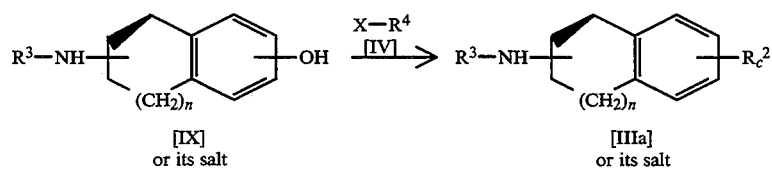

Process C

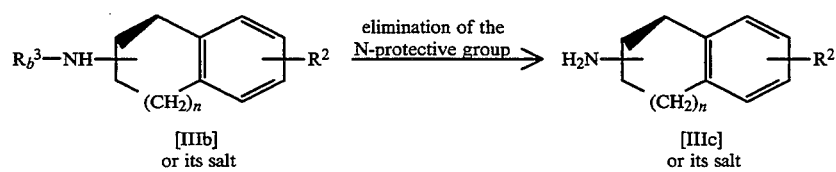

Process D

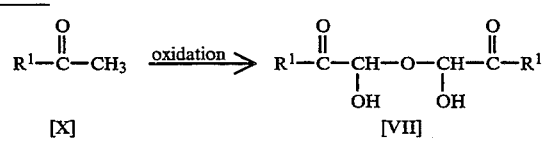

Process E

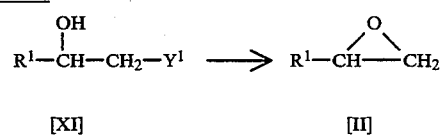

Process F

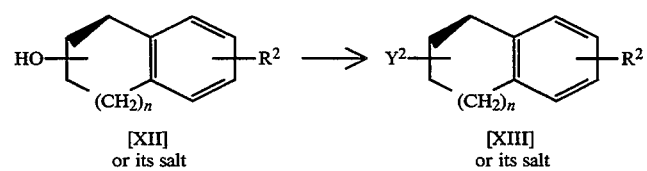

Process G

Process H

[structural reaction scheme: [IIIc] or its salt → [IIId] or its salt]

Process I

[structural reaction scheme: [XII] or its salt → [XIV] or its salt]

Process J

[structural reaction scheme: [XIV] or its salt → [IIIc] or its salt]

wherein $R^2$, $R_c^2$, $R^3$, $R_b^3$, $R^4$, X and a heavy solid line are each as defined above,
$R^5$ is lower alkyl,
$R_c^3$ is hydrogen or lower alkyl optionally substituted with lower alkylthio,
$Y^1$ is acid residue,
$Y^2$ is lower alkylsulfonyloxy or arylsulfonyloxy, and
$R_d^3$ is an N-protective group or lower alkyl optionally substituted with lower alkylthio.

The above-mentioned processes for preparing the starting compound are explained in detail in the following.

Process A

The compound [IX] or its salt can be prepared by subjecting a compound [VIII] or its salt to dealkylation reaction.

Suitable salt of the compound [VIII] may be an inorganic or organic acid addition salt as exemplified for the compound [I].

Suitable salt of the compound [IX] may be the same as those exemplified for the compound [I].

The reaction is carried out in the presence of an acid including Lewis acid [e.g. hydrochloric acid, hydrobromic acid, hydroiodic acid, boron tribromide, boron trichloride, etc.] or tri(lower alkyl)silyliodide [e.g. trimethylsilyliodide, etc.].

The reaction is usually carried out in a solvent such as water, acetic acid, methylene chloride, tetrahydrofuran, a mixture thereof or any other solvent which does not adversely influence the reaction. Additionally, in case that the above-mentioned acids are in liquid, they can also be used as a solvent.

The reaction temperature is not critical and the reaction is usually carried out under cooling to heating.

Process B

The compound [IIIa] or its salt can be prepared by reacting a compound [IX] or its salt with a compound [IV].

Suitable salt of the compound [IIIa] may be the same as those exemplified for the compound [I].

When the compound [IV] having halogen for X is used in this reaction, the reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like, or alkali metal iodide [e.g. sodium iodide, potassium iodide, etc.] or the like.

Additionally, the reaction is also preferably carried out in the presence of phase transfer catalyst [e.g. tetra-n-butylammonium bromide, etc.].

This reaction is usually carried out in a conventional solvent such as tetrahydrofuran, dioxane, aromatic hydrocarbon [e.g. benzene, toluene, xylene, etc.], N,N- dimethylformamide, acetone, a mixture thereof, or any other solvent which does not adversely influence the reaction. Additionally, in case that the compound [VI] is in liquid, it can also be used as a solvent.

The reaction temperature is not critical, and the reaction is usually carried out under cooling to heating.

Process C

The compound [IIIc] or its salt can be prepared by subjecting a compound [IIIb] or its salt to elimination reaction of the N-protective group.

Suitable salts of the compounds [IIIb] and [IIIc] may be the same as those exemplified for the compound [I].

This reaction can be carried out in substantially the same manner as Process 8, and therefore the reaction mode and the reaction condition [e.g. solvent, reaction temperature, etc.] of this reaction are to be referred to those explained in Process 8.

Process D

The compound [VII] can be prepared by subjecting a compound [X] to oxidation.

Suitable oxidizing agent to be used in this oxidation may be selenium dioxide and the like.

The reaction is usually carried out in a conventional solvent such as water, dioxane, acetic anhydride or any other organic solvent which does not adversely influence the reaction, or a mixture thereof.

The reaction temperature is not critical, and the reaction is usually carried out under heating.

Process E

The compound [II] can be prepared by reacting a compound [XI] with a base.

Suitable base may be alkali metal [e.g. lithium, sodium, potassium, etc.], the hydroxide or carbonate or bicarbonate thereof [e.g. sodium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] and the like.

The reaction is usually carried out in a conventional solvent such as water, an alcohol [e.g. methanol, ethanol, etc.], diethyl ether, tetrahydrofuran, dioxane, dimethoxyethane or any other organic solvent which does not adversely influence the reaction, or a mixture thereof.

The reaction temperature is not critical, and the reaction can be carried out under cooling to heating.

Process F

The compound [XIII] or its salt can be prepared by reacting a compound [XII] or its salt with lower alkanesulfonyl halide or arenesulfonyl halide.

Suitable salts of the compounds [XII] and [XIII] may be an inorganic acid addition salt as exemplified for the compound [I].

Suitable lower alkanesulfonyl halide may be mesyl chloride, ethanesulfonyl bromide and the like.

Suitable arenesulfonyl halide may be benzenesulfonyl chloride, tosyl chloride and the like.

The reaction is preferably carried out in the presence of a base as explained in Process 1.

The reaction is usually carried out in a conventional solvent such as water, an alcohol [e.g. methanol, ethanol, etc.], diethyl ether, tetrahydrofuran, dioxane, pyridine or any other organic solvent which does not adversely influence the reaction, or a mixture thereof.

The reaction temperature is not critical, and the reaction can be carried out under cooling to warming.

Process G

The compound [IIIc] or its salt can be prepared by the following method. Namely, 1) the compound [XIII] or its salt is firstly reacted with an azide compound, and then 2) subjecting the resultant product to catalytic reduction.

Suitable salts of the compounds [IIIc] and [XIII] may be the same as those exemplified for the compound [I].

In the first step, suitable azide compound may be alkali metal azide [e.g. sodium azide, potassium azide, etc.], alkaline earth metal azide [e.g. calcium azide, etc.], hydrogen azide and the like. The reaction is usually carried out in a conventional solvent such as tetrahydrofuran, dioxane, dimethyl sulfoxide, N,N-dimethylformamide or any other organic solvent which does not adversely influence the reaction. The reaction temperature is not critical, and the reaction is usually carried out under cooling to heating.

In the second step, this reaction can be carried out in substantially the same manner as catalytic reduction explained in Process 8, and therefore the catalyst, the reaction mode and the reaction condition [e.g. solvent, reaction temperature, etc.] of this reaction are to be referred to those as catalytic reduction explained in Process 8. The reduction may be also carried out in the presence of combination of palladium catalysts [e.g. palladium black, palladium on carbon, etc.] and formic acid or its salt [e.g. ammonium formate, etc.].

Process H

The compound [IIId] or its salt can be prepared by reacting a compound [IIIc] or its salt with an N-protective agent or lower alkylthio(lower)alkyl halide.

Suitable salts of the compound [IIIc] and [IIId] may be the same as those exemplified for the compound [I].

Suitable N-protective agent may be a halogen compound of N-protective group aforementioned such as acetyl chloride, tert-butoxycarbonyl chloride, benzyl chloride, benzyl bromide or the like.

Suitable lower alkylthio(lower)alkyl halide may be methylthiomethyl chloride, methylthioethyl chloride or the like.

The reaction is preferably carried out in the presence of a base as explained in Process 1.

The reaction is usually carried out in a conventional solvent such as water, an alcohol [e.g. methanol, ethanol, etc.], tetrahydrofuran, dioxane, pyridine or any other organic solvent which does not adversely influence the reaction, or a mixture thereof.

The reaction temperature is not critical, and the reaction can be carried out under cooling to heating.

Process I

The compound [XIV] or its salt can be prepared by reacting a compound [XII] or its salt with phthalimide in the presence of triphenylphosphine and diethyl azodicarboxylate.

Suitable salts of the compound [XII] and [XIV] may be the same as those exemplified for the compound [I].

The reaction is usually carried out in a conventional solvent such as diethyl ether, tetrahydrofuran, dioxane or any other organic solvent which does not adversely influence the reaction.

The reaction temperature is not critical, and the reaction is preferably carried out at ambient temperature or under warming to heating.

Process J

The compound [IIIc] or its salt can be prepared by reacting a compound [XIV] or its salt with hydrazine.

Suitable salts of the compounds [IIIc] and [XIV] may be an inorganic or organic acid addition salt as exemplified for the compound [I].

The reaction is usually carried out in a conventional solvent such as water, an alcohol [e.g. methanol, ethanol, etc.] or any other organic solvent which does not adversely influence the reaction, or a mixture thereof.

The reaction temperature is not critical, and the reaction can be carried out at ambient temperature or under warming to heating.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

The object compound [I] and pharmaceutically acceptable salts thereof possess gut selective sympathomimetic and anti-pollakiuria activities, and are useful for the treatment and/or prevention of gastrointestinal disorders caused by smooth muscle contractions in human beings or animals, and more particularly to methods for the treatment and/or prevention of spasm or hyperanakinesia in case of irritable bowel syndrome, gastritis, gastric ulcer, duodenal ulcer, enteritis, cholecystopathy, cholangitis, urinary calculus and the like; and for the treatment and/or prevention of dysuria such as pollakiuria, urinary incontinence or the like in case of nervous pollakiuria, neurogenic bladder dysfunction, nocturia, unstable bladder, cystospasm, chronic cystitis, chronic prostatitis or the like. Additionally, the object compound is expected to be useful as therapeutical and/or preventive agents for obesity and glaucoma.

In order to illustrate the usefulness of the object compound [I], the pharmacological data of the compound [I] are shown in the following.

Test 1

Effect on isolated rat distal colon:
(i) Test Method:

Male SD rats (180~230 g) were used. Animals were fasted for 24 hours prior to experiment. Distal colon was removed immediately after sacrifice and placed in an organ bath containing 25 ml Tyrode solution aerating with 95% $O_2$, 5% $CO_2$ at 37° C. The strip was mounted under 0.5 g tension and spontaneous contractions were recorded isometrically. After the mobility was of a uniform size, test compound was added to an organ bath and the contractions were observed over a 30 minutes period. Effect of test compound was calculated by comparing contractions before and after test compound.
(ii) Test Results:

| Test Compound (Example No.) | $IC_{50}$ (M) |
| --- | --- |
| 1 | $6.8 \times 10^{-10}$ |
| 2-3) | $8.4 \times 10^{-10}$ |
| 3-2) | $6.6 \times 10^{-10}$ |

Test 2

Effect on isolated non-pregnant rat uterus:
(i) Test Method:

Female SD rats (150~180 g) were used. 48 and 24 hours prior to use, rats were given estradiol (ovahormon benzoat: Trademark, Teikoku Hormone Mfg. Co., Ltd.) subcutaneously at a dose of 40 μg/rat to induce oestrus. The animals were killed and uterine horns were removed. Each strip was placed in an organ bath containing 25 ml Locke solution aerating with 95% $O_2$, 5% $CO_2$ at 37° C. under 1 g tension. Contractions were recorded isometrically. After the spontaneous contractions were of a uniform size, test compound was added to organ bath. The motility was observed over a 20 minutes period. Effect of test compound was calculated by comparing contractions before and after test compound.
(ii) Test Results:

| Test Compound (Example No.) | $IC_{50}$ (M) |
| --- | --- |
| 1 | $2.0 \times 10^{-7}$ |
| 2-3) | $4.4 \times 10^{-7}$ |
| 3-2) | $2.4 \times 10^{-7}$ |

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solutions, lotion, inhalant, ophthalmic preparations, suspension, emulsion, ointment, gel, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

To a mixture of 3-methoxy-6,7,8,9-tetrahydro-5H-benzocyclohepten-6-one (3.6 g), benzylamine (2.5 ml), and acetic acid (27 ml) in water bath was added portionwise sodium cyanoborohydride (0.49 g), and the mixture was stirred at ambient temperature for 5 hours. Additional benzylamine (2.5 ml) and sodium cyanoborohydride (0.10 g) were added to the mixture, and stirring was continued for an additional 2 hours. The reaction mixture was made alkaline (pH>8) with 10% sodium hydroxide (150 ml), and extracted once with ethyl acetate. The extract was washed with brine, dried over anhydrous sodium sulfate, and concentrated in vacuo. The residue was purified by column chromatography on silica gel (gradient elution; n-hexane-ethyl acetate; 3:1 to 2:1 to 1:1) to give N-benzyl-3-methoxy-6,7,8,9-tetrahydro-5H-benzocyclohepten-6-amine (4.8 g) as an oil.

IR (Film) : 3320 cm$^{-1}$

NMR (CDCl$_3$, δ): 1.3–2.2 (5H, m), 2.6–3.0 (5H, m), 3.78 (3H, s), 3.79 (1H, d, J=13 Hz), 3.89 (1H, d, J=13 Hz), 6.63 (1H, dd, J=2 Hz, 8 Hz), 6.73 (1H, d, J=2 Hz), 6.99 (1H, d, J=8 Hz), 7.2–7.4 (5H, m)

MASS (m/z): 281

Preparation 2

The following compound was obtained according to a similar manner to that of Preparation 1.

1) N-Benzyl-2-methoxy-6,7,8,9-tetrahydro-5H-benzocyclohepten-6-amine

IR (Film) : 3320 cm$^{-1}$

NMR (CDCl$_3$, δ): 1.2–2.2 (5H, m), 2.5–3.0 (5H, m), 3.77 (3H, s), 3.77 (1H, d, J=13 Hz), 3.87 (1H, d, J=13 Hz), 6.6–6.7 (2H, m), 7.0–7.1 (1H, m), 7.1–7.4 (5H, m)

MASS (m/z): 281

2) N-Benzyl-3-nitro-6,7,8,9-tetrahydro-5H-benzocyclohepten-6-amine mp: 64°–68° C.

IR (Nujol): 1520, 1335 cm$^{-1}$

NMR (CDCl$_3$, δ): 1.40–1.65 (1H, m), 1.75–2.15 (3H, m), 2.65–3.05 (5H, m), 3.80 (1H, d, J=13.1 Hz), 3.89 (1H, d, J=13.1 Hz), 7.2–7.35 (6H, m), 7.93–8.03 (2H, m)

MASS (m/z): 296

3) N-Methylthioethyl-(7-nitro-1,2,3,4-tetrahydro-2-naphthyl)amine

IR (Neat): 3300, 1510, 1340 cm$^{-1}$

NMR (CDCl$_3$, δ): 1.56–1.82 (1H, m), 2.00–2.19 (1H, m), 2.11 (3H, s), 2.60–3.20 (9H, m), 7.22 (1H, d, J=9.1 Hz), 7.89–8.02 (2H, m)

Preparation 3

A mixture of N-benzyl-3-methoxy-6,7,8,9-tetrahydro-5H-benzocyclohepten-6-amine (3.0 g) and 47% hydrobromic acid (106 ml) was stirred at 130° C. for 1.5 hours. After cooling, the reaction mixture was concentrated in vacuo. To the residue was added 28% ammonium hydroxide, and the whole was extracted once with ethyl acetate. The extract was washed twice with brine, dried over anhydrous sodium sulfate, and concentrated in vacuo. The residue was purified by column chromatography on silica gel (gradient elution; chloroform-methanol; 25:1 to 15:1) to give 8-benzylamino-6,7,8,9-tetrahydro-5H-benzocyclohepten-2-ol (1.9 g) as an oil, which solidified on standing.

mp: 87°–89° C.

IR (Nujol): 3470 cm$^{-1}$

NMR (CDCl$_3$, δ): 1.4–2.2 ( 4H, m), 2.5–3.7 (7H, m), 3.80 (2H s) 6 4–6 6 (2H, m), 6.8–7.0 (1H, m), 7.1–7.4 (5H, m)

MASS (m/z): 267

Preparation 4

The following compound was obtained according to a similar manner to that of Preparation 3.

1) 6-Benzylamino-6,7,8,9-tetrahydro-5H-benzocyclohepten-2-ol mp: 124°–125° C.

IR (Nujol): 3280 cm$^{-1}$

NMR (CDCl$_3$, δ): 1.4–2.2 (4H, m), 2.2–3.6 (7H, m), 3.78 (1H, d, J=13 Hz), 3.88 (1H, d, J=13 Hz), 6.4–6.6 (2H, m), 6.9–7.0 (1H, m), 7.2–7.4 (5H m)

MASS (m/z): 267

2) 9-Benzylamino-5,6,7,8,9,10-hexahydrobenzocycloocten-2-ol

IR (Neat): 3280, 2680, 2580, 1605 cm$^{-1}$

NMR (CDCl$_3$, δ): 1.1–1.8 (6H, m), 2.5–3.0 (5H, m), 3.87 (2H, s), 6.54 (1H, d, J=2.7 Hz), 6.61 (1H, dd, J=2.7 Hz, 8.1 Hz), 6.96 (1H, d, J=8.1 Hz), 7.15–7.5 (5H, m)

MASS (m/z): 281

Preparation 5

To an ice-cooled solution of 8-benzylamino-6,7,8,9-tetrahydro-5H-benzocyclohepten-2-ol (1.7 g) in toluene (56 ml) was added portionwise sodium hydride (60% dispersion in mineral oil; 0.31 g). After the addition was complete, the mixture was stirred at 70° C. for 1 hour. After cooling, a mixture of ethyl bromoacetate (0.81 ml) and tetra-n-butylammonium bromide (0.10 g) in toluene (14 ml) was added, and the mixture was stirred at 70° C. for 4 hours. After cooling, the reaction mixture was poured into saturated aqueous ammonium chloride, and extracted once with ethyl acetate. The extract was washed with water and brine, dried over anhydrous sodium sulfate, and concentrated in vacuo. The residue was purified by column chromatography on silica gel (gradient elution; chloroform-ethanol; 25:1 to 5:1) to give N-benzyl-3-ethoxycarbonylmethoxy-6,7,8,9-tetrahydro-5H-benzocyclohepten-6-amine (2.0 g) as an oil.

IR (Film): 3600, 3300, 1750 cm$^{-1}$

NMR (CDCl$_3$, δ): 1.29 (3H, t, J=7 Hz), 1.3–2.2 (5H, m), 2.6–3.0 (5H, m), 3.78 (1H, d, J=13 Hz), 3.88 (1H, d, J=13 Hz), 4.26 (2H, q, J=7 Hz), 4.58 (2H, s), 6.61 (1H, dd, J=2 Hz, 8 Hz), 6.76 (1H, d, J=2 Hz), 6.98 (1H, d, J=8 Hz), 7.0–7.4 (5H, m)

MASS (m/z): 353

Preparation 6

The following compound was obtained according to a similar manner to that of Preparation 5.

1) N-Benzyl-2-ethoxycarbonylmethoxy-6,7,8,9-tetrahydro-5H-benzocyclohepten-6-amine IR (Film): 3300, 1740 cm$^{-1}$ NMR (CDCl$_3$, δ): 1.29 (3H, t, J=7 Hz), 1.3–2.2 (5H, m), 2.5–3.0 (5H, m), 3.77 (1H, d, J=13 Hz), 3.87 (1H, d, J=13 Hz), 4.26 (2H, q, J=7 Hz), 4.58 (2H, s), 6.62 (1H, dd, J=2 Hz, 8 Hz), 6.69 (1H, d, J=2 Hz), 7.06 (1H, d, J=8 Hz), 7.1–7.4 (5H, m)

MASS (m/z): 353

2) N-Benzyl-2-bis(ethoxycarbonyl)methoxy-6,7,8,9-tetrahydro-5H-benzocyclohepten-6-amine IR (Film): 3220, 1740 cm$^{-1}$ NMR (CDCl$_3$, δ): 1.29 (6H, t, J=7 Hz), 1.38 (1H, br s), 1.4–1.6 (1H, m), 1.6–2.1 (3H, m), 2.5–2.9 (5H, m), 3.7–3.9 (2H, m), 4.30 (4H, q, J=7 Hz), 5.15 (1H, s), 6.66 (1H, dd, J=2 Hz, J=8 Hz), 6.75 (1H, d, J=2 Hz), 7.05 (1H, d, J=8 Hz), 7.1–7.4 (5H, m)

MASS (m/z): 426 (M+H)+

3) N-Benzyl-3-ethoxycarbonylmethoxy-5,6,7,8,9,10-hexahydrobenzocycloocten-6-amine IR (Neat): 1750, 1600 cm$^{-1}$ NMR (CDCl$_3$, δ): 1.1–2.0 (6H, m), 1.29 (3H, t, J=7.1 Hz), 2.6–3.0 (5H, m), 3.85 (1H, d, J=13.4 Hz), 3.93 (1H, d, J=13.4 Hz), 4.25 (2H, q, J=7.1 Hz), 4.57 (2H, s), 6.6–6.8 (2H, m), 6.95–7.1 (1H, m), 7.2–7.55 (5H, m)

MASS (m/z): 367

4) Ethyl 2-[8-(benzylamino)-6,7,8,9-tetrahydro-5H-benzocyclohepten-2-yloxy]propionate IR (Film): 3320, 1720, 1600 cm$^{-1}$ NMR (CDCl$_3$, δ): 1.28 (3H, t, J=7.0 Hz), 1.35-2.10 (4H, m), 1.60 (3H, d, J=6.8 Hz), 2.6-2.95 (5H, m), 3.77 (1H, d, J=13 Hz), 3.87 (1H, d, J=13 Hz), 4.20 (2H, q, J=7.0 Hz), 4.70 (1H, q, J=6.8 Hz), 6.56 (1H, dd, J=2.7 Hz, 8.2 Hz), 6.74 (1H, d, J=2.7 Hz), 6.96 (1H, d, J=8.2 Hz), 7.2-7.4 (5H, m)

Preparation 7

A mixture of N-benzyl-3-ethoxycarbonylmethoxy-6,7,8,9-tetrahydro-5H-benzocyclohepten-6-amine (1.8 g), ammonium formate (3.2 g), 10% palladium on carbon (50% wet; 0.72 g), and ethanol (50 ml) was refluxed for 0.5 hour. After cooling, the catalyst was filtered off, and rinsed with ethanol. The solvent was removed in vacuo, and the residue was purified by column chromatography on silica gel (gradient elution; chloroform-ethanol; 10:1 to 5:1) to give 3-ethoxycarbonylmethoxy-6,7,8,9-tetrahydro-H-benzocyclohepten-6-amine (1.2 g) as an oil.

IR (Film): 3360, 1750 cm$^{-1}$

NMR (CDCl$_3$, δ): 1.29 (3H, t, J=7 Hz), 1.4-2.5 (6H, m), 2.5-3.2 (5H, m), 4.26 (2H, q, J=7 Hz), 4.58 (2H, s), 6.62 (1H, dd, J=2 Hz, 8 Hz), 6.75 (1H, d, J=2 Hz), 6.98 (1H, d, J=8 Hz)

MASS (m/z): 263

Preparation 8

The following compound was obtained by reacting the compound, which was prepared according to a similar manner to that of Preparation 7, with hydrogen chloride.

2-Ethoxycarbonylmethoxy-6,7,8,9-tetrahydro-H-benzocyclohepten-6-amine hydrochloride mp: 151°-156° C.

IR (Nujol): 3100-2000, 1740 cm$^{-1}$

NMR (DMSO-d$_6$, δ): 1.0-1.5 (1H, m), 1.21 (3H, t, J=7 Hz), 1.6-2.3 (3H, m), 2.5-3.2 (5H, m), 4.16 (2H, q, J=7 Hz), 4.72 (2H, s), 6.66 (1H, dd, J=2 Hz, 8 Hz), 6.74 (1H, d, J=2 Hz), 7.04 (1H, d, J=8 Hz), 8.0-8.5 (3H, br s)

MASS (m/z): 263 (M+-HCl)

Preparation 9

The following compound was obtained by reacting the compound, which was prepared according to a similar manner to that of Preparation 1, with hydrogen chloride.

N-Benzyl-3-methoxy-5,6,7,8,9,10-hexahydrobenzocyclo-octen-6-amine hydrochloride mp: 178°-180° C.

IR (Nujol): 2640, 2575, 1600, 1580 cm$^{-1}$

NMR (DMSO-d$_6$, δ): 0.8-1.1 (1H, m), 1.3-1.55 (1H, m), 1.8-1.9 (4H, m), 2.55-2.8 (2H, m), 2.95-3.3 (3H, m), 3.72 (3H, s), 4.27 (2H, m), 6.7-6.85 (2H, m), 7.0-7.1 (1H, m), 7.35-7.65 (5H, m), 9.2-9.5 (1H, m), 9.6-9.9 (1H, m)

Preparation 10

The following compounds were obtained by reacting the compounds, which were prepared according to a similar manner to that of Preparation 5, with hydrogen chloride.

1) N-Benzyl-3-pentyloxy-6,7,8,9-tetrahydro-5H-benzocyclohepten-6-amine hydrochloride mp: 188°-193° C.

IR (Nujol): 1605, 1580 cm$^{-1}$

NMR (DMSO-d$_6$, δ): 0.9 (3H, t, J=7.0 Hz), 1.1-1.5 (5H m), 1.6-2.1 (4H, m), 2.25-2.45 (1H, m), 2.6-3.3 (5H, m), 3.91 (2H, t, J=6.4 Hz), 4.1-4.3 (2H, m), 6.68 (1H, dd, J=2.5 Hz, 8.2 Hz), 6.84 (1H, d, J=2.5 Hz), 7.01 (1H, d, J=8.2 Hz), 7.35-7.5 (3H, m), 7.6-7.7 (2H, m), 8.3-8.6 (2H, m)

2) N-Benzyl-3-(2-oxopentyloxy)-6,7,8,9-tetrahydro-5H-benzocyclohepten-6-amine hydrochloride mp: 166°-169° C.

IR (Nujol): 2425, 2375, 1715, 1610 cm$^{-1}$

NMR (DMSO-d$_6$, δ): 0.87 (3H, t, J=7.4 Hz), 1.05-1.4 (1H, m), 1.54 (2H, sextet, J=7.4 Hz), 1.8-2.1 (2H, m), 2.3-2.45 (1H, m), 2.45-2.6 (2H, m), 2.6-3.3 (5H, m), 4.26 (2H, s), 4.75 (2H, s), 6.64 (1H, dd, J=2.6 Hz, 8.3 Hz), 6.84 (1H, d, J=2.6 Hz), 7.02 (1H, d, J=8.3 Hz), 7.35-7.5 (3H, m), 7.6-7.7 (2H, m), 9.35-9.75 (2H, m)

3) N-Benzyl-3-((RS)-2-oxopentan-3-yloxy)-6,7,8,9-tetrahydro-5H-benzocyclohepten-6-amine hydrochloride mp: 162°-166° C.

IR (Nujol): 2420, 2350, 1715, 1605 cm$^{-1}$

NMR (DMSO-d$_6$, δ): 0.8-1.1 (3H, m), 1.05-1.4 (1H, m), 1.7-2.1 (4H, m), 2.14 (3H, s), 2.2-2.4 (1H, m), 2.6-3.3 (5H, m), 4.25 (2H, s), 4.65 (1H, m), 6.5-6.7 (1H, m), 6.8-6.9 (1H, m), 7.0-7.05 (1H, m), 7.4-7.65 (5H, m), 8.8-9.2 (2H, m)

MASS (m/z): 351 (M-HCl)+

4) N-Benzyl-2-ethoxycarbonylmethoxy-6,7-dihydro-5H-benzocyclohepten-7-amine hydrochloride mp: 121.5°-131° C.

IR (Nujol): 2750-2300, 1 755, 1600-1570, 1200 cm$^{-1}$

NMR (DMSO-d$_6$, δ): 1.21 (3H, t, J=7.1 Hz), 2.16 (1H, m), 2.39 (1H, m), 2.7-2.95 (2H, m), 4.02 (1H, m), 4.1-4.25 (4H, m), 4.76 (2H, s), 6.11 (1H, dd, J=11.8 Hz, 3.4 Hz), 6.67 (1H, d, J=11.8 Hz), 6.78 (1H, dd, J=8.3 Hz, 2.6 Hz), 6.89 (1H, d, J=2.6 Hz), 7.14 (1H, d, J=8.3 Hz), 7.4-7.45 (3H, m), 7.55-7.65 (2H, m), 9.7 (2H, br)

MASS (m/z): 351 (M+), 244 (base), 91

5) (S)-N-Benzyl-3-ethoxycarbonylmethoxy-6,7,8,9-tetrahydro-5H-benzocyclohepten-6-amine hydrochloride mp: 129°-130° C.

[α]$_D^{21}$ = +28.9° (c=0.34, EtOH)

IR (Nujol): 3500, 34 20, 1730 cm$^{-1}$

NMR (DMSO-d$_6$, δ): 1.1-1.4 (1H, m), 1.21 (3H, t, J=7 Hz), 1.7-2.1 (2H, m), 2.2-2.4 (1H, m), 2.6-2.8 (2H, m), 2.8-3.3 (3H, m), 4.17 (2H, q, J=7 Hz), 4.2-4.4 (2H, m), 4.72 (2H, s), 6.67 (1H, dd, J=2 Hz, 8 Hz), 6.86 (1H, d, J=2 Hz), 7.04 (1H, d, J=8 Hz), 7.3-7.5 (3H, m), 7.5-7.7 (2H, m), 9.2-9.6 (2H, br m)

MASS (m/z): 353

6) (R)-N-Benzyl-3-ethoxycarbonylmethoxy-6,7,8,9-tetrahydro-5H-benzocyclohepten-6-amine hydrochloride mp: 129°-131° C.

[α]$_D^{22}$ = -28.4° (c=0.38, EtOH)

IR (Nujol): 3550-3100, 1730 cm$^{-1}$

NMR (DMSO-d$_6$, δ): 1.1-1.4 (1H, m), 1.21 (3H, t, J=7 Hz), 1.8-2.2 (2H, m), 2.3-2.5 (1H, m), 2.6-2.8 (2H, m), 2.8-3.3 (3H, m), 4.17 (2H, q, J=7 Hz), 4.2-4.4 (2H, m), 4.72 (2H, s), 6.67 (1H, dd, J=2 Hz, 8 Hz), 6.86 (1H, d, J=2 Hz), 7.03 (1H, d, J=8 Hz), 7.4-7.5 (3H, m), 7.6-7.8 (2H, m), 9.2-9.8 (2H, br m)

MASS (m/z): 353

Preparation 11

To a mixture of 8-benzylamino-6,7,8,9-tetrahydro-5H-benzocyclohepten-2-ol (970 mg) and 1,1,1-trichloro-2-methyl-2-propanol hydrate (1.28 g) in acetone (30 ml) was added portionwise powder KOH (1.71 g)

and the mixture was stirred for 20 hours at ambient temperature. After the solvent was evaporated in vacuo, the residue was poured into 1N sodium hydroxide (30 ml) and washed with diethyl ether. The pH of the aqueous layer was adjusted to 6.0 with 3N hydrochloric acid. The precipitates were filtered off. The filtrate was concentrated in vacuo and water was added to the residue. The resulting precipitates were collected by filtration and dried to give 2-[8-benzylamino-6,7,8,9-tetrahydro-5H-benzocyclohepten-2-yloxy]-2-methylpropionic acid (0.51 g).

mp: 187°–189° C.

IR (Nujol): 3450, 1600 cm$^{-1}$

NMR (NaOD, δ): 1.2–1.45 (1H, m), 1.48 (6H, s), 1.5–2.0 (3H, m), 2.45–2.95 (5H, m), 3.65–3.9 (2H, m), 6.6–6.8 (2H, m), 6.95–7.05 (1H, m), 7.2–7.4 (5H, m)

MASS (m/z): 354 (M+1)+

Preparation 12

Thionyl chloride (0.2 ml) was added dropwise to ethanol (5 ml) with stirring at −10° C. After stirring for ten minutes, 2-(8-benzylamino-6,7,8,9-tetrahydro-5H-benzocyclohepten-2-yloxy)-2-methylpropionic acid (0.49 g) was added portionwise to the mixture. The reaction mixture was stirred at ambient temperature for 1 hour and then refluxed for 3 hours. After cooling, the mixture was poured into an aqueous solution of sodium hydrogen carbonate, and extracted with ethyl acetate. The extract was washed with water, dried over magnesium sulfate and concentrated in vacuo. The residue was purified by column chromatography on silica gel with chloroform-methanol (100:1) to give ethyl 2-(8-benzylamino-6,7,8,9-tetrahydro-5H-benzocyclohepten-2-yloxy)-2-methylpropionate (0.43 g).

IR (Neat): 1725, 1600 cm$^{-1}$

NMR (CDCl$_3$, δ): 1.25 (3H, t, J=7.1 Hz), 1.35–1.55 (1H, m), 1.57 (6H, s), 1.65–2.1 (3H, m), 2.6–2.9 (5H, m), 3.76 (1H, d, J=13 Hz), 3.87 (1H, d, J=13 Hz), 4.22 (2H, q, J=7.1 Hz), 6.55 (1H, dd, J=2.6 Hz, 8.2 Hz), 6.71 (1H, d, J=2.6 Hz), 6.92 (1H, d, J=8.2 Hz), 7.2–7.35 (5H, m)

MASS (m/z): 381

Preparation 13

To a suspension of methyltriphenylphosphonium bromide (4.2 g) in tetrahydrofuran (10 ml) was added potassium t-butoxide (1.34 g) portionwise in an ice-bath. After the addition was complete, the ice-bath was removed and the mixture was stirred at ambient temperature for 2.5 hours. 7-Methoxy-1-tetralone (1.78 g) in tetrahydrofuran (7.8 ml) was added to the mixture and stirring was continued for an additional 30 minutes. The reaction mixture was poured into ice-water, followed by the addition of n-hexane. The precipitates were filtered off and washed with n-hexane. The organic layer was separated, washed with brine, dried over anhydrous sodium sulfate, and concentrated in vacuo. The residue was triturated with n-hexane and the mixture was filtered. The filtrate was concentrated in vacuo to give 1-methylene-7-methoxy-1,2,3,4-tetrahydronaphthalene (1.69 g) as an oil.

IR (Film): 3080, 1620 (shoulder), 1600 cm$^{-1}$

NMR (DMSO-d$_6$, δ): 1.6–1.9 (2H, m), 2.4–2.6 (2H, m), 2.71 (2H, t-like, J=ca. 6 Hz), 3.74 (3H, s), 4.96 (1H, d, J=1 Hz), 5.53 (1H, d, J=1 Hz), 6.78 (1H, dd, J=2 Hz, 8 Hz), 7.03 (1H, d, J=8 Hz), 7.16 (1H, d, J=2 Hz)

MASS (m/z): 174

Preparation 14

To a solution of thallium nitrate (2.4 g) in methanol (24 ml) was added 1-methylene-7-methoxy-1,2,3,4-tetrahydronaphthalene (1.0 g) in methanol (7 ml) in one portion. The mixture was stirred for 1 minute and diluted with chloroform (24 ml). The resulting precipitate was filtered off and the filtrate was washed with saturated aqueous sodium bicarbonate and brine, dried over anhydrous magnesium sulfate, and concentrated in vacuo. The residue was purified by column chromatography on silica gel (elution; 8:1, n-hexane-ethyl acetate) to give 3-methoxy-1,2,3,4-tetrahydro-5H-benzocyclohepten-6-one (0.78 g).

mp: 50°–52° C.

IR (Film): 1700 cm$^{-1}$

NMR (CDCl$_3$, δ): 1.8–2.1 (2H, m), 2.56 (2H, t-like, J=ca. 7 Hz), 2.8–3.0 (2H, m), 3.68 (2H, s), 3.78 (3H, s), 6.7–6.8 (2H, m), 7.0–7.1 (1H, m)

MASS (m/z): 190

Preparation 15

(S)-3-Methoxy-6,7,8,9-tetrahydro-5H-benzocyclohepten-6-amine hydrochloride (35.5 g) was neutralized with cold 2N sodium hydroxide (155 ml) and the mixture was extracted once with ethyl acetate (310 ml). The extract was washed once with brine (155 ml), dried over anhydrous sodium sulfate, and concentrated in vacuo to afford (S)-3-methoxy-6,7,8,9-tetrahydro-5H-benzocyclohepten-6-amine (30.1 g). A mixture of (S)-3-methoxy-6,7,8,9-tetrahydro-5H-benzocyclohepten-6-amine (30.1 g), 10% palladium on carbon (50% wet; 5.96 g), acetic acid (0.89 ml), benzaldehyde (31.6 ml), and ethanol (300 ml) was stirred at ambient temperature for 3 hours. Then, hydrogen was introduced to the mixture and stirring was continued for an additional 1.5 hours. The catalyst was filtered off and washed with ethanol. Removal of the solvent in vacuo gave the residue, which was dissolved in ethyl acetate (423 ml). To this solution was added, with mechanically stirring in an ice-bath, 4N hydrogen chloride in ethyl acetate (77 ml). After stirring at ambient temperature for 1.5 hours, the mixture was filtered and the cake was washed with ethyl acetate (50 ml). The product was dried in vacuo to give (S)-N-benzyl-3-methoxy-6,7,8,9-tetrahydro-5H-benzocyclohepten-6-amine hydrochloride (47.3 g) as a white solid.

mp: 223°–224° C.

$[α]_D^{21} = +39.2°$ (c=0.49, EtOH)

IR (Nujol): 3050–2100, 1600, 1570 cm$^{-1}$

NMR (DMSO -d$_6$, δ): 1.1–1.4 (1H, m), 1.8–2.1 (2H, m), 2.3–2.5 (1H, m), 2.6–2.8 (2H, m), 2.8–3.0 (1H, m), 3.0–3.3 (2H, m), 3.72 (3H, s), 4.26 (2H, br s), 6.69 (1H, dd, J=2 Hz, 8 Hz), 6.84 (1H, d, J=2 Hz), 7.03 (1H, d, J=8 Hz), 7.3–7.5 (3H, m), 7.6–7.8 (2H, m), 9.3–9.8 (2H, br m)

MASS (m/z): 281

Preparation 16

The following compound was obtained according to a similar manner to that of Preparation 15.

(R)-N-Benzyl-3-methoxy-6,7,8,9-tetrahydro-5H-benzocyclohepten-6-amine hydrochloride mp: 223°–224° C.

$[α]_D^{20} = -42.7°$ (c=0.36, EtOH)

IR (Nujol): 3100–2100, 1610, 1580 cm$^{-1}$

NMR (CDCl$_3$, δ): 1.0–1.4 (2H, m), 1.8–2.1 (2H, m), 2.3–2.5 (1H, m), 2.6–2.8 (2H, m), 2.8–3.0 (1H, m), 3.0–3.3 (2H, m), 3.72 (3H, s), 4.2–4.4 (2H, m), 6.69 (1H, dd, J=2 Hz, 8 Hz), 6.84 (1H, d, J=2 Hz), 7.03 (1H, d, J=8 Hz), 7.3–7.5 (3H, m), 7.6–7.8 (2H, m), 9.4–9.8 (2H, br m)

MASS (m/z): 281

Preparation 17

1) To a suspension of (S)-N-benzyl-3-methoxy-6,7,8,9-tetrahydro-5H-benzocyclohepten-6-amine hydrochloride (46.8 g) in dichloromethane (147 ml) at −10° C. was added 1M boron tribromide in dichloromethane (294 ml) dropwise over 50 minutes during which time the temperature was allowed to rise to 10° C. After the addition was complete, the mixture was allowed to warm to ambient temperature and stirred for a total of 3 hours. The solvent was almost removed in vacuo and the residue was quenched with a mixture of water (600 ml) and ethyl acetate (450 ml) in an ice-bath. The pH of the mixture was adjusted to 8.0 with solid sodium bicarbonate (74 g) followed by the addition of 1N sodium hydroxide (60 ml). The layers were separated, and the aqueous layer was extracted once with ethyl acetate (200 ml). The combined organic layers were washed once with brine (300 ml), dried over anhydrous sodium sulfate, and concentrated in vacuo.

2) The residue was dissolved in ethyl acetate (377 ml) and treated with 4N hydrogen chloride in ethyl acetate (73 ml) in an ice-bath. After stirring at ambient temperature for 1 hour., the mixture was filtered and the cake was washed with ethyl acetate (45 ml). The product was dried in vacuo to give (S)-8-benzylamino-6,7,8,9-tetrahydro-5H-benzocyclohepten-2-ol hydrochloride (43.3 g) as a white solid.

mp: 232°–233° C.
$[\alpha]_D^{22} = +36.6°$ (c=0.42, EtOH)
IR (Nujol): 3220, 2380 cm$^{-1}$
NMR (DMSO-d$_6$, δ): 1.0–1.4 (1H, m), 1.7–2.1 (2H, m), 2.2–2.4 (1H, m), 2.5–2.7 (2H, m), 2.8–3.2 (3H, m), 4.24 (2H, br s), 6.52 (1H, dd, J=2 Hz, 8 Hz), 6.67 (1H, d, J=2 Hz), 6.89 (1H, d, J=8 Hz), 7.3–7.5 (3H, m), 7.5–7.7 (2H, m), 9.2–9.5 (2H, br m), 9.24 (1H, s)

MASS (m/z): 267

Preparation 18

The following compound was obtained according to a similar manner to that of Preparation 17-1).

(R)-8-Benzylamino-6,7,8,9-tetrahydro-5H-benzocyclohepten-2-ol

MASS (m/z): 267

Preparation 19

To a mixture of (R)-3-methoxy-6,7,8,9-tetrahydro-5H-benzocyclohepten-6-amine hydrochloride (54% ee by chiral HPLC analysis; 13.8 g), N-benzyloxycarbonyl-D-leucine (20.9 g), N-hydroxybenzotriazole (10.6 g), and N,N-dimethylformamide (276 ml) was added 1-(3-dimethylaminopropyl)-3-ethylcarbodiimide (12.2 g). After stirring for 3 hours at ambient temperature, the mixture was concentrated in vacuo. The residue was diluted with methylene chloride, and successively washed with water, 3N hydrochloric acid, saturated aqueous sodium bicarbonate and brine, dried over anhydrous sodium sulfate, and concentrated in vacuo. Recrystallization of the residue from ethyl acetate gave the crude product, which was further purified by recrystallization from ethanol to give a mixture of the diastereoisomers of (6R)-and (6S)-N-(N-benzyloxycarbonyl-D-leucyl)-3-methoxy-6,7,8,9-tetrahydro-5H-benzocyclohepten-6-amine (15.0 g).

mp: 158°–159° C.
IR (Nujol): 3300, 1680, 1640 cm$^{-1}$
NMR (CDCl$_3$, δ): 0.87 (12H, d, J=6 Hz), 1.3–1.8 (12H, m), 1.8–2.0 (4H, m), 2.6–3.1 (5H m), 3.74 (3H, s), 3.75 (3H, s), 3.9–4.3 (4H, m), 4.9–5.2 (4H, m), 5.5–5.7 (1H, m), 5.7–5.9 (1H, m), 6.6–6.75 (4H, m), 6.9–7.1 (2H, m), 7.2–7.5 (10H, m)

MASS (m/z): 438

Preparation 20

The following compound was obtained according to a similar manner to that of Preparation 19.

(6R)- and (6S)-N-(N-Benzyloxycarbonyl-L-leucyl)-3-methoxy-6,7,8,9-tetrahydro-5H-benzocyclohepten-6-amine mp: 168°–173° C.
IR (Nujol): 3280, 1685, 1635 cm$^{-1}$
NMR (CDCl$_3$, δ): 0.87 (12H, d, J=6 Hz), 13–18 (12H, m), 1.8–2.0 (4H, m), 2.6–3.1 (5H m), 3.74 (3H, m), 3.75 (3H, m), 3.9–4.3 (4H, m), 4.9–5.25 (5H, m), 5.6–5.9 (1H, m), 6.55–6.75 (4H, m), 6.9–7.1 (2H, m), 7.2–7.4 (10H, m)

Preparation 21

A mixture of (6R)- and (6S)-N-(N-benzyloxycarbonyl-D-leucyl)-3-methoxy-6,7,8,9-tetrahydro-5H-benzocyclohepten-6-amine (6R:6S=77:23; 20 g), ammonium formate (11.5 g), 10% palladium on carbon (50% wet; 4.0 g), and ethanol (450 ml) was refluxed for 0.5 hour. After cooling, the catalyst was filtered off, and washed with ethanol. The filtrate and washings were combined and concentrated in vacuo. The residue was diluted with ethyl acetate, and washed with saturated aqueous sodium bicarbonate and brine, dried over anhydrous sodium sulfate, and concentrated in vacuo to give a mixture of the diastereoisomers of (6R)- and (6S)-N-D-leucyl-3-methoxy-6,7,8,9-tetrahydro-5H-benzocyclohepten-6-amine (13.5 g). Optical resolution of the diastereoisomers was performed by recrystallization from diisopropyl ether to give the (6R)-isomer (7.0 g; 92.8% de) by HPLC analysis). A second crop of the product (1.8 g; 91.6% de) was obtained from the mother liquor after removal of the solvent followed by recrystallization from diisopropyl ether. Further product (0.61 g; 92.3% de) was obtained from the second mother liquor after column chromatography on silica gel (230–400 mesh, gradient elution; 50:1 to 25:1 chloroform-isopropanol, then isopropanol) followed by recrystallization from diisopropyl ether. Then, the above crude (6R)-isomers were combined (9.4 g) and further purified by recrystallization from diisopropyl ether to give (6R)-N-D-leucyl-3-methoxy-6,7,8,9-tetrahydro-5H-benzocyclohepten-6-amine (7.9 g; 95.2% de).

mp: 117°–118° C.
$[\alpha]_D^{27} = +5.6°$ (c=0.60, EtOH)
IR (Nujol): 3380, 3320, 1610 cm$^{-1}$
NMR (CDCl$_3$, δ): 0.8–1.0 (6H, m), 1.2–1.4 (1H, m), 1.47 (2H, br s), 1.5–1.8 (4H, m), 1.8–2.1 (2H, m), 2.7–2.8 (2H, m), 2.8–3.1 (2H, m), 3.2–3.4 (1H, m), 3.76 (3H, s), 4.0–4.2 (1H, m), 6.6–6.7 (2H, m), 6.9–7.1 (2H, m)

MASS (m/z): 304

Preparation 22

The following compound was obtained according to a similar manner to that of Preparation 21.

(6S)-N-L-Leucyl-3-methoxy-6,7,8,9-tetrahydro-5H-benzocyclohepten-6-amine
mp: 117°–118° C.
$[\alpha]_D^{27} = -5.4°$ (c=0.66, EtOH)
IR (Nujol): 3380, 3320, 1610 cm$^{-1}$
NMR (CDCl$_3$, δ): 0.8–1.0 (6H, m), 1.2–1.4 (1H, m), 1.33 (2H, br s), 1.5–1.8 (4H, m), 1.8–2.1 (2H, m), 2.7–2.8 (2H, m), 2.8–3.1 (2H, m), 3.2–3.4 (1H, m), 3.76 (3H, s), 4.0–4.2 (1H, m), 6.6–6.7 (2H, m), 6.9–7.1 (2H, m)
MASS (m/z): 304

Preparation 23

A mixture of (6R)-N-D-leucyl-3-methoxy-6,7,8,9-tetrahydro-5H-benzocyclohepten-6-amine (8.0 g) and 47% hydrobromic acid (262 ml) was stirred at 150° C. for 15.5 hours. After cooling to ambient temperature, the reaction mixture was stored in the refrigerator overnight. The precipitate formed was collected, washed with diisopropyl ether, and dried to give the hydrobromide of the desired product (2.9 g). This salt was neutralized with 28% ammonium hydroxide, and the mixture was concentrated in vacuo. The residue was diluted with saturated aqueous sodium bicarbonate, and the slurry was extracted three times with n-butanol. The combined organic layers were washed with brine, dried over anhydrous sodium sulfate, and concentrate in vacuo to give (R)-8-amino-6,7,8,9-tetrahydro-5H-benzocyclohepten-2-ol. This material was contaminated with ammonium bromide by NMR and IR analysis but could be used directly in the next reaction. Further product (3.46 g), which was also contaminated with ammonium bromide, was obtained from the mother liquor after work,up in the similar manner as described above. Physical data are shown for the hydrobromide of the product.
mp: 298°–299° C.
$[\alpha]_D^{27} = -24.6°$ (c=0 55, EtOH)
IR (Nujol): 3400, 1610, 1580 cm$^{-1}$
NMR (DMSO-d$_6$, δ): 1.1–2.2 (4H, m), 2.9–3.2 (5H, m), 6.4–6.6 (2H, m), 6.85–6.95 (1H, m), V.85 (3H, br s), 9.20 (1H, s)
MASS (m/z): 177

Preparation 24

The following compound was obtained according to a similar manner to that of Preparation 23.

(S)-8-Amino-6,7,8,9-tetrahydro-5H-benzocyclohepten-2-ol hydrobromide
mp: 297°–299° C.
$[\alpha]_D^{21} = +24.6°$ (c=0.65, EtOH)
IR (Nujol): 3400, 1610, 1580 cm$^{-1}$
NMR (DMSO-d$_6$, δ): 1.1–2.2 (4H, m), 2.5–3.2 (5H, m), 6.4–6.6 (2H, m), 6.85–6.95 (1H, m), 7.85 (3H, br s), 9.20 (1H, s)
MASS (m/z): 177

Preparation 25

A mixture of (R)-8-amino-6,7,8,9-tetrahydro-5H-benzocyclohepten-2-ol (5.8 g; contaminated with ammonium bromide), benzaldehyde (5.3 ml), acetic acid (0.15 ml), 10% palladium on carbon (50% wet; 1.1 g), and ethanol (260 ml) was stirred under hydrogen for 1 hour, and then an additional portion of benzaldehyde (5.3 ml) was added. After aging for 0.5 hour, hydrogen was introduced to the reaction mixture and stirring was continued for an additional 3 hours. To the reaction mixture was added an additional portion of acetic acid (0.15 ml), and the mixture was stirred under 1 atm of hydrogen for an additional 1 hour. The catalyst was filtered off, and washed with ethanol. Removal of the solvent in vacuo afforded the residue, which was diluted with ethyl acetate, washed with saturated aqueous sodium bicarbonate and brine, dried over anhydrous sodium sulfate, and concentrated in vacuo. The residue was purified by column chromatography on silica gel (gradient elution; chloroform, then 100:1 to 50:1 to 10:1 chloroform-methanol) to give (R)-8-benzylamino-6,7,8,9-tetrahydro-5H-benzocyclohepten-2-ol (6.6 g). Physical data are shown for the hydrochloride of the product, which was recrystallized from 3:1 diisopropyl ether-ethanol.
mp: 234°–235° C.
$[\alpha]_D^{27} = -34.5°$ (c=0.51, EtOH)
IR (Nujol): 3250, 2400 cm$^{-1}$
NMR (DMSO-d$_6$, δ): 1.0–1.4 (1H, m), 1.7–2.1 (2H, m), 2.2–2.4 (1H, m), 2.5–2.7 (2H, m), 2.8–3.2 (3H, m), 4.24 (2H, br s), 6.52 (1H, dd, J=2 Hz, J=8 Hz), 6.67 (1H, d, J=2 Hz), 6.89 (1H, d, J=8 Hz), 7.3–7.5 (3H, m), 7.5–7.7 (2H, m), 9.2–9.5 (2H, br m), 9.24 (1H, s)
MASS (m/z): 267

Preparation 26

The following compound was obtained according to a similar manner to that of Preparation 25.
(S)-8-Benzylamino-6,7,8,9-tetrahydro-5H-benzocyclohepten-2-ol hydrochloride
mp: 233°–235° C.

Preparation 27

A mixture of N-benzyl-3-nitro-6,7,8,9-tetrahydro-5H-benzocyclohepten-6-amine (2.8 g), formic acid (8 ml) and acetic anhydride (16 ml) was stirred at ambient temperature for 15 hours. The reaction mixture was poured into an aqueous solution of sodium hydrogen carbonate, and extracted twice with ethyl acetate. The extract was dried over anhydrous sodium sulfate and concentrated in vacuo to give N-benzyl-N-formyl-3-nitro-6,7,8,9-tetrahydro-5H-benzocyclohepten-6-amine (2.71 g).
mp 126°–128° C.
IR (Nujol): 1650, 1510 cm$^{-1}$
NMR (CDCl$_3$, δ): 1.20–1.50 (1H, m), 1.85–2.40 (3H, m), 2.60–2.95 (3H, m), 3.15–3.70 (2H, m), 4.36 (0.5H, d, J=15.5 Hz), 4.49 (0.5H, d, J=15 Hz), 4.52 (0.5H, d, J=15.5 Hz), 4.76 (0.5H, d, J=15 Hz ), 7.10–7.47 (6H, m), 7.65–7.78 (1H, m), 7.90–8.15 (1H, m), 8.31 (0.5H, s), 8.42 (0.5H, s)
MASS (m/z): 324

Preparation 28

N-Benzyl-3-methoxy-6,7,8,9-tetrahydro-5H-benzocyclohepten-6-amine hydrochloride (6.0 g) was neutralized with 7% ammonium hydroxide and the mixture was extracted twice with ethyl acetate. The extract was washed with brine, dried over anhydrous sodium sulfate and concentrated in vacuo to afford an oil (5.29 g). The oil was dissolved in 1-propanol (10 ml) and the solution was added to a hot solution of D-(−)-tartaric acid (3.1 g) in 1-propanol (50 ml). After cooling, precipitated crystals were filtered. The crystals were recrystallized twice with additional D-(−)-tartaric acid (the first 0.7 g, the second 68 mg) from 1-propanol to give (S)-N-benzyl-3-methoxy-6,7,8,9-tetrahydro-5H-benzocyclohepten-6-amine (D)-tartrate (1:1) (1.7 g). Enantiomeric excess (100%) was determined with two chiral columns (CHIRALCEL, OD). HPLC conditions are as follow, eluent:hexane-2-propanol (9:1); flow rate 0.6 ml/min, column temperature 25° C., detective wavelength 220 nm. The retention time was 24.6 minutes.

mp: 152°-153° C.

$[\alpha]_D^{24} = +18.6°$ (c=0.79, DMSO)

IR (Nujol): 3520, 3300, 1730, 1620 cm$^{-1}$

NMR (DMSO-d$_6$, δ): 1.1–1.4 (1H, m), 1.65–2.05 (2H, m), 2.1–2.B (1H, m), 2.55–3.15 (5H, m), 3.71 (3H, s), 3.99 (2H, s), 4.07 (1H, d, J=13.5 Hz), 4.17 (1H, d, J=13.5 Hz), 6.66 (1H, dd, J=2.7 Hz, 8.2 Hz), 6.80 (1H, d, J=2.7 Hz), 7.00 (1H, d, J=8.2 Hz), 7.3–7.6 (5H, m)

Preparation 29

A mixture of N-benzyl-3-methoxy-6,7,8,9-tetrahydro-5H-benzocyclohepten-6-amine (68.7 g), ammonium formate (68.15 g), and 10% palladium on carbon (50% wet; 6.8 g) in ethanol (1.2 l) was refluxed for 1 hour. After cooling, the catalyst was filtered off and the solvent was removed in vacuo. To the residue, water and 28% ammonium hydroxide were added and the whole was extracted with ethyl acetate. The extract was washed with water and brine, dried over anhydrous sodium sulfate and concentrated in vacuo to give 3-methoxy-6,7,8,9-tetrahydro-5H-benzocyclohepten-6-amine (35.8 g) as an oil.

NMR (CDCl$_3$, δ): 1.38–2.10 (4H, m), 1.45 (2H, br s), 2.6–3.06 (5H, m), 3.77 (3H, s), 6.64 (1H, dd, J=2.7 Hz, 8.1 Hz), 6.71 (1H, d, J=2.7 Hz), 6.98 (1H, d, J=8.1 Hz)

MASS (m/z): 191

Preparation 30

The following compound was obtained by reacting the compound, which was prepared according to a similar manner to that of Preparation 29, with hydrogen chloride.

3-Ethoxycarbonylmethoxy-5,6,7,8,9,10-hexahydrobenzo-cycloocten-6-amine hydrochloride IR (CDCl$_3$): 1760, 1600 cm$^{-1}$ NMR (DMSO-d$_6$, δ): 0.9–1.9 (6H, m), 1.21 (3H, t, J=7.1 Hz), 2.5–3.6 (5H, m), 4.17 (2H, q, J=7.1 Hz), 4.73 (2H, s), 6.7–6.9 (2H, m), 7.0–7.1 (1H, m), 8.20 (3H, br s)

MASS (m/z): 277 (M-HCl)$^+$

Preparation 31

The following compound was obtained according to a similar manner to that of Preparation 29.

2-Ethoxycarbonylmethoxy-6,7,8,9-tetrahydro-5H-benzocyclohepten-7-amine

IR (Film): 3610, 3360, 3300, 3180, 1755, 1610, 1580, 1205, 1180 cm$^{-1}$

NMR (CDCl$_3$, δ): 1.15–1.3 (2H, m), 1.30 (3H, t, J=7.1 Hz), 1.41 (2H, br s), 2.0–2.15 (2H, m), 2.65–2.75 (4H, m), 2.9–3.05 (1H, m), 4.27 (2H, quartet, J=7.1 Hz), 4.59 (2H, s), 6.62 (1H, dd, J=8.2 Hz, 2.6 Hz), 6.72 (1H, d, J=2.6 Hz), 7.01 (1H, d, J=8.2 Hz)

MASS (m/z): 263 (M$^+$), 248, 246, 161 (base)

Preparation 32

To a hot solution of D-mandelic acid (25.65 g) in ethyl acetate (300 ml) was added a solution of 3-methoxy-6,7,8,9-tetrahydro-5H-benzocyclohepten-6-amine (35.8 g) in ethyl acetate (150 ml). After cooling, precipitated crystals were filtered. The crystals were recrystallized from a mixture of ethyl acetate and ethanol (2:1) to give (R)-3-methoxy-6,7,8,9-tetrahydro-5H-benzocyclohepten-6-amine (D)-mandelate (23.4 g). Enantiomeric excess (54%) was determined with a chiral column (ULTRON ES-OVM). HPLC conditions are as follow, eluent: 0.02M phosphoric acid buffer (pH 6.5)—acetonitrile (9:1), flow rate (1.0 ml/min, column temperature 25° C., detective wavelength 220 nm. The retention time was 11.8 minutes. The two filtrates were combined and evaporated in vacuo. The residue was converted to its (L)-mandelate in a usual manner. The crystals were recrystallized from a mixture of ethyl acetate and ethanol (2:1) to give (S)-3-methoxy-6,7,8,9-tetrahydro-5H-benzocyclohepten-6-amine (L)-mandelate (17.98 g). Enantiomeric excess (70%) was determined with the same column and conditions. The retention time was 7.9 minutes.

Preparation 33

A solution of benzylamine (8.18 g) in benzene (100 ml) was added dropwise to a suspension of 8,9-dihydro-3-nitro-5H-benzocyclohepten-5-one (15.51 g) in ethanol (155 ml) at ambient temperature over 20 minutes. The resulting mixture was stirred at the same temperature for 3 hours 30 minutes, allowed to stand at the same temperature overnight, and filtered. The filtrate was evaporated in vacuo to afford 7-benzylamino-3-nitro-6,7,8,9-tetrahydro-5H-benzocyclohepten-5-one (25.41 g) as a dark brown oil.

IR (Film): 3330, 1680, 1515, 1350 cm$^{-1}$

NMR (CDCl$_3$, δ): 1.75–1.95 (2H, m), 2.1–2.3 (1H, m), 2.9–3.15 (3H, m), 3.2–3.4 (2H, m), 3.81 (1H, d, J=13.2 Hz), 3.91 (1H, d, J=13.2 Hz), 7.25–7.45 (6H, m), 8.23 (1H, dd, J=8.2 Hz, 2.4 Hz), 8.60 (1H, d, J=2.4 Hz)

Preparation 34

An aqueous solution (92 ml) of sodium borohydride (18.29 g) was added dropwise to a stirred solution of 7-benzylamino-3-nitro-6,7,8,9-tetrahydro-5H-benzocyclohepten-5-one (25.01 g) at ambient temperature over 20 minutes. The resulting mixture was stirred for 4 hours and allowed to stand overnight at the same temperature and evaporated in vacuo. The residue was diluted with water and extracted twice with dichloromethane. The combined extracts were washed with brine, dried over sodium sulfate, treated with 4N hydrogen chloride in ethyl acetate, and evaporated in vacuo. The residue was suspended in methanol and filtered. The filtrate was evaporated in vacuo, diluted with ammonia aqueous solution, and extracted twice with dichloromethane. The combined extracts were washed with brine, dried over sodium sulfate, and chromatographed over silica gel using dichloromethane-methanol. The eluate was evaporated in vacuo and the residue was washed with diethyl ether to afford 7-benzylamino-3-nitro-6,7,8,9-tetrahydro-5H-benzocyclohepten-5-ol (7.33 g) as a dark yellow powder (diastereomers mixture).

mp: 109°–120° C.

IR (Nujol): 3310, 3150, 1515, 1350 cm$^{-1}$

NMR (CDCl$_3$, δ): 1.75–2.05 (5H m), 2.3 (2H, m), 2.6–2.85 (2H, m), 3.15–3.65 (4H, m), 3.85 (2H, d, J=12.8 Hz), 4.02 (2H, d, J=12.8 Hz), 4.98 (1H, d, J=8.2 Hz), 5.32 (1H, m), 7.2–7.4 (14H, m), 8.01 (2H, dd, J=8.2 Hz, 2.2 Hz), 8.14 (1H, d, J=2.2 Hz), 8.29 (1H, d, J=2.2 Hz)

MASS (m/z): 312 (M$^+$), 221, 91 (base)

Preparation 35

A mixture of 7-benzylamino-3-nitro-6,7,8,9-tetrahydro-5H-benzocyclohepten-5-ol (6.51 g) and potassium bisulfate (13.0 g) was heated at 210° C. for 20 minutes and suspended in a mixture of dichloromethane (150 ml), water (100 ml), and 28% ammonia solution. The suspension was filtered. The dichloromethane layer was separated, dried over magnesium sulfate, evaporated in vacuo, and chromatographed over silica gel using dichloromethane-methanol as an eluent. The first eluate afforded N-benzyl-6,7-dihydro-2-nitro-5H-benzocyclohepten-7-amine (3.11 g) as a dark brown solid.

mp: 62.5°–69° C.

IR (Nujol): 3310, 1660, 1580, 1520, 1340 cm$^{-1}$

NMR (CDCl$_3$, δ): 2.0 (1H, br), 2.0–2.15 (2H, m), 2.8–2.95 (2H, m), 3.45–3.55 (1H, m), 3.89 (2H, s), 6.11 (1H, dd, J=12.2 Hz, 4.2 Hz), 6.50 (1H, dd, J=12.2 Hz, 1.6 Hz), 7.2–7.4 (6H, m), 7.97 (1H, dd, J=8.2 Hz, 2.4 Hz), 8.04 (1H, d, J=2.4 Hz)

MASS (m/z): 294 (M+), 203, 91 (base)

The second eluate afforded 6,7-dihydro-2-nitro-5H-benzocyclohepten-7-amine (95 mg) as an oil.

IR (Film): 3350, 3280, 3170, 1610, 1580, 1510, 1340 cm$^{-1}$

NMR (CDCl$_3$, δ): 1.58 (2H, br s), 1.85–2.1 (2H, m), 2.85–2.95 (2H, m), 3.71 (1H, m), 6.01 (1H, dd, J=12.2 Hz, 4.0 Hz), 6.42 (1H, dd, J=12.2 Hz, 1.6 Hz), 7.28 (1H, d, J=8.2 Hz), 7.97 (1H, dd, J=8.2 Hz, 2.4 Hz), 8.04 (1H, d, J=2.4 Hz)

MASS (m/z): 204 (M+, base)

Preparation 36

A solution of N-benzyl-6,7-dihydro-2-nitro-5H-benzocyclohepten-7-amine (3.03 g) in ethanol (19 ml) and dioxane (19 ml) was added dropwise to a stirred mixture of iron powder (3.03 g) and ammonium chloride (0.36 g), in ethanol (15 ml), dioxane (15 ml), and water (15 ml) under reflux over 20 minutes. The resulting mixture was stirred under reflux for 20 minutes and the hot reaction mixture was filtered. The filtrate was evaporated in vacuo and the residue was partitioned between ethyl acetate and sodium bicarbonate aqueous solution. The organic layer was washed with brine, dried over magnesium sulfate, evaporated in vacuo, and chromatographed over silica gel using dichloromethane and methanol to afford N$^7$-benzyl-6,7-dihydro-5H-benzocyclohepten-2,7-diamine (2.52 g) as a brown oil.

IR (Film): 3440, 3350, 3220, 1620 cm$^{-1}$

NMR (CDCl$_3$, δ): 1.57 (1H, br), 1.95–2.1 (2H, m), 2.6–2.8 (2H, m), 3.4–3.6 (3H, m), 3.85 (2H, s), 5.92 (1H, dd, J=12.0 Hz, 4.0 Hz), 6.32 (1H, dd, J=12.0 Hz, 1.8 Hz), 6.4–6.55 (2H, m), 6.92 (1H, d, J=7.8 Hz), 7.2–7.4 (5H, m)

MASS (m/z): 264 (M+), 157 (base), 91

Preparation 37

Sodium nitrite (609 mg) aqueous solution (6 ml) was added dropwise to a stirred suspension of N$^7$-benzyl-6,7-dihydro-5H-benzocycloheptene-2,7-diamine (2.22 g) in 6N sulfuric acid (22 ml) under ice cooling over 15 minutes and the resulting solution was stirred at the same temperature for 30 minutes. The solution was added dropwise to a stirred solution of sulfuric acid (3 ml) in water (15 ml) at 75° C. over 15 minutes. The resulting mixture was stirred at the same temperature for 30 minutes, cooled with ice-water bath, basified with 28% ammonia solution (15 ml), and extracted six times with dichloromethane. The combined extracts were evaporated in vacuo and chromatographed over silica gel using dichloromethane and methanol to afford 7-benzylamino-6,7-dihydro-5H-benzocyclohepten-2-ol (1.72 g) as a pale brown oil.

IR (Film): 3270, 2650, 2550, 1600, 1570 cm$^{-1}$

NMR (CDCl$_3$, δ): 1.95–2.15 (2H, m), 2.6–2.8 (2H, m), 3.30 (1H, br), 3.45–3.55 (1H, m), 3.83 (1H, d, J=13.2 Hz), 3.90 (1H, d, J=13.2 Hz), 5.92 (1H, dd, J=12.2 Hz, 4.0 Hz), 6.31 (1H, dd, J=12.2 Hz, 1.8 Hz), 6.5–6.65 (2H, m), 6.96 (1H, d, J=7.8 Hz), 7.2–7.35 (6H, m)

MASS (m/z): 265 (M+), 158 (base), 91

Preparation 38

To a solution of 6-chloro-2-pyridylaldehyde (2.0 g) in diethyl ether (20 ml), a solution of methyl magnesium bromide in diethyl ether (3M, 5.65 ml) was added at 0° C. under nitrogen atmosphere and stirred for 1.5 hours. Saturated ammonium chloride solution (30 ml) was added to the solution and the organic layer was separated. The aqueous layer was extracted with diethyl ether. The combined organic layer was washed with brine, dried over anhydrous sodium sulfate, and evaporated in vacuo. The residue was purified by distillation under reduced pressure to give 1-(6-chloro-2-pyridyl)ethanol (2.13 g).

bp: 140°–145° C./5 mmHg

IR (Neat): 3375, 1585, 1560, 1435, 1410 cm$^{-1}$

NMR (CDCl$_3$-D$_2$O: δ): 1.52 (3H, d, J=6.6 Hz), 4.87 (1H, q, J=6.6 Hz), 7.20–7.34 (2H, m), 7.66 (1H, t, J=7.8 Hz)

MASS (m/z): 156 (M+), 142, 114, 78

Preparation 39

A mixture of 1-(6-chloro-2-pyridyl)ethanol (2.13 g) and manganese dioxide (8.4 g) in chloroform (21 ml) was refluxed for 8 hours. After cooling, the mixture was filtered through celite pad and the filtrate was evaporated in vacuo. The residue was purified by distillation under reduced pressure to give 2-acetyl-6-chloropyridine (1.84 g).

bp: 105°–110° C./5 mmHg

IR (Neat): 1700, 1570, 1560 cm$^{-1}$

NMR (CDCl$_3$, δ): 2.71 (3H, s), 7.52 (1H, dd, J=1.0 Hz, 7.9 Hz), 7.81 (1H, pseudo t, J=7.8 Hz), 7.97 (1H, dd, J=1.0 Hz, 7.6 Hz)

MASS (m/z): 156 (M+)

Preparation 40

A solution of 2-acetyl-6-chloropyridine (7.48 g) in 1,4-dioxane (112 ml) was added 4N hydrogen chloride in 1,4-dioxane (12.6 ml). To the solution, sulfuryl chloride (13.51 ml) was added dropwise at 30° C. After stirring for 0.5 hour, ice water (150 ml) was added to the solution and the organic layer was separated, washed with brine, dried over anhydrous sodium sulfate, and evaporated in vacuo. The residue was purified by column chromatography on silica gel with a mixture of n-hexane and toluene (1:1) as an eluent to give chloromethyl 6-chloro-2-pyridyl ketone (7.05 g) as a powder.

mp: 61°–62° C.

IR (Nujol): 1720 cm$^{-1}$

NMR (CDCl$_3$, δ): 5.07 (2H, s), 7.57 (1H, dd, J=1.0 Hz, 7.9 Hz), 7.86 (1H, pseudo t, J=7.7 Hz), 8.03 (1H, dd, J=1.0 Hz, 7.6 Hz).

Preparation 41

A solution of chloromethyl 6-chloro-2-pyridyl ketone (8.126 g) in tetrahydrofuran (32 ml) and a solution of borane in tetrahydrofuran (1.0M, 25.7 ml) were added simultaneously to a mixture of a solution (R)-tetrahydro-3,3-diphenyl-1H,3H-pyrrolo[1,2-c][1,3,2]-oxazaborole in tetrahydrofuran (ca. 0.335M, 8.9 ml) and a solution of borane in tetrahydrofuran (1.0M, 4.3 ml) at −5° C. under nitrogen atmosphere over 0.5 hour and the whole was stirred for 3.5 hours. Methanol (10.4 ml) was added dropwise to the mixture at 0° C. and the whole was stirred at ambient temperature overnight. The mixture was evaporated in vacuo and the residue was partitioned between ethyl acetate and 1N hydrochloric acid. The organic layer was separated and the aqueous layer was extracted with ethyl acetate. The combined organic layer was washed with brine, dried over sodium sulfate, and evaporated in vacuo. The residue was purified by column chromatography on silica gel with chloroform as an eluent to give (−)-2-chloro-1-(6-chloro-2-pyridyl)ethanol (7.98 g) as an oil.

$[\alpha]_D^{32} = -16.3°$ (c=0.81, $CH_2Cl_2$)

Preparation 42

The following compound was obtained according to a similar manner to that of Preparation 41.

(−)-2-Chloro-1-(2-naphthyl)ethanol mp: 93°–94° C.

$[\alpha]D_D = -40.09°$ (c=1.07, $CH_2Cl_2$)

IR (Nujol): 3210 cm$^{-1}$

NMR (CDCl$_3$, δ): 2.80 (1H, br), 3.5–3.9 (2H, m), 5.05 (1H, dd, J=3.6 Hz, 8.5 Hz), 7.4–7.5 (3H, m), 7.8 (4H, m)

Preparation 43

A mixture of (−)-2-chloro-1-(6-chloro-2-pyridyl)ethanol (1.028 g), isopropenyl acetate (1.8 ml), and lipase PS Amano (2.06 g) in dry diisopropyl ether (31 ml) was stirred at room temperature for 2.5 days. The insoluble material was filtered off and the filtrate was evaporated in vacuo. The residue was purified by column chromatography on silica gel with chloroform as an eluent to give (−)-2-chloro-1-(6-chloro-2-pyridyl)ethanol (0.40 g).

$[\alpha]_D^{28.8} = -30.0°$ (c=0.935, $CH_2Cl_2$)

IR (Neat): 3375, 1580, 1560 cm$^{-1}$

NMR (CDCl$_3$, δ): 3.54 (1H, d, J=6.3 Hz), 3.80 (1H, dd, J=6.1 Hz, 11.1Hz), 3.91 (1H, dd, J=4.8 Hz, 11.1 Hz), 4.90–5.04 (1H, m), 7.29 (1H, d, J=7.9 Hz), 7.40 (1H, d, J=7.6 Hz), 7.71 (1H, pseudo t, J=7.7 Hz)

Preparation 44

A mixture of (−)-2-chloro-1-(6-chloro-2-pyridyl)ethanol (390 mg), 2M sodium hydroxide solution (3.9 ml), and diethyl ether (0.2 ml) was stirred at ambient temperature for 3 hours. To the mixture, brine and ethyl acetate were added. The organic layer was separated, washed with brine, dried over anhydrous sodium sulfate, and evaporated in vacuo. The residue was purified by column chromatography on silica gel with chloroform as an eluent to give (−)-1-(6-chloro-2-pyridyl)ethane-1,2-epoxide (259 mg) as an oil.

$[\alpha]_D^{30.8} = -34.4°$ (c=0.57, $CH_2Cl_2$)

IR (Neat): 1590, 1560, 1540, 1420 cm$^{-1}$

NMR (CDCl$_3$, δ): 2.88 (1H, dd, J=2.5 Hz, 5.8 Hz), 3.18 (1H, dd, J=4.1 Hz, 5.8 Hz), 3.99 (1H, dd, J=2.5 Hz, 4.1 Hz), 7.16 (1H, dd, J=0.7 Hz, 7.6 Hz), 7.27 (1H, dd, J=0.7 Hz, 7.9 Hz), 7.65 (1H, pseudo t, J=7.7 Hz)

MASS (m/z): 156 (M+)

Preparation 45

The following compound was obtained according to a similar manner to that of Preparation 44.

(+)-2-Naphthyl oxirane mp: 75°–76° C.

$[\alpha]_D = +34.17°$ (c=1.03, toluene)

IR (Nujol): 1265, 1240, 820, 740 cm$^{-1}$

NMR (CDCl$_3$, δ): 2.89 (1H, dd, J=2.6 Hz, 5.5 Hz), 3.20 (1H, dd, J=4.1 Hz, 5.5 Hz), 4.01 (1H, dd, J=2.6 Hz, 4.1 Hz), 7.31 (1H, dd, J=1.7 Hz, 8.5 Hz), 7.4–7.5 (2H, m), 7.8 (4H, m)

MASS (m/z): 170 (M+) and 141

Preparation 46

To a suspension of 3-nitro-6,7,8,9-tetrahydro-5H-benzocyclohepten-5-one (7.0 g) in methanol (70 ml), sodium borohydride (1.29 g) was added portionwise at 21°–30° C. and the whole was stirred for 1 hour. The solution was poured into ice water (210 ml) and the resulting precipitate was collected by filtration, washed with water and dried to give 3-nitro-6,7,8,9-tetrahydro-5H-benzocyclohepten-5-ol (6.81 g).

mp: 116°–118° C.

IR (Nujol): 3260, 3160, 1520, 1340 cm$^{-1}$

NMR (NMR (CDCl$_3$, δ): 1.25–2.18 (7H, m), 2.66–3.10 (2H, m), 4.89–5.06 (1H, m), 7.23 (1H, d, J=8.2 Hz), 7.99 (1H, dd, J=2.5 Hz, 8.2 Hz), 8.38 (1H, d, J=2.5 Hz)

Preparation 47

A mixture of 3-nitro-6,7,8,9-tetrahydro-5H-benzocyclohepten-5-ol (70.67 g) and potassium hydrogensulfate (53.00 g) was heated at 160° C. for 1 hour. After cooling, to the mixture was added a mixture of water (400 ml) and ethyl acetate (400 ml). The organic layer was separated and the aqueous layer was extracted with ethyl acetate (200 ml). The combined organic layer was washed with brine (150 ml), dried over anhydrous sodium sulfate, and evaporated in vacuo. The residue was purified by column chromatography on silica gel with a mixture of n-hexane and chloroform (1:1) as an eluent to give 2-nitro-6,7-dihydro-5H-benzocycloheptene (48.1 g).

mp: 43° C.

IR (Nujol): 1520, 1340, 1280, 1085, 930, 900, 835, 760, 740 cm$^{-1}$

NMR (CDCl$_3$, δ): 1.88–2.10 (2H, m), 2.40–2.59 (2H, m), 2.83–3.03 (2H, m), 6.06 (1H, dt, J=12.2 Hz, 4.5 Hz, 4.5 Hz), 6.45 (1H, dt, J=12.2 Hz, 2.0 Hz, 2.0 Hz), 7.22 (1H, d, J=8.2 Hz), 7.93 (1H, dd, J=2.4 Hz, 8.2 Hz), 8.00 (1H, d, J=2.4 Hz)

Preparation 48

A mixture of 2-nitro-6,7-dihydro-5H-benzocycloheptene (48.10 g) and m-chloroperbenzoic acid (80%, 65.75 g) in chloroform (962 ml) was refluxed for 4 hours. After cooling, 1N sodium hydroxide solution (350 ml) was added to the mixture. The organic layer was separated and the aqueous layer was extracted with chloroform. The combined organic layer was washed with brine, dried over sodium sulfate and silica gel (100 g) was added to the mixture. The insoluble material was filtered off and the filtrate was evaporated in vacuo to afford 3-nitro-6,7,8,9-tetrahydro-5H-benzocyclohepten-5,6-epoxide (53.90 g).

mp: 62°–64° C.

IR (Nujol): 1610, 1580, 1520, 1340 cm$^{-1}$

NMR (CDCl$_3$, δ): 1.43–2.32 (4H, m), 2.82–3.08 (2H, m), 3.35–3.54 (1H, m), 4.06 (1H, d, J=4.2 Hz), 7.26 (1H, d, J=8.3 Hz), 8.08 (1H, dd, J=2.4 Hz, 8.3 Hz), 8.37 (1H, d, J=2.4 Hz)

Preparation 49

A solution of 3-nitro-6,7,8,9-tetrahydro-5H-benzocyclohepten-5,6-epoxide (53.9 g) in benzene (540 ml) was added to zinc iodide (41.9 g) at ambient temperature under nitrogen atmosphere and the whole was stirred for 1 day. To the mixture, silica gel (50 g) was added and the insoluble material was filtered off. The filtrate was evaporated in vacuo. The residue was purified by column chromatography on silica gel with chloroform as an eluent to give 3-nitro-6,7,8,9-tetrahydro-5H-benzocyclohepten-6-one (33.83 g).

mp: 84°–86° C.

IR (Nujol): 1700, 1550, 1505, 1340 cm$^{-1}$

NMR (CDCl$_3$, δ): 1.95–2.17 (2H, m), 2.55–2.71 (2H, m), 3.00–3.16 (2H, m), 3.83 (2H, s), 7.34 (1H, d, J=8.0 Hz), 8.01–8.17 (2H, m)

Preparation 50

A mixture of 3-nitro-6,7,8,9-tetrahydro-5H-benzocyclohepten-6-one (0.20 g), iron powder (218 mg), ammonium chloride (52 mg), water (1.2 ml) and ethanol (4 ml) was refluxed for 2 hours. After cooling, the insoluble material was filtered off and the filtrate was evaporated in vacuo. To the residue was added ethyl acetate and water. The organic layer was separated and the aqueous layer was extracted with ethyl acetate. The combined organic layer was washed with brine, dried over anhydrous sodium sulfate, and evaporated in vacuo. The residue was purified by column chromatography on silica gel with chloroform as an eluent to give 3-amino-6,7,8,9-tetrahydro-5H-benzocyclohepten-6-one (153 mg).

IR (CHCl$_3$): 3375, 1690, 1610 cm$^{-1}$

NMR (CDCl$_3$, δ): 1.90–2.06 (2H, m), 2.48–2.66 (2H, m), 2.77–2.94 (2H, m), 3.62 (2H, s), 6.45–6.60 (2H, m), 6.93 (1H, d, J=8.6 Hz)

Preparation 51

The following compound was obtained according to a similar manner to that of Preparation 50.

N-Benzyl-N-formyl-(3-amino-6,7,8,9-tetrahydro-5H-benzocyclohepten-6-yl)amine

IR (Neat): 3680, 3450, 3390, 1660 cm$^{-1}$

Conformer A: NMR (CDCl$_3$-D$_2$O, δ): 1.14–1.46 (1H, m), 1.78–2.20 (3H, m), 2.39–2.73 (3H, m), 3.04–3.88 (2H, m), 4.36–4.78 (2H, m), 6.26–6.90 (3H, m), 7.20–7.44 (5H, m), 8.27 (1H, s)

Conformer B: NMR (CDCl$_3$-D$_2$O, δ): 1.14–1.46 (1H, m), 1.78–2.20 (3H, m), 2.39–2.73 (3H, m), 3.04–3.88 (2H, m), 4.36–4.78 (2H, m), 6.26–6.90 (3H, m), 7.20–7.44 (5H, m), 8.39 (1H, s)

Conformer A: Conformer B=1:2.3

MASS (m/z): 294 (M+), 159, 144, 131, 91

Preparation 52

To a solution of 3-amino-6,7,8,9-tetrahydro-5H-benzocyclohepten-6-one (9.42 g) in a mixture of acetic acid (1.85 ml), conc. sulfuric acid (9.24 ml) and water (24.56 ml) was added portionwise a solution of sodium nitrate (4.08 g) in water (6.00 ml) with ice salt bath cooling and the whole was stirred for 1 hour. The solution was added to a solution of cuprous bromide (10.02 g) and sodium bromide (9.40 g) in a mixture of 47% hydrobromic acid (27.72 ml) and water (61.52 ml) at 75° C. and the whole was stirred for 0.5 hour. After cooling, ice water (100 ml) and chloroform (200 ml) were added to the mixture. The insoluble material was filtered off. The organic layer was separated and the aqueous layer was extracted with chloroform. The combined organic layer was washed with brine, dried over anhydrous sodium sulfate, and treated with active carbon (0.65 g). The solution was evaporated in vacuo and the residue was purified by column chromatography on silica gel with toluene as an eluent to give 3-bromo-6,7,8,9-tetrahydro-5H-benzocyclohepten-6-one (6.34 g).

mp: 51°–59° C.

IR (Nujol): 1700 cm$^{-1}$

NMR (CDCl$_3$, δ): 1.89–2.08 (2H, m), 2.47–2.65 (2H, m), 2.83–3.00 (2H, m), 3.68 (2H, s), 7.03 (1H, d, J=7.7 Hz), 7.31 (1H, d, J=2.0 Hz), 7.33 (1H, dd, J=7.7 Hz, 2.0 Hz)

Preparation 53

A mixture of 3-bromo-6,7,8,9-tetrahydro-5H-benzocyclohepten-6-one (2.00 g), ethyl acrylate (1.26 g), palladium acetate (94 mg), tris(2-methylphenyl)phosphine (764 mg), triethylamine (1.69 g) in N,N-dimethylformamide (20 ml) was stirred at 100° C. for 20 hours under nitrogen atmosphere. After cooling, ice water (20 ml) was added to the mixture. The resulting precipitates were collected by filtration and the powder was dissolved in ethyl acetate (20 ml). The solution was washed with water (20 ml) three times, dried over anhydrous sodium sulfate and evaporated in vacuo. The residue was purified by column chromatography on silica gel with chloroform as an eluent to give ethyl (E)-3-(8-oxo-6,7,8,9-tetrahydro-5H-benzocyclohepten-2-yl)acrylate (1.34 g).

mp: 87°–88° C.

IR (Nujol): 1705, 1690 cm$^{-1}$

NMR (CDCl$_3$, δ): 1.34 (3H, t, J=7.1 Hz), 1.91–2.12 (2H, m), 2.52–2.67 (2H, m), 2.89–3.07 (2H, m), 3.74 (2H, s), 4.26 (2H, q, J=7.1 Hz), 6.40 (1H, d, J=16.0 Hz), 7.18 (1H, d, J=7.7 Hz), 7.32 (1H, d, J=1.0 Hz), 7.36 (1H, dd, J=7.7 Hz, 1.0 Hz), 7.64 (1H, d, J=16.0 Hz)

Preparation 54

A solution of ethyl (E)-3-(8-oxo-6,7,8,9-tetrahydro-5H-benzocyclohepten-2-yl)acrylate (400 mg) in ethanol (8 ml) was hydrogenated over 10% palladium on carbon (24 mg). After removing the catalyst, the solution was evaporated in vacuo and the residue was purified by column chromatography on silica gel with a mixture of n-hexane and ethyl acetate (10:1) as an eluent to give ethyl 3-(8-oxo-6,7,8,9-tetrahydro-5H-benzocyclohepten-2-yl)propionate (311 mg).

mp: 66°–68° C.

IR (Nujol): 1720, 1695 cm$^{-1}$

NMR (CDCl$_3$, δ): 1.23 (3H, t, J=7.1 Hz), 1.91–2.08 (2H, m), 2.48–2.70 (4H, m), 2.80–3.02 (4H, m), 3.70 (2H, s), 4.13 (2H, q, J=7.1 Hz), 6.96–7.06 (3H, m)

Preparation 55

A solution of N-benzyl-N-formyl-(3-amino-6,7,8,9-tetrahydro-5H-benzocyclohepten-6-yl)amine (0.80 g) in formic acid (16 ml) was refluxed for 2 hours. After cooling, the solution was evaporated in vacuo. The residue was dissolved in ethyl acetate and the solution was washed successively with 1N sodium hydroxide solution, 1N hydrochloric acid, and brine, dried over magnesium sulfate, and evaporated in vacuo. The residue was purified by column chromatography on silica gel with a mixture of chloroform and methanol (20:1) as an eluent to give N-benzyl-N-formyl-(3-formylamino-6,7,8,9-tetrahydro-5H-benzocyclohepten-6-yl)amine (0.84 g).

IR (CHCl$_3$): 3660, 3425, 3400, 1690, 1660 cm$^{-1}$

NMR (CDCl$_3$, δ): 1.16–1.49 (1H, m), 1.80–2.30 (3H, m), 2.42–2.82 (3H, m), 3.07–3.90 (3H, m), 4.28–4.86 (2H, m), 6.50–7.20 (3H, m), 7.20–7.46 (5H m), 7.66–7.93 (1H, m), 8.25–8.66 (2H, m)

MASS (m/z): 322 (M+), 187, 172, 159

Preparation 56

Sodium hydride (60% dispersion in oil, 100 mg) was washed with petroleum ether and a solution of N-benzyl-N-formyl-(3-formylamino-6,7,8,9-tetrahydro-5H-benzocyclohepten-6-yl)amine (675 mg) in tetrahydrofuran (10 ml) was added thereto with ice bath cooling. After stirring for 20 minutes, a solution of ethyl bromoacetate (0.28 ml) in tetrahydrofuran (1 ml) was added to the mixture and stirred for 1 hour. To the mixture, an aqueous saturated ammonium chloride solution was added. The organic layer was separated and washed with brine, dried over anhydrous sodium sulfate, and evaporated in vacuo. The residue was purified by column chromatography on silica gel with a mixture of chloroform and methanol (50:1) as an eluent to give ethyl N-[(8-N-benzylformylamino)-6,7,8,9-tetrahydro-5H-benzocyclohepten-2-yl]formylaminoacetate (752 mg).

IR (CHCl$_3$): 2940, 1745, 1665 cm$^{-1}$

NMR (CDCl$_3$, δ): 1.28 (3H, t, J=7.1 Hz), 1.22–1.50 (1H, m), 1.83–2.84 (6H, m), 3.09–3.76 (2H, m), 4.20 (2H, q, J=7.1 Hz), 4.28–4.86 (4H, m), 6.64–7.15 (3H, m), 7.21–7.46 (5H, m), 8.24–8.46 (2H, m)

MASS (m/z): 408 (M+), 307, 273, 245, 172

Preparation 57

A mixture of ethyl N-[(8-N-benzylformylamino)-6,7,8,9-tetrahydro-5H-benzocyclohepten-2-yl]formylaminoacetate (501 mg), 6N hydrochloric acid (6.1 ml) in ethanol (10 ml) was refluxed for 1 day. After cooling, the solution was poured into ice water (20 ml) and the pH of the solution was adjusted to 12 with sodium hydroxide solution. The solution was extracted with ethyl acetate and the extract was washed with brine, dried over anhydrous sodium sulfate, and evaporated in vacuo. The residue was purified by column chromatography on silica gel with a mixture of chloroform and ethanol (20:1) as an eluent to give ethyl [(8-benzylamino)-6,7,8,9-tetrahydro-5H-benzocyclohepten-2-yl]aminoacetate (217 mg).

IR (Neat): 3400, 1735, 1610, 1585, 1510 cm$^{-1}$

NMR (CDCl$_3$, δ): 1.29 (3H, t, J=7.1 Hz), 1.34–2.09 (5H, m), 2.52–2.95 (5H, m), 3.82 (1H, s), 3.85 (1H, s), 3.88 (2H, d, J=5.3 Hz), 4.15 (1H, t, J=5.3 Hz), 4.24 (2H, q, J=7.1Hz), 6.35 (1H, dd, J=2.5 Hz, 8.0 Hz), 6.47 (1H, d, J=2.5 Hz), 6.90 (1H, d, J=8.0 Hz), 7.17–7.36 (5H, m)

MASS (m/z): 352 (M+), 219, 207, 146

Preparation 58

A solution of (Z)-1-(3-methoxyphenyl)-2-nitroethene (33.85 g) in 1,4-dioxane (315 ml) was added dropwise to an efficiently stirred suspension of sodium borohydride (15.77 g) in a mixture of 1,4-dioxane (315 ml) and ethanol (98 ml) over a period of 0.5 hour while maintaining a temperature of 30° C. After stirring for 2 hours, the resultant slurry was diluted with ice water (393 ml) and the excess sodium borohydride was decomposed with 50% aqueous acetic acid (47.4 ml). To the solution, sodium chloride (68 g) and ethyl acetate were added. The organic layer was separated and the aqueous layer was extracted with ethyl acetate. The combined organic layer was washed with brine, dried over magnesium sulfate, and evaporated in vacuo. The residue was purified by distillation under reduced pressure to give 1-methoxy-3-(2-nitroethyl)benzene (23.62 g).

bp: 104°–107° C./1 mmHg.

IR (Neat): 1540, 1375 cm$^{-1}$

NMR (CDCl$_3$, δ): 3.29 (2H, t, J=7.4 Hz), 3.80 (3H, s), 4.60 (2H, t, J=7.4 Hz), 6.70–6.87 (3H, m), 7.19–7.33 (1H, m)

Preparation 59

To a solution of 1-methoxy-3-(2-nitroethyl)benzene (22.59 g) and tert-butyl acrylate (15.98 g) in dichloromethane (180 ml) was added a solution of 1,8-diazabicyclo[5.4.0]undec-7-ene (1.90 g) in dichloromethane (45 ml) in an ice bath. After stirring for 18.5 hours at ambient temperature, ice water (70 ml) was added to the solution. The organic layer was separated, washed successively with 1N hydrochloric acid, and brine. The solution was treated with silica gel (70 g) and evaporated in vacuo to give tert-butyl 5-(3-methoxyphenyl)-4-nitrovalerate (29.39 g).

IR (Neat): 1720, 1600, 1545 cm$^{-1}$

NMR (CDCl$_3$, δ): 1.37 (9H, s), 1.98–2.34 (4H, m), 2.94 (1H, dd, J=5.9 Hz, 14.1 Hz), 3.18 (1H, dd, J=8.5 Hz, 14.1 Hz), 3.71 (3H, s), 4.64–4.83 (1H, m), 6.61–6.75 (3H, m), 7.09–7.21 (1H, m)

MASS (m/z): 308 (M+−1)

Preparation 60

To a solution of tert-butyl 5-(3-methoxyphenyl)-4-nitrovalerate (10.00 g) in 1,4-dioxane (10 ml) was added 4N hydrogen chloride in 1,4-dioxane (17.8 ml) in an ice bath. After stirring for 3 days at ambient temperature, ice water (60 ml) and sodium chloride (6 g) was added to the solution. The pH of the solution was adjusted to 9.5 with an aqueous saturated sodium hydrogencarbonate solution and the solution was washed with ethyl acetate. After the pH of the solution was adjusted to 1 with 6N hydrochloric acid, the solution was extracted with ethyl acetate. The extract was washed with brine, dried over anhydrous sodium sulfate, treated with silica gel (20 g), and evaporated in vacuo to give 5-(3-methoxyphenyl)-4-nitrovaleric acid (8.00 g).

IR (Neat): 2950–2300, 1700, 1540 cm$^{-1}$

NMR (CDCl$_3$, δ): 2.03–2.57 (4H, m), 3.03 (1H, dd, J=6.1 Hz, 14.1 Hz), 3.28 (1H, dd, J=8.2 Hz, 14.1 Hz), 3.79 (3H, s), 4.72–4.91 (1H, m), 6.68–6.90 (3H, m), 7.17–7.31 (1H, m)

MASS (m/z): 252 (M+−1)

Preparation 61

A mixture of 5-(3-methoxyphenyl)-4-nitrovaleric acid (1.00 g) and thionyl chloride (0.34 ml) in 1,2-dichloroethane (2 ml) was refluxed for 1 hour. After cooling, aluminum chloride (0.53 g) was added to the solution at −12° C. and the whole was stirred for 0.5 hour. The solution was poured into ice water (15 ml). The organic layer was separated and the aqueous layer was extracted with dichloromethane. The combined organic layer was washed with an aqueous saturated sodium hydrogen carbonate solution, and brine, dried over anhydrous sodium sulfate, and evaporated in vacuo to give 2-methoxy-8-nitro-6,7,8,9-tetrahydro-5H-benzocyclohepten-5-one (772 mg).

mp: 120°–122° C.

IR (Nujol): 1665, 1590, 1545 cm$^{-1}$

NMR (CDCl$_3$, δ): 2.21–2.55 (2H, m), 2.65–2.84 (1H, m), 2.93–3.14 (1H, m), 3.37 (1H, dd, J=5.6 Hz, 14.6 Hz), 3.62 (1H, dd, J=7.8 Hz, 14.6 Hz), 3.87 (3H, s), 4.85–5.03 (1H, m), 6.76 (1H, d, J=2.5 Hz), 6.91 (1H, dd, J=2.5 Hz, 8.7 Hz), 7.82 (1H, d, J=8.7 Hz)

Preparation 62

To a solution of (S)-(−)-4-acetylamino-5-(3-methoxyphenyl)valeric acid (706 mg) in 1,2-dichloroethane, (2.1 ml) was added thionylchloride (0.25 ml) at 0° C. and the mixture was stirred for 3 hours. To the mixture, dichloromethane (2.1 ml) was added and then aluminum chloride.(0.72 g) was added portionwise at −10° C. After stirring for 2 hours, the solution was poured into ice water and the solution was acidified with dil. hydrochloric acid. The solution was extracted with dichloromethane. The extract was washed with saturated sodium hydrogen carbonate solution and brine, dried over anhydrous sodium sulfate, and evaporated in vacuo. The residue was crystallized from a mixture of n-hexane and ethyl acetate to give (S)-(−)-8-acetoamino-2-methoxy-6,7,8,9-tetrahydro-5H-benzocyclohepten-5-one (329 mg) as a powder.

mp: 132° C.
$[\alpha]_D^{21.1}$ = −97.2° (c=0.51, MeOH)
IR (Nujol): 3310, 1650, 1595 cm$^{-1}$
NMR (CDCl$_3$, δ): 1.38–1.60 (1H, m), 1.98 (3H, s), 2.10–2.32 (1H, m), 2.50–2.84 (2H, m), 2.90 (1H, dd, J=14.4 Hz, 5.0 Hz), 3.19 (1H, dd, J=14.4 Hz, 5.2 Hz), 3.86 (3H, s), 4.37–4.58 (1H, m), 5.53 (1H, d, J=7.5 Hz), 6.67 (1H, d, J=2.5 Hz), 6.87 (1H, dd, J=2.5 Hz, 8.6 Hz), 7.79 (1H, d, J=8.6 Hz)

Preparation 63

A solution of 2-methoxy-8-nitro-6,7,8,9-tetrahydro-5H-benzocyclohepten-5-one (0.20 g) in acetic acid (2 ml) was hydrogenated at 4 atm hydrogen atmosphere over 10% palladium on carbon (0.20 g). After removing the catalyst, the pH of the solution was adjusted to 12 with sodium hydroxide solution and the solution was extracted with ethyl acetate. The extract was washed with brine, dried over potassium carbonate, and evaporated in vacuo to give 3-methoxy-6,7,8,9-tetrahydro-5H-benzocyclohepten-6-amine (153 mg).

NMR (CDCl$_3$, δ): 1.38–2.10 (4H, m), 1.41 (2H, br s), 2.60–3.06 (5H, m), 3.77 (3H, s), 6.64 (1H, dd, J=8.1 Hz, 2.7 Hz), 6.71 (1H, d, J=2.7 Hz), 6.98 (1H, d, J=8.1 Hz)

Preparation 64

A mixture of tert-butyl 5-(3-methoxyphenyl)-4-nitrovalerate (0.31 g), 10% palladium on carbon (0.31 g), and ammonium formate (0.63 g) in methanol (3.1 ml) was stirred at ambient temperature for 0.5 hour. After the insoluble material was removed by filtration, the filtrate was evaporated in vacuo. To the residue, ethyl acetate and water were added and the organic layer was separated. The aqueous layer was extracted with ethyl acetate and the combined organic layer was washed with brine, dried over anhydrous sodium sulfate, and evaporated in vacuo to give tert-butyl 4-amino-5-(3-methoxyphenyl)valerate (245 mg).

IR (Neat): 3455, 1620, 1600, 1580 cm$^{-1}$
NMR (CDCl$_3$, δ): 1.44 (9H, s), 1.51–1.95 (2H, m), 2.05 (2H, br s), 2.21–2.47 (2H, m), 2.50 (1H, dd, J=8.6 Hz, 13.3 Hz), 2.80 (1H, dd, J=4.8 Hz, 13.3 Hz), 3.80 (3H, s), 6.65–6.86 (3H, m), 7.15–7.30 (1H, m)
MASS (m/z): 280 (M+), 224

To a solution of tert-butyl 4-amino-5-(3-methoxyphenyl)valerate (0.22 g) in 1,4-dioxane (0.2 ml), acetic anhydride (0.08 ml) was added and the solution was stirred for 80 minutes. To the solution, ethanol was added and the solution was stirred for 15 minutes. The pH of the solution was adjusted to 12 with sodium hydroxide solution and the solution was extracted with ethyl acetate. The extract was washed with brine, dried over anhydrous sodium sulfate, and evaporated in vacuo to give tert-butyl 4-acetylamino-5-(3-methoxyphenyl)valerate (246 mg).

IR (Neat): 3275, 3060 1720, 1640, 1540, 1365 cm$^{-1}$
NMR (CDCl$_3$, δ): 1.43 (9H, s), 1.52–1.90 (2H, m), 1.83 (3H, s), 2.15–2.42 (2H, m), 2.70 (1H, dd, J=7.2 Hz, 13.5 Hz), 2.85 (1H, dd, J=5.6 Hz, 13.5 Hz), 3.79 (3H, s), 4.01–4.24 (1H, m), 5.56 (1H, br d, J=8.5 Hz), 6.67–6.84 (3H, m), 7.15–7.28 (1H, m)
MASS (m/z): 322 (M+), 266, 206

Preparation 65

To a solution of tert-butyl 4-acetylamino-5-(3-methoxyphenyl)valerate (508 mg) in 1,4-dioxane (2 ml), 4N hydrogen chloride in 1,4-dioxane (4 ml) was added and the solution was stirred for 1 hour. The solution was poured into ice water (6 ml) and the pH of the solution was adjusted to 12 with sodium hydroxide solution. The solution was washed successively with diisopropyl ether and ethyl acetate and the pH of the solution was adjusted to 1 with 6N hydrochloric acid. The solution was extracted with ethyl acetate and the extract was washed with brine, dried over anhydrous sodium sulfate, and evaporated in vacuo to give 4-acetylamino-5-(3-methoxyphenyl)valeric acid (362 mg).

IR (Neat): 3300, 2950–2300, 1700 cm$^{-1}$
NMR (CDCl$_3$, δ): 1.55–1.98 (2H, m), 1.93 (3H, s), 2.30–2.47 (2H, m), 2.65–2.92 (2H, m), 3.78 (3H, s), 4.09–4.33 (1H, m), 5.88 (1H, br d, J=8.9 Hz), 6.67–6.87 (3H, m), 7.13–7.26 (1H, m), 9.42 (1H, br s)
MASS (m/z): 266 (M+ +1)

Preparation 66

A mixture of 4-acetylamino-5-(3-methoxyphenyl)valeric acid (151 mg) and (+)-cinchonine (110 mg) in 1,4-dioxane (2.6 ml) was refluxed and the solution was allowed to cool. The resulting precipitates were collected by filtration and dried to give a salt of (S)-4-acetylamino-5-(3-methoxyphenyl)valeric acid and (+)-cinchonin (117 mg). This compound was recrystallized from 1,4-dioxane to give the pure salt (61 mg).

mp: 122°–126° C.
$[\alpha]_D^{23.2}$ = +123.3° (c=1, EtOH)
IR (Nujol): 3250, 3180, 2725, 1660, 1590 cm$^{-1}$
NMR (DMSO-d$_6$, δ): 1.29–2.00 (7H, m), 1.75 (3H, s), 2.02–2.39 (3H, m), 2.41–2.84 (5H, m), 2.90–3.15 (2H, m), 3.20–4.90 (1H, br m), 3.72 (3H, s), 3.78–4.04 (1H, m), 4.99–5.20 (2H, m),.5.28–5.45 (1H, m), 5.98–6.21 (1H, m), 6.68–6.85 (3H, m), 7.10–7.26 (1H, m), 7.49–7.82 (3H, m), 7.54 (1H, d, J=4.4 Hz), 8.00 (1H, d, J=8.4 Hz), 8.25 (1H, d, J=8.4 Hz), 8.83 (1H, d, J=4.4 Hz)

Preparation 67

Salt of (S)-4-acetylamino-5-(3-methoxyphenyl)valeric acid and (+)-cinchonin (55.7 g) was suspended in ethyl acetate and the pH of the suspension was adjusted to 1 with dil. hydrochloric acid. The organic layer was separated and the aqueous layer was extracted with ethyl acetate. The combined organic layer was washed with brine, dried over magnesium sulfate, and evaporated in vacuo to give (S)-(−)-4-acetylamino-5-(3-methoxyphenyl)valeric acid (26.40 g).

mp: 66°–70° C.
$[\alpha]_D^{23.2} = -4.3°$ (c=1.06, MeOH)
IR (Nujol): 3270, 1730, 1610 cm$^{-1}$
NMR (CDCl$_3$, δ): 1.55–1.98 (2H, m), 1.92 (3H, s), 2.30–2.46 (2H, m), 2.64–2.92 (2H, m), 3.76 (3H, s), 4.08–4.30 (1H, m), 6.19 (1H, br d, J=8.8 Hz), 6.67–6.85 (3H, m), 7.13–7.26 (1H, m), 9.82 (1H, br s)

Preparation 68

To a solution of (S)-(−)-8-acetoamino-2-methoxy-6,7,8,9-tetrahydro-5H-benzocyclohepten-5-one (1.20 g) in boron trifluoride ether complex (abt. 47%, 23.9 ml), triethylsilane (3.42 ml) was added at ambient temperature and the whole was stirred for 3 days. The solution was poured into ice water and the pH of the solution was made to 9 with sodium hydroxide solution. The mixture was extracted with chloroform and the extract was washed with brine, dried over magnesium sulfate, and evaporated in vacuo. The residue was crystallized from n-hexane to give (S)-(−)-N-acetyl-3-methoxy-6,7,8,9-tetrahydro-5H-benzocyclohepten-6-amine (1.09 g).
mp: 185° C.
$[\alpha]_D^{21.2} = -45.0°$ (c=0.51, MeOH)
IR (Nujol): 3290, 1635 cm$^{-1}$
NMR (CDCl$_3$, δ): 1.43–1.80 (2H, m), 1.85–2.00 (2H, m), 1.89 (3H, s), 2.64–2.82 (2H, m), 2.84 (1H, dd, J=13.8 Hz, 7.8 Hz), 3.02 (1H, dd, J=13.8 Hz, 1.7 Hz), 3.78 (3H, s), 4.13–4.31 (1H, m), 5.26 (1H, d, J=7.7 Hz), 6.64–6.75 (2H, m), 7.02 (1H, d, J=8.9 Hz)

Preparation 69

A mixture of (S)-(−)-N-acetyl-3-methoxy-6,7,8,9-tetrahydro-5H-benzocyclohepten-6-amine (0.75 g) and potassium hydroxide (15.84 g) in a mixture of water (11.2 ml) and methanol (45 ml) was refluxed for 3 days. After cooling, the mixture was evaporated in vacuo. Water and ethyl acetate were added to the residue. The organic layer was separated and the aqueous layer was extracted with ethyl acetate. The combined organic layer was washed with brine, dried over potassium carbonate, and evaporated in vacuo. The residue was dissolved in ethyl acetate and 4N hydrogen chloride in ethyl acetate (0.71 ml) was added to the solution. The resulting precipitates were collected by filtration and dried to give (S)-(+)-3-methoxy-6,7,8,9-tetrahydro-5H-benzocyclohepten-6-amine hydrochloride (606 mg) as a colorless powder.
$[\alpha]_D^{18.0} = +30.3°$ (c=1.49, MeOH)

Preparation 70

To a solution of 7-methoxy-1-tetralone (50 g) and trimethylsulfonium iodide (69.48 g) in dimethyl sulfoxide (330 ml) was added dropwise a solution of potassium tert-butoxide (38.21 g) in dimethyl sulfoxide (165 ml) at 24° C.–28° C. The mixture was stirred for 1 hour at ambient temperature. The reaction mixture was poured into cooled water (500 ml) and extracted with ethyl acetate (500 ml). The organic layer was separated, washed with water (500 ml, three times), dried over magnesium sulfate, and evaporated in vacuo to give crude spiro[3,4-dihydro-7-methoxynaphthalene-1(2H),2'-oxirane] (48.15 g) as a pale yellow oil.
IR (Film): 1610, 800, 720 cm$^{-1}$
NMR (CDCl$_3$, δ): 1.75–1.95 (1H, m), 1.95–2.20 (3H, m), 2.80–2.95 (2H, m), 2.96 (2H, s), 3.76 (3H, s), 6.61 (1H, d, J=2.7 Hz), 6.76 (1H, dd, J=8.4 Hz, 2.7 Hz), 7.02 (1H, d, J=8.4 Hz)
MASS (m/z): 189 (M−1)

Preparation 71

To a solution of benzylamine (22.53 g) in 1-propanol (120 ml) was added dropwise a solution of spiro[3,4-dihydro-7-methoxynaphthalene-1(2H),2'-oxirane] (40.0 g) in 1-propanol (40 ml) under gentle reflux. The reaction mixture was gently refluxed for 4 hours. The solvent was removed and ethyl acetate (200 ml) was added to the residue. The ethyl acetate extract was washed with water (200 ml, four times), dried over sodium sulfate, and evaporated in vacuo. The residue was treated with 4N hydrogen chloride in ethyl acetate to give 1-benzylaminomethyl-7-methoxy-1,2,3,4-tetrahydro-1-naphthalenol hydrochloride as a white powder.
mp: 188°–189° C.
IR (Nujol): 3340, 1610, 1600, 740, 700 cm$^{-1}$
NMR (DMSO-d$_6$, δ): 1.40–1.90 (3H, m), 2.15–2.35 (1H, m), 2.55–2.70 (2H, m), 2.97 (2H, br s), 3.69 (3H, s), 4.19 (2H, br s), 5.93 (1H, br s), 6.75–6.80 (1H, m), 6.95–7.05 (2H,.m), 7.35–7.55 (3H, m), 7.60–7.70 (2H, m), 8.94 (1H, br s), 9.57 (1H, br s)
MASS (m/z): 298 (M+1)$^+$

Preparation 72

A suspension of 1-benzylaminomethyl-7-methoxy-1,2,3,4-tetrahydro-1-naphthalenol hydrochloride (45.00 g), ammonium formate (25.50 g), and 10% palladium on carbon (50% wet, 4.5 g) in methanol was refluxed for 40 minutes. After cooling, the catalyst was removed by filtration and the filtrate was evaporated in vacuo. Water (45 ml), 1N hydrochloric acid (90 ml) and diethyl ether (120 ml) were added to the residue and the aqueous layer was separated. The aqueous layer was made alkaline with 5N aqueous sodium hydroxide (45 ml), and extracted with ethyl acetate (600 ml × 6 times). The organic layers were combined, dried over sodium sulfate, and evaporated in vacuo to give 1-aminomethyl-7-methoxy-1,2,3,4-tetrahydro-1-naphthalenol (27.89 g) as a pale yellow powder.
mp: 79°–81° C.
IR (Nujol): 3360, 3300, 1610, 810, 730, 700 cm$^{-1}$
NMR (CDCl$_3$, δ): 1.60–2.20 (7H, m), 2.60–2.80 (2H, m), 2.80–3.00 (2H, m), 3.79 (3H, s), 6.75.(1H, dd, J=8.4 Hz, 2.7 Hz), 6.99 (1H, d, J=8.4 Hz), 7.06 (1H, d, J=2.7 Hz)
MASS (m/z): 2.07 (M$^+$), 178, 121

Preparation 73

To a solution of 1-aminomethyl-7-methoxy-1,2,3,4-tetrahydro-1-naphthalenol (27.50 g) in 10% aqueous acetic acid solution (250 ml) was added dropwise a solution of sodium nitrite (10.07 g) in water (61 ml) at 8° C.~9° C. The reaction mixture was stirred for 2 hours at the same temperature. The resulting precipitates were collected by filtration. The precipitates were dissolved in ethyl acetate. The solution was dried over magnesium sulfate and evaporated in vacuo. The residue was purified by column chromatography (silica gel, n-hexane:ethyl acetate:chloroform=5:1:3) to give 3-methoxy-6,7,8,9-tetrahydro-5H-benzocyclohepten-6-one (19.39 g) as a white powder.
The spectrum data of this compound coincided with that of the authentic sample.

Preparation 74

To a solution of 3-methoxy-6,7,8,9-tetrahydro-5H-benzocyclohepten-6-one (220 g) in methanol (1300 ml)

was added portionwise sodium borohydride (22.0 g) at 6° C.–30° C., and then the reaction mixture was stirred for 40 minutes and evaporated in vacuo. The residue was partitioned between ethyl acetate (1 l) and water (1 l). The organic layer was washed with 1N hydrochloric acid (500 ml), aqueous sodium hydrogen carbonate (500 ml), and brine (200 ml), and dried over magnesium sulfate. The solvent was evaporated in vacuo to give 3-methoxy-6,7,8,9-tetrahydro-5H-benzocyclohepten-6-ol as a white powder.

mp: 57°–59° C.

IR (Film): 3350, 1610, 760, 740, 700 cm$^{-1}$

NMR (CDCl$_3$, δ): 1.40–1.65 (2H, m), 1.70–1.95 (2H, m), 1.95–2.20 (1H, m), 2.65–2.75 (2H, m), 2.90–3.10 (2H, m), 3.78 (3H, s), 3.65–3.90 (1H, m), 6.66 (1H, dd, J=8.1 Hz, 2.7 Hz), 6.73 (1H, d, J=2.7 Hz), 6.98 (1H, d, J=8.1 Hz)

MASS (m/z): 192 (M+), 135

Preparation 75

A mixture of (RS)-3-methoxy-6,7,8,9-tetrahydro-5H-benzocyclohepten-6-ol (221 g), isopropenyl acetate (380 ml) and lipase PS (Amano) (221 g) in diisopropyl ether (4.8 l) was stirred at ambient temperature for 4 days. The reaction mixture was filtrated (celite) and evaporated under reduced pressure. The residue was purified by flash chromatography (silica gel, using dichloromethane and dichloromethane-methanol (20:1) successively as eluents). The first eluate gave (R)-3-methoxy-6,7,8,9-tetrahydro-5H-benzocyclohepten-6-yl acetate (138.2 g) as a pale yellow oil and the second eluate (S)-3-methoxy-6,7,8,9-tetrahydro-5H-benzocyclohepten-6-ol (104.4 g) as a colorless powder.

(R)-3-Methoxy-6,7,8,9-tetrahydro-5H-benzocyclohepten-6-yl acetate.

[α]$_D^{21}$= +16.01° (c=1.18, CH$_2$Cl$_2$)

IR (Film): 1715, 1610, 810 cm$^{-1}$

NMR (CDCl$_3$, δ): 1.35–1.65 (1H, m), 1.65–2.00 (2H, m), 2.01 (3H, s), 2.00–2.20 (1H, m), 2.65–2.80 (2H, m), 2.87 (1H, br d, J=13.6 Hz), 3.10 (1H, dd, J=13.6 Hz, 9.8 Hz), 3.77 (3H, s), 4.70–4.90 (1H, m), 6.60–6.75 (2H, m), 6.99 (1H, d, J=7.9 Hz)

MASS (m/z): 234 (M+), 174

(S)-3-Methoxy-6,7,8,9-tetrahydro-5H-benzocyclohepten-6-ol.

mp: 75°–78° C.

[α]$_D^{21}$ +16.11° (c=0.72 CH$_2$Cl$_2$)

IR (Nujol): 3350, 3270, 1610, 810, 700 cm$^{-1}$

NMR (CDCl$_3$, δ): 1.30–1.65 (2H, m), 1.65–1.95 (2H, m), 1.95–2.15 (1H, m), 2.60–2.75 (2H, m), 2.90–3.10 (2H, m), 3.70–3.90 (1H, m), 3.78 (3H, s), 6.66 (1H, dd, J=8.1 Hz, 2.7 Hz), 6.74 (1H, d, J=2.7 Hz), 7.00 (1H, d, J=8.1 Hz)

MASS (m/z): 192 (M+), 135

Preparation 76

To a solution of (R)-3-methoxy-6,7,8,9-tetrahydro-5H-benzocyclohepten-6-yl acetate (136 g) in methanol (1.36 l) was added dropwise a solution of sodium hydroxide (46.4 g) in water (232 ml) at ambient temperature. The reaction mixture was stirred for 1 hour and evaporated in vacuo. The residue was partitioned between ethyl acetate (1.1 l) and brine (550 ml). The organic layer was washed with 1N hydrochloric acid solution (550 ml), 1N aqueous sodium hydroxide solution (550 ml), and brine (550 ml), dried over magnesium sulfate, and evaporated in vacuo to give (R)-3-methoxy-6,7,8,9-tetrahydro-5H-benzocyclohepten-6-ol (108.96 g) as a white powder.

mp: 76°–78° C.

[α]$_D^{19}$= −15.16° (c=1.2, CH$_2$Cl$_2$)

IR (Nujol): 3300, 1610, 810, 760, 700 cm$^{-1}$

NMR (CDCl$_3$, δ): 1.40–1.65 (2H, m), 1.70–1.95 (2H, m), 1.95–2.20 (1H, m), 2.65–2.75 (2H, m), 2.90–3.10 (2H, m), 3.78 (3H, s), 3.65–3.90 (1H, m), 6.66 (1H, dd, J=8.1 Hz, 2.7 Hz), 6.73 (1H, d, J=2.7 Hz), 6.98 (1H, d, J=8.1 Hz)

MASS (m/z): 192 (M+), 135

Preparation 77

To a solution of (R)-3-methoxy-6,7,8,9-tetrahydro-5H-benzocyclohepten-6-ol (108.96 g) in pyridine (550 ml) was added portionwise p-toluenesulfonyl chloride (129.66 g) at 10° C.~13° C. The reaction mixture was stirred at ambient temperature for 1 day. The solvent was evaporated in vacuo and the residue was partitioned between ethyl acetate (1600 ml) and water (1080 ml). The organic layer was washed successively with 1N hydrochloric acid solution (1080 ml), aqueous sodium hydrogen carbonate (1080 ml), and brine (500 ml), dried over magnesium sulfate, and evaporated in vacuo to give a colorless powder. The colorless powder was washed with n-hexane (twice) to give (R)-3-methoxy-6,7,8,9-tetrahydro-5H-benzocyclohepten-6-yl 4-methylbenzenesulfonate (182.23 g).

mp: 88°–89° C.

[α]$_D^{20}$= +26.40° (c=2.5, CH$_2$Cl$_2$)

IR (Nujol): 1610, 1590, 1350, 1180, 760 cm$^{-1}$

NMR (CDCl$_3$, δ): 1.20–1.50 (1H, m), 1.75–2.25 (3H, m), 2.46 (3H, s), 2.55–2.70 (2H, m), 2.84 (1H, dt, J=13.8 Hz, 1.7 Hz), 3.08 (1H, dd, J=13.8 Hz, 10.1 Hz), 3.75 (3H, s), 4.40–4.55 (1H, m), 6.44 (1H, d, J=2.7 Hz), 6.65 (1H, dd, J=8.2 Hz, 2.7 Hz), 6.95 (1H, d, J=8.2 Hz), 7.30–7.40 (2H, m), 7.75–7.85 (2H, m)

MASS (m/z): 346 (M+), 174

Preparation 78

The following compounds were obtained according to a similar manner to that of Preparation 77.

1) (S)-3-Methoxy-6,7,8,9-tetrahydro-5H-benzocyclohepten-6-yl 4-methylbenzenesulfonate mp: 92°–95° C.

[α]$_D^{28}$= −30.99° (c=1.01, CH$_2$Cl$_2$)

IR (Nujol): 1610, 1600, 1580, 1350, 1180, 760, 720 cm$^{-1}$

NMR (CDCl$_3$, δ): 1.10–1.50 (1H, m), 1.75–2.20 (3H, m), 2.46 (3H, m), 2.55–2.75 (2H, m), 2.75–2.95 (1H, m), 2.95–3.15 (1H, m), 3.75 (3H, s), 4.35–4.55 (1H, m ), 6.45 (1H, d, J=2.6 Hz), 6.65 (1H, dd, J=8.2 Hz , 2.6 Hz), 6.95 (1H, d, J=8.2 Hz), 7.34 (2H, d, J=8 .1 Hz), 7.79 (2H, d, J=8.1 Hz)

MASS (m/z): 346 (M+), 174

2) 3-Methoxy-6,7,8,9-tetrahydro-5H-benzocyclohepten-6-yl 4-methylbenzenesulfonate mp: 76°–78° C.

IR (Nujol): 1600, 1350, 1170, 820, 750 cm$^{-1}$

NMR (CDCl$_3$, δ): 1.15–1.50 (1H, m), 1.75–2.20 (3H, m), 2.46 (3H, s), 2.60–2.70 (2H, m), 2.80–2.90 (1H, m), 3.00–3.15 (1H, m), 3.76 (3H, s), 4.35–4.55 (1H, m), 6.45 (1H, d, J=2.7 Hz), 6.65 (1H, dd, J=8.2 Hz, 2.7 Hz), 6.95 (1H, d, J=8.2 Hz), 7.34 (2H, d, J=8.1 Hz), 7.79 (2H, d, J=8.1 Hz)

MASS (m/z): 346 (M+), 174

3) 3-Methoxy-6,7,8,9-tetrahydro-5H-benzocyclohepten-6-yl methanesulfonate mp: 96°–97° C.

IR (Nujol): 1610, 1340, 1200, 770, 740, 720 cm$^{-1}$

NMR (CDCl$_3$, δ): 1.35–1.70 (1H, m), 1.75–2.15 (2H, m), 2.15–2.40 (1H, m), 2.70–2.75 (2H, m), 3.00 (3H, s), 3.10–3.30 (2H, m), 3.78 (3H, s), 4.65–4.85 (1H, m), 6.65–6.80 (2H, m), 7.00 (1H, d, J=8.1 Hz)

MASS (m/z): 270 (M+), 159

Preparation 79

To a solution of (R)-3-methoxy-6,7,8,9-tetrahydro-5H-benzocyclohepten-6-yl 4-methylbenzenesulfonate (181.0 g) in dimethyl sulfoxide (2170 ml) was added portionwise sodium azide (67.93 g) at ambient temperature. The mixture was stirred at 40° C. for 2 days. The reaction mixture was poured into ethyl acetate (2.2 l) and ice water (2.2 l). The organic layer was separated, washed successively with aqueous sodium hydrogen carbonate (1.1 l), water (1.1 l, three times), and brine (550 ml), dried over magnesium sulfate, treated with activated carbon, and evaporated in vacuo. The residue (117 g) was purified by column chromatography (silica gel 350 g, n-hexane:ethyl acetate=10:1) to give crude azido-form (IR (film), 2100 cm$^{-1}$ (—N$_3$)). A mixture of this azido-form (111.2 g), ammonium formate (96.82 g), and 10% palladium on carbon (50% wet, 7.78 g) in methanol was refluxed for 1 hour. After cooling, the catalyst was filtered off, and the filtrate was evaporated in vacuo. The residue was partitioned between ethyl acetate (1 l) and 2N aqueous sodium hydroxide solution (1.5 l). The organic layer was separated, washed with water (1 l) and brine (500 ml), dried over potassium carbonate, and evaporated in vacuo. The residue was treated with 4N hydrogen chloride in ethyl acetate under ice bath cooling to give (S)-3-methoxy-6,7,8,9-tetrahydro-5H-benzocyclohepten-6-amine hydrochloride (86.8 g) as a colorless powder.

mp: 258°–261° C.

[α]$_D^{20}$= +30.59° (c=1.50, MeOH)

IR (Nujol): 2610, 2500, 1610, 830, 760, 720 cm$^{-1}$

NMR (DMSO-d$_6$, δ): 1.15–1.25 (1H, m), 1.65–2.05 (2H, m), 2.05–2.25 (1H, m), 2.60–2.75 (2H, m), 2.85–3.10 (3H, m), 3.72 (3H, s), 6.60–6.75 (2H, m), 7.00–7.10 (1H, m), 8.15 (3H, br s)

MASS (m/z): 191 (M+), 148

Preparation 80

The following compounds were obtained according to a similar manner to that of Preparation 79.

1) (R)-3-Methoxy-6,7,8,9-tetrahydro-5H-benzocyclohepten-6-amine hydrochloride mp: 264°–265° C.

[a]$_D^{22}$= −29.59° (c=1.22, MeOH)

IR (Nujol): 2610, 2500, 1610, 830, 760, 720 cm$^{-1}$

NMR (DMSO-d$_6$, δ): 1.15–1.25 (1H, m), 1.65–2.05 (2H, m), 2.05–2.25 (1H, m), 2.60–2.75 (2H, m), 2.75–3.10 (3H, m), 3.72 (3H, s), 6.60–6.75 (2H, m), 7.00–7.10 (1H, m), 8.20 (3H, br s)

MASS (m/z): 191 (M+), 148

2) 3-Methoxy-6,7,8,9-tetrahydro-5H-benzocyclohepten-6-amine hydrochloride mp: 230°–233° C. (dec.)

IR (Nujol): 2600, 2520, 1610, 760 cm$^{-1}$

NMR (DMSO-d$_6$, δ): 1.15–1.45 (1H, m), 1.60–2.05 (2H, m), 2.0.5–2.30 (1H, m), 2.55–2.80 (2H, m), 2.80–3.15 (3H, m), 3.72 (3H, s), 6.60–6.85 (2H, m), 6.9 5–7.10 (1H, m), 8.19 (3H, br s)

MASS (m/z): 191 (M+), 148

Preparation 81

To a mixture of (S)-3-methoxy-6,7,8,9-tetrahydro-5H-benzocyclohepten-6-ol (1.00 g), phthalimide (0.77 g), and triphenylphosphine (1.36 g) in dry tetrahydrofuran, was added dropwise a solution of diethyl azodicarboxylate (0.91 g) in dry tetrahydrofuran (3 ml) at 26° C.~33° C. The mixture was stirred at ambient temperature for 2 days. The solvent was evaporated in vacuo. Diethyl ether (30 ml) was added to the residue and the mixture was stirred and the resulting precipitates (triphenyl phosphinoxide) were removed by filtration. The filtrate was evaporated in vacuo. The residue was purified by column chromatography (silica gel, n-hexane:ethyl acetate=5:1) to give (R)-N-(3-methoxy-6,7,8,9-tetrahydro-5H-benzocyclohepten-6-yl)phthalimide as a white powder (0.43 g).

mp: 132°–133° C.

[α]$_D^{25}$= −40.76° (c=0.91, CH$_2$Cl$_2$)

IR (Nujol): 1770, 1700, 1610, 800, 720 cm$^{-1}$

NMR (CDCl$_3$, δ): 1.15–1.70 (1H, m), 1.90–2.20 (2H, m), 2.40–3.00 (4H, m), 3.77 (3H, s), 3.90–4.10 (1H, m), 4.10–4.30 (1H, m), 6.60–6.70 (2H, m), 7.00–7.10 (1H, m), 7.60–7.75 (2H, m), 7.80–7.90 (2H, m)

MASS (m/z): 321 (M+), 227, 174

Preparation 82

A mixture of (R)-N-(3-methoxy-6,7,8,9-tetrahydro-5H-benzocyclohepten-6-yl)phthalimide (0.50 g) and hydrazine monohydrate (0.2 ml) in ethanol (8.0 ml) was refluxed for 1 hour. The resulting precipitates were removed by filtration and the filtrate was evaporated in vacuo. The residue was partitioned between ethyl acetate and 1N aqueous sodium hydroxide solution. The organic layer was washed with water and brine, dried over magnesium sulfate, and evaporated in vacuo. The residue was treated with 4N hydrogen chloride in ethyl acetate to give (R)-3-methoxy-6,7,8,9-tetrahydro-5H-benzocyclohepten-6-amine hydrochloride (0.29 g).

mp: 264°–265° C.

Preparation 83

A solution of 2-bromoacetylnaphthalene (7.00 g) and tetra-n-butyl ammonium bromide (0.905 g) in 1,2-dichloroethane (226 ml) was refluxed for 3.5 hours, evaporated in vacuo and extracted with dichloromethane. The extract was washed with brine, dried over magnesium sulfate, and evaporated in vacuo. The residue was washed with n-hexane to afford 2-chloroacetylnaphthalene (5.43 g) as a yellow powder.

IR (Nujol): 1680 cm$^{-1}$

NMR (CDCl$_3$, δ): 4.81 (2H, s), 7.5–7.6 (2H, m), 7.8–8.0 (4H, m), 8.43 (1H, s)

MASS (m/z): 206 and 204 (M+), 155, 127

Preparation 84

A mixture of 2-acetonaphthone (3.40 g) and selenium dioxide (4.88 g) in dioxane (200 ml) and water (1 ml) was stirred under reflux for 6 hours and filtered. The filtrate was concentrated in vacuo and extracted with diethyl ether. The extract was washed twice with brine, dried over magnesium sulfate, and concentrated in vacuo to give a pale brown powder of 2,2″-oxybis[2-hydroxy-2′-acetonaphthone] (3.21 g).

mp: 112°–122° C.

IR (Nujol): 3320, 1690 cm$^{-1}$

NMR (CDCl$_3$, δ): 5.06 (2H, br s), 6.58 (2H, s), 7.2–8.3 (12H, m), 8.75 (2H, s)

MASS (m/z): 184, 155, 127

Preparation 85

The following compounds were obtained according to a similar manner to that of Preparation 84.

1) 2,2''-Oxybis[2-hydroxy-1'-acetonaphthone]
mp: 89°–91° C.
IR (Nujol): 3410, 3270, 1665 cm$^{-1}$
NMR (CDCl$_3$, δ): 5.16 (2H, br s), 6.50 (2H, s), 7.4–7.7 (6H, m), 7.85 (2H, d, J=8.6 Hz), 8.06 (2H, d, J=8.2 Hz), 8.40 (2H, dd, J=1.1 Hz, 7.4 Hz), 8.99 (2H, dd, J=0.8 Hz, 8.4 Hz)
MASS (m/z): 184, 155

2) 2,2''-oxybis[2-hydroxy-1-(5'-indanyl)ethanone]
mp: 111°–122° C.
IR (Nujol): 3380, 1670, 1600 cm$^{-1}$
NMR (CDCl$_3$, δ): 2.06 (2H, t, J=7.4 Hz), 2.14 (2H, t, J=7.4 Hz), 2.94 (5H t, J=7.4 Hz), 5.06 (2H, d, J=10.0 Hz), 6.33 (2H, d, J=10.0 Hz), 7.29 (2H, d, J=11.9 Hz), 7.92 (2H, d, J=11.9 Hz), 7.95 (2H, s)

2) 2,2''-Oxybis[1-(5'-benzofurazanyl)-2-hydroxyethanone]
NMR (CDCl$_3$, δ): 4.46 (2H, d, J=10 Hz), 5.72 (2H, d, J=10 Hz), 7.9–8.2 (4H, m), 8.6–8.7 (2H, m)

Preparation 86

To an ice-cooled suspension of potassium tert-butoxide (0.82 g) in tetrahydrofuran (6.6 ml) was added trimethylsulfonium iodide (98% purity; 1.5 g) in dimethyl sulfoxide (6.6 ml). After the addition was complete, piperonal (1.0 g) in tetrahydrofuran (3.3 ml) was added dropwise to the mixture while the internal temperature was maintained below 5° C. After stirring at ambient temperature for 1 hour, the mixture was poured into water and extracted once with ethyl acetate. The extract was washed twice with water and once with brine, dried over anhydrous sodium sulfate, and concentrated in vacuo to give 3,4-methylenedioxyphenyloxirane (1.0 g), which was used for next reaction without further purification.
NMR (CDCl$_3$, δ): 2.74 (1H, dd, J=2 Hz, 5 Hz), 3.09 (1H, dd, J=4 Hz, 5 Hz), 3.78 (1H, dd, J=2 Hz, 4 Hz), 5.94 (2H, s), 6.6–6.9 (3H, m)
MASS (m/z): 164

Preparation 87

To an ice-cooled mixture of L-tyrosine benzyl ester p-toluenesulfonate (41.0 g), pyridine (16.4 ml), and dichloromethane (92 ml) was added methyl chloroformate (7.8 ml). The mixture was stirred in an ice-bath for 1 hour, diluted with water, and extracted once with dichloromethane. The extract was concentrated in vacuo and the residue was dissolved in ethyl acetate, washed with water and brine, dried over anhydrous magnesium sulfate, and concentrated in vacuo. Purification of the crude product by column chromatography on silica gel (gradient elution; 10:1 to 5:1 chloroform-ethyl acetate) gave N-methoxycarbonyl-L-tyrosine benzyl ester (22.0 g).
mp: 100°–101° C.
IR (Nujol): 3360, 1720, 1700 cm$^{-1}$
NMR (CDCl$_3$, δ): 3.01 (2H, d, J=6 Hz), 3.65 (3H, s), 4.5–4.8 (1H, m), 4.8–4.6 (4H, m), 6.6–6.8 (2H, m), 6.8–7.0 (2H, m), 7.2–7.6 (5H, m)
MASS (m/z): 329

Preparation 88

A mixture of N-methoxycarbonyl-L-tyrosine benzyl ester (22.0 g), methyl iodide (10.8 ml), potassium carbonate (24.0 g), and N,N-dimethylformamide (87 ml) was stirred at ambient temperature for 5 hours. The mixture was diluted with dichloromethane (87 ml) and filtered. The filtrate was concentrated in vacuo and the residue was dissolved in ethyl acetate, washed with water and brine, dried over anhydrous magnesium sulfate, and concentrated in vacuo. The crude product was purified by pulverization with petroleum ether to give N-methoxycarbonyl-O-methyl-L-tyrosine benzyl ester (16.0 g).
mp: 83°–84° C.
IR (Nujol): 3430, 1730 cm$^{-1}$
NMR (CDCl$_3$, δ): 3.03 (2H, d, J=6 Hz), 3.66 (3H, s), 3.76 (3H, s), 4.5–4.8 (1H, m), 5.0–5.3 (3H, m), 6.7–6.8 (2H, m), 6.8–7.0 (2H, m), 7.2–7.5 (5H, m)
MASS (m/z): 268 (M-H$_2$NCO$_2$Me)$^+$

Preparation 89

A mixture of N-methoxycarbonyl-O-methyl-L-tyrosine benzyl ester (14.5 g), 10% palladium on carbon (0.73 g), and tetrahydrofuran (145 ml)-water (14.5 ml) was shaken under hydrogen at ambient temperature for 2 hours. An additional 10% palladium on carbon (0.73 g) was added to the mixture and shaking was continued for an additional 2 hours. The catalyst was filtered off and washed with tetrahydrofuran. The filtrate and washings were combined and concentrated in vacuo to afford N-methoxycarbonyl-O-methyl-L-tyrosine (10.5 g).
mp: 85°–86° C.
IR (Nujol): 3260, 3140, 1730, 1660 cm$^{-1}$
NMR (CDCl$_3$, δ): 2.9–3.2 (2H, m), 3.67 (3H, s), 3.79 (3H, s), 4.5–4.8 (1H, m), 5.0–5.2 (1H, m), 6.7–6.9 (2H, m), 7.0–7.2 (2H, m)
MASS (m/z): 221 (M-CH$_3$OH)$^+$

Preparation 90

To a solution of N-methoxycarbonyl-O-methyl-L-tyrosine (0.5 g) in dichloromethane (2 ml) was added thionyl chloride (0.29 ml). After stirring for 1 hour at ambient temperature, the reaction mixture was concentrated in vacuo. The residue was dissolved in dichloromethane (5 ml) and treated with 0.9M ethylaluminum dichloride in dichloromethane (4.4 ml) in an ice-bath. The mixture was allowed to warm to ambient temperature and stirred overnight. The mixture was poured into concentrated hydrochloric acid containing crashed ice and extracted once with dichloromethane. The extract was washed with water and brine, dried over anhydrous magnesium sulfate, and concentrated in vacuo. Purification of the residue by column chromatography on silica gel (eluent; 10:1 dichloromethane-ethyl acetate) gave 6-methoxy-2-(methoxycarbonylamino)indan-1-one (0.12 g).
mp: 174°–177° C.
IR (Nujol): 3330, 1720, 1680 cm$^{-1}$
NMR (DMSO-d$_6$, δ): 2.87 (1H, dd, J=5 Hz, 16 Hz), 3.38 (1H, dd, J=8 Hz, 16 Hz), 3.54 (3H, s), 3.80 (3H, s), 4.26 (1H, ddd, J=5 Hz, 8 Hz, 8 Hz), 7.11 (1H, d, J=2 Hz), 7.28 (1H, dd, J=2 Hz, 8 Hz), 7.45 (1H, d, J=8 Hz), 7.69 (1H, d, J=8 Hz)
MASS (m/z): 235

Preparation 91

A mixture of 6-methoxy-2-(methoxycarbonylamino)indan-1-one (0.30 g), boron trifluoride etherate (0.90 ml), and ethanedithiol (0.90 ml) was stirred at ambient temperature for 2 hours. The mixture was poured into saturated aqueous sodium bicarbonate and extracted twice with ethyl acetate. The combined extracts were washed with brine, dried over anhydrous sodium sulfate, and concentrated in vacuo. The residue was purified by column chromatography on silica gel (gradient elution; 5:1 to 2:1 n-hexane-ethyl acetate) to give 6-methoxy-2-(methoxycarbonylamino)indan-1-one ethylene dithioacetal (0.48 g) as an oil.

IR (Film): 3330, 1700 cm$^{-1}$

NMR (CDCl$_3$, δ): 2.63 (1H, dd, J=8 Hz, 15 Hz), 3.0–3.6 (5H, m), 3.72 (3H, s), 3.81 (3H, s), 4.5–4.8 (1H, m), 5.3–5.6 (1H, m), 6.78 (1H, dd, J=2 Hz, 8 Hz), 6.9–7.1 (2H, m)

MASS (m/z): 311

Preparation 92

A mixture of 6-methoxy-2-(methoxycarbonylamino)indan-1-one ethylene dithioacetal (0.12 g), Raney nickel (suspension in water; 5 ml), and ethanol (12 ml) was refluxed for 0.5 hour. The mixture was filtered and the catalyst was washed with hot ethanol. The filtrate and washings were combined and concentrated in vacuo. Purification of the residue by column chromatography on silica gel (eluent; chloroform) gave 5-methoxy-N-methoxycarbonylindan-2-amine (0.08 g).

mp: 120°–121° C.

IR (Nujol): 3290, 1670 cm$^{-1}$

NMR (DMSO-d$_6$, δ): 2.5–2.9 (2H, m), 2.9–3.2 (2H, m), 3.52 (3H, s), 3.69 (3H, s), 4.1–4.3 (1H, m), 6.68 (1H, dd, J=2 Hz, 8 Hz), 6.77 (1H, d, J=2 Hz), 7.07 (1H, d, J=8 Hz), 7.3–7.5 (1H, m)

MASS (m/z): 221

Preparation 93

A mixture of 5-methoxy-N-methoxycarbonylindan-2-amine (0.25 g) and 47% hydrobromic acid (20 ml) was refluxed for 4 hours. After cooling, the mixture was concentrated in vacuo. Toluene was added to the residue and the whole was concentrated in vacuo to dryness to give 5-hydroxyindan-2-amine hydrobromide (0.26 g).

mp: >235° C. (dec.)

IR (Nujol): 3370 cm$^{-1}$

NMR (DMSO-d$_6$, δ): 2.7–3.0 (2H, m), 3.0–3.3 (2H, m), 3.8–4.1 (1H, m), 6.5–6.8 (2H, m), 7.04 (1H, d, J=8 Hz), 8.03. (3H, br s), 9.24 (1H, br s)

MASS (m/z): 149

Preparation 94

A mixture of 5-hydroxyindan-2-amine hydrobromide (0.66 g), triethylamine (0.95 ml), di-tert-butyl dicarbonate (0.75 g), and N,N-dimethylformamide (6.6 ml) was stirred at ambient temperature for 4 hours. The mixture was diluted with ethyl acetate and the precipitates were filtered off. The filtrate was concentrated in vacuo to afford the crude product which was purified by column chromatography on silica gel (eluent; 5:1 n-hexane-ethyl acetate) to give N-tert-butoxycarbonyl-5-hydroxyindan-2-amine (0.44 g).

IR (Film): 3330, 1670 cm$^{-1}$

NMR (CDCl$_3$, δ): 1.45 (9H, s), 2.6–2.8 (2H, m), 3.1–3.4 (2H, m), 4.3–4.6 (1H, br m), 4.6–4.9 (1H, br m), 5.32 (1H, br s), 6.64 (1H, dd, J=2 Hz, 8 Hz), 6.70 (1H, br s), 7.04 (1H, d, J=8 Hz)

MASS (m/z): 249

Preparation 95

A mixture of N-tert-butoxycarbonyl-5-hydroxyindan-2-amine (0.42 g), potassium carbonate (0.34 g), ethyl bromoacetate (0.24 ml), and N,N-dimethylformamide (4.2 ml) was stirred at ambient temperature for 20 hours. An additional portion of ethyl bromoacetate (0.12 ml) and potassium carbonate (0.17 g) was added to the mixture, and stirring was continued for an additional 12 hours. The mixture was diluted with ethyl acetate and the precipitates were filtered off. The filtrate was concentrated in vacuo, and the residue was dissolved in ethyl acetate, washed with water and brine, dried over anhydrous sodium sulfate, and concentrated in vacuo. Purification of the residue by column chromatography on silica gel (eluent; 5:1 n-hexane-ethyl acetate) to give N-tert-butoxycarbonyl-5-ethoxycarbonylmethoxyindan-2-amine (0.44 g).

mp: 73°–75° C.

IR (Nujol): 3400, 1750, 1700 cm$^{-1}$

NMR (CDCl$_3$, δ): 1.30 (3H, t, J=7 Hz), 1.44 (9H, s), 2.6–2.9 (2H, m), 3.1–3.4 (2H, m), 4.27 (2H, q, J=7 Hz), 4.3–4.5 (1H, br m), 4.58 (2H, s), 4.6–4.9 (1H, br m), 6.72 (1H, dd, J=2 Hz, 8 Hz), 6.76 (1H, br s), 7.10 (1H, d, J=8 Hz)

MASS (m/z): 335

Preparation 96

A mixture of N-tert-butoxycarbonyl-5-ethoxycarbonyl-methoxyindan-2-amine (0.39 g) and 4N hydrogen chloride in 1,4-dioxane (11.6 ml) was allowed to stand at ambient temperature for 2 hours. The mixture was concentrated in vacuo to afford the solid, which was washed with diisopropyl ether and dried in vacuo to give 5-(ethoxycarbonylmethoxy)indan-2-amine hydrochloride (0.247 g).

mp: 155°–160° C.

IR (Nujol): 2600, 1750 cm$^{-1}$

NMR (DMSO-d$_6$, δ): 1.21 (3H, t, J=7 Hz), 2.8–3.0 (2H, m), 3.0–3.4 (2H, m), 3.9–4.1 (1H, m), 4.15 (2H, q, J=7 Hz), 4.73 (2H, s), 6.75 (1H, dd, J=2 Hz, 8 Hz), 6.85 (1H, d, J=2 Hz), 7.16 (1H, d, J=8 Hz), 8.23 (3H, br s)

MASS (m/z): 235

Example 1

1) A mixture of 6-amino-3-ethoxycarbonylmethoxy-6,7,8,9-tetrahydro-5H-benzocycloheptene (1.0 g), (R)-3-chlorostyrene oxide (0.58 g), and n-propanol (7.6 ml) was refluxed for 3 hours. After cooling, the reaction mixture was concentrated in vacuo. A crude column chromatography on silica gel (gradient elution; 3:1 n-hexane-ethyl acetate to ethyl acetate to ethyl acetate-ethanol; 25:1 to 10:1) afforded about 0.8 g of crude product. Another flash column chromatography on silica gel (gradient elution; 1:3 n-hexane-ethyl acetate to 25:1 ethyl acetate-ethanol) was performed to give a mixture of (1R,6′R)- and (1R,6′S)-2-[(3-ethoxycarbonyl-methoxy-6,7,8,9-tetrahydro-5H-benzocyclohepten-6-yl)amino]-1-(3-chlorophenyl)ethanol (0.60 g).

2) The obtained mixture (0.60 g) was dissolved in ethyl acetate (2.5 ml) and, with cooling, treated with 4N hydrogen chloride in ethyl acetate (3.5 ml). After stirring for 5 minutes, the mixture was concentrated in vacuo. The residue was dissolved in ethanol (5 ml) and precipitated by the addition of n-hexane (40 ml). The solvent was removed in vacuo, and the resulting solid was collected, washed with n-hexane, and dried to give a mixture of (1R,6′R)- and (1R,6′S)-2-[(3-ethoxycarbo-nyl-methoxy-6,7,8,9-tetrahydro-5H-benzocyclohepten-6-yl)amino]-1-(3-chlorophenyl)ethanol hydrochloride (0.54 g).

mp: 114°–119° C.

IR (Nujol): 3400, 3170, 1740 cm$^{-1}$

NMR (DMSO-d$_6$, δ): 1.19 (3H, t, J=7 Hz), 1.20 (3H, t, J=7 Hz), 1.1-1.5 (2H, m), 1.7-2.1 (4H, m), 2.2-2.5 (2H, m), 2.-5-2.9 (4H, m), 2.9-3.4 (12H, m), 4.14 (2H, q, J=7 Hz), 4.16 (2H, q, J=7 Hz), 4.70 (2H, s), 4.71 (2H, s), 4.9-5.1 (2H, m), 6.3-6.4 (2H, m), 6.6-6.8 (2H, m), 6.8-6.9 (2H, m), 7.0-7.1 (2H, m), 7.3-7.6 (5H m), 8.8-9.6 (2H, m)

FAB-MASS (m/z): 420 (M$^+$+3-HCl), 418 (M$^+$+1-HCl)

Example 2

The following compounds were obtained according to a similar manner to that of Example 1.

1) (1R,6'R)- and (1R,6'S)-2-[(2-Ethoxycarbonylmethoxy-6,7,8,9-tetrahydro-5H-benzocyclohepten-6-yl)amino]-1-(3-chlorophenyl)ethanol hydrochloride IR (Film): 3300, 1740 cm$^{-1}$ NMR (CDCl$_3$, δ): 1.29 (6H, t, J=7 Hz), 1.3-2.3 (8H, m), 2.3-2.6 (2H, m), 2.6-2.9 (4H, m), 2.9-3.5 (10H, m), 4.26 (4H, q, J=7 Hz), 4.56 (4H, s), 5.2-5.8 (2H, m), 6.4-6.8 (4H, m), 6.9-7.6 (10H, m), 8.2-8.8 (2H, m), 9.6-10.4 (2H, m)

FAB-MASS (m/z): 420 (M$^+$+3-HCl), 418 (M$^+$+1-HCl)

2) (1R,6'R)- and (1R,6'S)-2-[(3-Ethoxycarbonylmethoxy-5,6,7,8,9,10-hexahydrobenzocycloocten-6-yl)amino]-1-(3-chlorophenyl)ethanol hydrochloride mp: 62°-66° C.

IR (Nujol): 3275, 1750, 1605, 1575, 1500, 1200 cm$^{-1}$

NMR (DMSO-d$_6$, δ): 0.80-1.0 (2H, m), 1.20 (6H, t, J=7.1 Hz), 1.30-1.90 (10H, m), 2.57-2.89 (4H, m), 3.0-3.45 (10H, m), 4.16 (4H, q, J=7.1 Hz), 4.72 (4H, m), 4.95-5.13 (2H, m), 6.3-6.4 (2H, m), 6.7-6.8 (2H, m), 6.8-6.9 (2H, m), 7.0-7.1 (2H, m), 7.35-7.6 (5H m), 8.5-9.4 (4H, m)

FAB-MASS (m/z): 434 (M$^+$+3-HCl), 432 (M$^+$+1-HCl)

3) (1R,6'S)-2-[(3-Ethoxycarbonylmethoxy-6,7,8,9-tetrahydro-5H-benzocyclohepten-6-yl)amino]-1-(3-chlorophenyl)ethanol hydrochloride mp: 91°-98° C.

[α]$_D^{28}$= +12.45° (c=0.53, EtOH)

IR (Nujol): 3360, 1750, 1595 cm$^{-1}$

NMR (DMSO-d$_6$, δ): 1.19 (3H, t, J=7 Hz), 1.2-1.4 (1H, m), 1.7-2.1 (2H, m), 2.2-2.4 (1H, m), 2.6-2.8 (2H, m), 2.9-3.3 (5H, m), 4.15 (2H, d, J=7 Hz), 4.70 (2H, s), 4.9-5.1 (1H, m), 6.33 (1H, d, J=4 Hz), 6.66 (1H, dd, J=2 Hz, 8 Hz), 6.87 (1H, d, J=2 Hz), 7.03 (1H, d, J=8 Hz), 7.3-7.6 (4H, m), 8.6-9.3 (2H, m)

FAB-MASS (m/z): 420 (M$^+$+3-HCl), 418 (M$^+$+1-HCl)

Analysis Calcd. for C$_{23}$H$_{28}$ClNO$_4$·HCl·H$_2$O C 58.47, H 6.61, N 2.96 Found: C 58.63, H 6.79, N 2.98

4) (1R,6'R)-2-[(3-Ethoxycarbonylmethoxy-6,7,8,9-tetrahydro-5H-benzocyclohepten-6-yl)amino]-1-(3chlorophenyl)ethanol hydrochloride IR (Nujol): 3500-2000, 1740 cm$^{-1}$ (DMSO-d$_6$, δ): 1.20 (3H, t, J=7 Hz), 1.1-1.4 (1H, m), 1.6-2.1 (2H, m), 2.2-2.4 (1H, m), 2.6-2.8 (2H, m), 2.9-3.4 (5H, m), 4.16 (2H, q, J=7 Hz), 4.71 (2H, s), 4.9-5.1 (1H, m), 6.34 (1H, d, J=3 Hz), 6.67 (1H, dd, J=2 Hz, 8 Hz), 6.81 (1H, d, J=2 Hz), 7.04 (1H, d, J=8 Hz), 7.4-7.6 (4H, m), 8.6-8.9 (1H, m), 9.1-9.4 (1H, m)

FAB-MASS (m/z): 420 (M$^+$+3-HCl), 418 (M$^+$+1-HCl)

5) (1R,2'R)- and (1S,2'S)-2-[(7-Ethoxycarbonylmethoxy-1,2,3,4-tetrahydro-2-naphthyl)amino]-1-(3,4-methylenedioxyphenyl)ethanol hydrochloride mp: 175°-180° C.

IR (Nujol): 3320, 2500, 2400, 1750 cm$^{-1}$

NMR (DMSO-d$_6$, δ): 1.20 (6H, t, J=7 Hz), 1.6-2.0 (2H, m), 2.2-2.5 (2H, m), 2.6-3.6 (14H, m), 4.15 (4H, q, J=7 Hz), 4.71 (4H, s), 4.9-5.1 (2H, m), 6.02 (4H, s), 6.1-6.2 (2H, m), 6.6-6.8 (4H, m), 6.8-7.1 (5H m), 8.7-9.1 (2H, br m), 9.2-9.6 (2H, br m)

MASS (m/z): 414 (M+1)$^+$ 6) (1R,2'S)- and (1S,2'S)-2-[(7-Ethoxycarbonylmethoxy-1,2,3,4-tetrahydro-2-naphthyl)amino]-1-(5-benzofurazanyl)ethanol hydrochloride mp: 205°-220° C.

IR (Nujol): 3300, 1750 cm$^{-1}$

NMR (DMSO-d$_6$, δ): 1.20 (6H, t, J=7 Hz), 1.6-2.0 (2H, m), 2.2-2.5 (2H, m), 2.6-3.7 (14H, m), 4.15 (4H, q, J=7 Hz), 4.72 (2H, s), 5.25 (2H, m), 6.5-6.9 (6H, m), 7.02 (2H, d, J=8 Hz), 7.71 (2H, d, J=9 Hz), 8.05 (2H, s ), 8.12 (2H, d, J=9 Hz), 8.9-9.3 (2H, br m), 9.4-9.8 (2H, br m)

MASS (m/z): 412 (M+1)$^+$ 7) (1R,6'R)- and (1R,6'S)-2-[N-Benzyl-[3-(2-ethoxycarbonylpropan-2-yloxy)-6,7,8,9-tetrahydro-5H-benzocyclohepten-6-yl]amino]-1-(3-chlorophenyl)ethanol hydrochloride mp: 95°-106° C.

IR (Nujol): 3170, 1720, 1600 cm$^{-1}$

NMR (DMSO-d$_6$, δ): 1.0-1.3 (8H, m), 1.4-1.6 (12H, m), 1.8-2.2 (4H, m), 2.4-2.8 (6H, m), 2.9-3.7 (10H, m), 4.05-4.3 (4H, m), 4.6-5.6 (6H, m), 6.3-8.0 (26H, m), 10.2-11.2 (2H, m)

MASS (m/z): 536 (M$^+$+1-HCl)

8) (−)-(2'S)-1-(6-Chloro-2-pyridyl)-2-[(7-ethoxycarbonylmethoxy-1,2,3,4-tetrahydro-2-naphthyl)amino]ethanol mp: 107°-109° C.

[α]$_D^{28.4}$= −93.4° (c=0.20, ethanol)

IR (Nujol): 3260, 1730 cm$^{-1}$

NMR (CDCl$_3$, δ): 1.30 (3H, t, J=7.1 Hz), 1.46-1.73 (1H, m), 1.96-2.15 (1H, m), 2.44-3.30 (7H, m), 1.70-3.10 (2H, br m), 4.27 (2H, q, J=7.1 Hz), 4.66-4.81 (1H, m), 6.59 (1H, d, J=2.5 Hz), 6.69 (1H, dd, J=2.7 Hz, 8.4 Hz), 6.98 (1H, d, J=8.4 Hz), 7.23 (1H, d, J=7.8 Hz), 7.44 (1H, d, J=7.6 Hz), 7.67 (1H, pseudo t, J=7.7 Hz)

9) (1R,2'R)- and (1R,2'S)-1-(3-Chlorophenyl)-2-(N-methylthioethyl-7-nitro-1,2,3,4-tetrahydro-2-naphthyl)aminoethanol IR (Neat): 3400, 1510, 1340 cm$^{-1}$ (CDCl$_3$, δ): 1.46-1.95 (2H, m), 1.99-2.24 (2H, m), 2.16 (3H, s), 2.17 (3H, s), 2.40-3.24 (22H, m), 4.26 (2H, br s), 4.57-4.75 (2H, m), 7.26 (10H, s ), 7.40 (2H, s ), 7.90-8.09 (4H, m)

10) (1R,6'R)- and (1R,6'S)-2-[N-Benzyl-(3-ethoxycarbonylmethylamino-6,7,8,9-tetrahydro-5H-benzocyclohepten-6-yl)amino]-1-(3-chlorophenyl)ethanol dihydrochloride mp: 132°-134° C.

IR (Nujol): 3225, 1740 cm$^{-1}$

Example 3

The following compounds were obtained according to a similar manner to that of Example 1-1).

1) (1R,2'R)- and (1R,2'S)-2-[(5-Ethoxycarbonylmethoxy-2-indanyl)amino]-1-(3-chlorophenyl)ethanol mp 104°-105° C.

IR (Nujol): 1760 cm$^{-1}$

NMR (CDCl$_3$, δ): 1.29 (6H, t, J=7 Hz), 2.6-3.3 (12H, m), 3.6-3.8 (2H, m), 4.26 (4H, q, J=7 Hz), 4.58 (4H, s), 4.65 (2H, dd, J=3 Hz, 8 Hz) ), 6.6 -6.8 (4H, m), 7.09 (2H, d, J=8 Hz), 7.1-7.5 (8H m)

FAB-MASS (m/z): 392 (M+ +3), 390 (M+ +1)

2) (1R,6'R)-2-[(3-Ethoxycarbonylmethoxy-6,7,8,9-tetrahydro-5H-benzocyclohepten-6-yl)amino]-1-(3-chlorophenyl)ethanol mp: 98°-100° C.

$[\alpha]_D^{29} = -38.3°$ (c=0.62, EtOH)

IR (CH$_2$Cl$_2$ solution): 3450–3400, 1750 cm$^{-1}$

NMR (DMSO-d$_6$, δ): 1.18 (3H, t, J=7 Hz), 1.2–2.1 (4H, m), 2.5–2.9 (7H, m), 4.14 (2H, q, J=7 Hz), 4.5–4.7 (1H, m), 4. 68 (2H, s), 5.3–5.6 (1H, m), 6.58 (1H, dd, J=2 Hz, 8 Hz), 6.73 (1H, d, J=2 Hz), 6.96 (1H, d, J=8 Hz), 7.2–7.5 (4H, m)

MASS (m/z): 420 (M+3), 418 (M+1)

Analysis Calcd. for C$_{23}$H$_{28}$ClNO$_4$ C 66.10, H 6.75, N 3.35 Found: C 66.21, H 6.94, N 3.36

3) (1R,6'R)- or (1R,6'S)- or (1S,6'R)- or (1S,6'S)-1-(2-Naphthyl)-2-[N-benzyl-(3-hydroxy-6,7,8,9-tetrahydro-5H-benzocyclohepten-6-yl)amino]ethanol (isomer A)

NMR (CDCl$_3$, δ): 1.2–1.3 (1H, br), 2.0 (3H, br), 2.6–2.8 (7H, m), 3.67 (1H, d, J=13.6 Hz), 3.97 (1H, d, J=13.6 Hz), 4.70 (1H, dd, J=3.9 Hz, 9.9 Hz), 6.51 (1H, dd, J=2.6 Hz, 8.0 Hz), 6.62 (1H, d, J=2.6 Hz), 6.88 (1H, d, J=8.0 Hz), 7.1–7.5 (8H m), 7.8 (4H, m)

MASS (m/z): 438 (M+ +1)

4) (1R,6'R)- or (1R,6'S) - or (1S,6'R)- or (1S,6'S)-1-(2-Naphthyl)-2-[N-benzyl -(3-hydroxy-6,7,8,9-tetrahydro-5H-benzocyclohepten-6 -yl)amino]ethanol (isomer B)

NMR (CDCl$_3$, δ): 1.2–1.3 (1H, br), 1.4–1.7 (1H, m), 1.9–2.0 (1H, m), 2.2–2.3 (1H, m), 2.6–3.1 (7H, m), 3.60 (1H, d, J=13.6 Hz), 3.84 (1H, d, J=13.6 Hz), 4.59 (1H, dd, J=3.6 Hz, 10.1 Hz), 6.51 (1H, dd, J=2.6 Hz, 9.0 Hz), 6.59 (1H, d, J=2.6 Hz), 6.87 (1H, d, J=9.0 Hz), 7.1–7.5 (5H m), 7.7–7.8 (4H, m)

5) (1R,2'S)- or (1S,2'S)-1-(2-Naphthyl)-2-[(7-ethoxycarbonylmethoxy-1,2,3,4-tetrahydro-2-naphthyl)amino]ethanol mp: 113°–114° C.

$[\alpha]_D = -74.16°$ (c=0.48, MeOH)

IR (Nujol): 3430, 1725 cm$^{-1}$

NMR (CDCl$_3$, δ): 1.29 (3H, t, J=7.2 Hz), 1.5–1.7 (1H, m), 2.0 (1H, m), 2.2–3.2 (9H, m), 4.22 (2H, q, J=7.2 Hz), 4.56 (2H, s),.4.89 (1H, dd, J=3.6 Hz, 8.8 Hz), 6.59 (1H, d, J=2.5 Hz), 6.68 (1H, dd, J=2.5 Hz, 8.3 Hz), 6.99 (1H, d, J=8.3 Hz), 7.4–7.5 (3H, m), 7.8–7.9 (4H, m)

MASS (m/z): 420 (M+ +1), 401 and 388

Example 4

A mixture of 2-ethoxycarbonylmethoxy-6,7,8,9-tetrahydro-5H-benzocyclohepten-6-amine (0.69 g), (R)-3-chlorostyrene oxide (0.44 g), and n-propanol (5.2 ml) was refluxed for 1.5 hours. After cooling, the reaction mixture was concentrated in vacuo. The residue was purified by column chromatography on silica gel (100:1 ethyl acetate-ethanol) to give a mixture of (1R,6'R)- and (1R,6'S)-2-[(2-ethoxycarbonylmethoxy-6,7,8,9-tetrahydro-5H-benzocyclohepten-6-yl)amino]-1-(3-chlorophenyl)ethanol (0.46 g).

The obtained mixture (0.33 g) was dissolved in ethanol (3.3 ml) and treated with oxalic acid (71 mg) in ethanol (3.3 ml). After 5 minutes, the mixture was concentrated in vacuo. The residue was dissolved in ethyl acetate (3.3 ml) and precipitated by the addition of diisopropyl ether (3.3 ml). The solvent was removed in vacuo and the precipitate was dried to give a mixture of (1R,6'R)- and (1R,6'S)-2-[(2-ethoxycarbonylmethoxy-6,7,8,9-tetrahydro-5H-benzocyclohepten-6-yl)amino]-1-(3-chlorophenyl)ethanol oxalate (0.40 g).

mp: 65°–87° C.

IR (Nujol): 3500–2200, 1750–1730 cm$^{-1}$

NMR (DMSO-d$_6$, δ): 1.1–1.5 (2H, m), 1.20 (6H, t, J=7 Hz), 1.6–2.4 (6H, m), 2.5–2.8 (4H, m), 2.9–3.4 (10H, m), 4.15 (4H, q, J=7 Hz), 4.71 (4H s), 4.8–5.1 (2H, m), 5.1–6.5 (4H, m), 6.5–6.8 (4H, m), 7.0–7.2 (2H, m), 7.3–7.6 (5H m)

FAB-MASS (m/z): 420 (M+ +3-C$_2$H$_2$O$_4$), 418 (M+ +1-C$_2$H$_2$O$_4$)

Example 5

To a suspension of (1R,6'R)-2-[(3-ethoxycarbonylmethoxy-6,7,8,9-tetrahydro-5H-benzocyclohepten-6-yl)amino]-1-(3-chlorophenyl)ethanol (0.30 g) in 50% aqueous ethanol (7.0 ml) was added sodium hydroxide (0.09 g). After stirring at ambient temperature for 0.5 hour, the reaction mixture was treated with 3M hydrochloric acid (0.8 ml) to afford the precipitate, which was collected and washed with cold water. The precipitate was suspended in ethanol (20 ml), and the mixture was stirred at ambient temperature overnight. Filtration followed by drying in vacuo to give (R)-[8-[(R)-2-(3-chlorophenyl)-2-hydroxyethylamino]-6,7,8,9-tetrahydro-5H-benzocyclohepten-2-yloxy]acetic acid (0.22 g).

mp: 265°–266° C.

$[\alpha]_D^{30} = -22.4°$ (c=0.56, 1N NaOH)

IR (Nujol): 3500–2200, 1600 cm$^{-1}$

NMR (DMSO-d$_6$+NaOD, δ): 1.0–2.1 (4H, m), 2.3–3.0 (7H, m), 3.9–4.2 (2H, m), 4.5–4.8 (1H, m), 6.4–7.0 (3H, m), 7.1–7.5 (4H, m)

MASS (m/z): 392 (M+3), 390 (M+1)

Example 6

The following compounds were obtained according to a similar manner to that of Example 5.

1) (S)-[8-[(R)-2-(3-Chlorophenyl)-2-hydroxyethylamino]-6,7,8,9-tetrahydro-5H-benzocyclohepten-2-yloxy]acetic acid mp: 247°–249° C. (dec.)

$[\alpha]_D^{22.8} = +26.2°$ (c=0.205, 1N NaOH)

IR (Nujol): 2700, 2350, 1600, 1580, 1540 cm$^{-1}$

NMR (DMSO-d$_6$+NaOD, δ): 1.19–2.04 (5H, m), 2.42–2.86 (6H, m), 4.02 (2H, s), 4.47–4.66 (1H, m), 6.47 (1H, dd, J=8.1 Hz, 2.5 Hz), 6.61 (1H, d, J=2.5 Hz), 6.88 (1H, d, J=8.1 Hz), 7.17–7.55 (4H, m)

Analysis Calcd. for C$_{21}$H$_{24}$ClNO$_4$ C 64.69, H 6.20, N 3.59 Found: C 64.47, H 6.29, N 3.59

2) 2-{(RS)-8-[(R)-2-(3-Chlorophenyl)-2-hydroxyethylamino]-6,7,8,9-tetrahydro-5H-benzocyclohepten-2yloxy}-2-methylpropionic acid mp: 134°–141° C. (dec.)

IR (Nujol): 1565, 1145 cm$^{-1}$

NMR (DMSO-d$_6$, δ): 1.0–1.3 (2H, m), 1.47 (6H, s), 1.50 (6H, s), 1.4–3.1 (20H, m), 4.8–4.95 (2H, m), 6.55 (2H, d, J=8.0 Hz), 6.68 (2H, s ), 6.89 (2H, d, J=8.0 Hz), 7.3–7.5 (8H, m)

3) 3-{(RS)-8-[(R)-2-(3-Chlorophenyl)-2-hydroxyethylamino]-6,7,8,9-tetrahydro-5H-benzocyclohepten-2-yl}propionic acid mp: 221°–224° C.

IR (Nujol): 3210, 2650, 2325 cm$^{-1}$

NMR (DMSO-d$_6$, δ): 1.18–2.10 (8H, m), 2.39–3.00 (22H, m), 4.58–4.75 (2H, m), 5.51 (2H, br s), 6.86–7.08 (6H, m), 7.23–7.48 (8H m)

4) (E)-3-{(RS)-8-[(R)-2-(3-Chlorophenyl )-2-hydroxyethylamino]-6,7,8,9-tetrahydro-5H-benzocyclohepten-2-yl}-acrylic acid mp: 222°–228° C.

IR (Nujol) 3500, 2670, 2340 cm$^{-1}$

NMR (DMSO-d$_6$, δ): 1.20–2.23 (5H m), 2.58–3.25 (14H, m), 4.74–5.00 (2H, m), 5.55 (2H, br s), 6.48 (2H, d, J=15.9 Hz), 7.13 (2H, d, J=7.8 Hz), 7.25–7.64 (14H, m)

Example 7

The following compounds were obtained according to a similar manner to that of Example 4.

1) (1R,7′R)- and (1R,7′S)-1-(3-Chlorophenyl)-2-[(2-ethoxycarbonylmethoxy-6,7,8,9-tetrahydro-5H-benzocyclohepten-7-yl)amino]ethanol oxalate mp: 90°–93° C. (dec.)

IR (Nujol): 3300, 2750–2300, 1745, 1600, 1195 cm$^{-1}$

NMR (DMSO-d$_6$, δ): 1.21 (6H, t, J=7.1 Hz), 1.15–1.45 (4H, m), 2.2–2.35 (4H, m), 2.65–2.85 (8H m), 2.95–3.35 (6H, m), 4.16 (4H, quartet, J=7.1 Hz), 4.71 (4H, s), 4.90 (2H, br d, J=7.4 Hz), 5.55 (8H, br), 6.63 (2H, dd, J=8.2 Hz, 2.6 Hz), 6.74 (2H, d, J=2.6 Hz), 7.04 (2H, J=8.2 Hz), 7.39 (6H, m), 7.48 (2H, m)

FAB-MASS (m/z): 420 and 418 (M$^+$(free)+1)

2) (1R,2′R)- and (1R,2′S)-1-(3-Chlorophenyl)-2-(N-methylthioethyl-7-nitro-1,2,3,4-tetrahydro-2-naphthyl)aminoethanol oxalate mp 90°–109° C.

IR (Nujol): 3250 cm$^{-1}$

NMR (DMSO-d$_6$+D$_2$O, δ): 1.66–2.05 (2H, m), 2.10–2.35 (2H, m), 2.13 (6H, s), 2.72–3.50 (22H, m), 4.88–5.07 (2H, m), 7.27–7.61 (10H, m), 7.90–8.13 (4H, m)

3) (1R,2′S)- and (1S,2′S)-1-(6-Chloro-2-pyridyl)-2-[(7-ethoxycarbonylmethoxy-1,2,3,4-tetrahydro-2-naphthyl)amino]ethanol oxalate mp: 111°–125° C. (dec.)

IR (Nujol): 3250 (broad), 2800–2300 (broad), 1750, 1640, 790, 700 cm$^{-1}$

NMR (DMSO-d$_6$+D$_2$O, δ): 1.20 (3H, t, J=7.1 Hz), 1.21 (3H, t, J=7.1 Hz), 2.05–2.40 (4H, m), 2.95–3.35 (12H, m), 4.15 (2H, q, J=7.1 Hz), 4.16 (2H, q, J=7.1 Hz), 4.30–4.45 (2H, m), 4.70 (2H, s ), 4.71 (2H, s), 4.85–5.05 (2H, m), 6.65–6.95 (6H, m), 7.35–7.55 (8H, m)

MASS (m/z): 418 (M−1), 388, 278, 249

4) [(1R,6′R) and (1R,6′S) ]- or [(1S,6′R) and (1S,6′S)]-1-(6-Chloro-2-pyridyl-2-[(3-ethoxycarbonylmethoxy-6,7,8,9-tetrahydro-5H-benzocyclohepten-6-yl)amino]ethanol oxalate mp: 60°–66° C.

IR (Nujol): 3150, 2660, 2350, 1730, 1580 cm$^{-1}$

NMR (CDCl$_3$, δ): 1.1–1.2 (6H, m), 1.95 (4H, m), 2.24 (2H, m), 2.5 (4H, m), 2.63 (4H, m), 3.0–3.5 (10H, m), 4.0–4.2 (4H, m), 4.70 (2H, s), 4.71 (2H, s), 4.9 (2H, m), 6.67 (2H, dd, J=8.1 Hz, 2.6 Hz), 6.79 (1H, d, J=2.6 Hz), 6.85 (1H, d, J=2.6 Hz), 7.04 (2H, d, J=8.1 Hz), 7.48 (2H, d, J=7.9 Hz), 7.5–7.6 (2H, m), 7.9–8.0 (2H, m)

MASS (m/z): 421 and 419 (M$^+$(free)+1)

Example 8

A mixture of (1R,6′R)- and (1R,6′S)-2-[N-benzyl-(3-hydroxy-6,7,8,9-tetrahydro-5H-benzocyclohepten-6-yl)amino]-1-(3-chlorophenyl)ethanol (0.20 g), potassium carbonate (98 mg), and N,N-dimethylformamide (2 ml) was stirred at 60° C. for 1 hour. The mixture was allowed to cool to ambient temperature and then cooled in an ice-bath. To the mixture was added n-tetrabutylammonium bromide (7.6 mg) and diethyl bromomalonate (95% purity; 0.12 ml) and stirring was continued for 1.5 hours in an ice-bath. The reaction mixture was diluted with ethyl acetate and the precipitate was filtered off and washed with ethyl acetate. The filtrate and washings were combined, washed twice with water and once with brine, dried over anhydrous sodium sulfate, and concentrated in vacuo. The residue was subjected to column chromatography on silica gel (230–400 mesh; 7:1 n-hexane-ethyl acetate) to give a diastereomeric mixtures of (1R,6′R)- and (1R,6′S)-[N-benzyl-(3-bis(ethoxycarbonyl)methoxy-6,7,8,9-tetrahydro-5H-benzocyclohepten-6-yl)amino]-1-(3-chlorophenyl)ethanol (0.12 g).

IR (Film): 3400, 1740 cm$^{-1}$

NMR (CDCl$_3$, δ): 1.1–1.4 (14H, m), 1.4–2.4 (10H, m), 2.4–3.2 (10H, m), 3.6–4.1 (4H, m), 4.2–4.5 (9H, m), 4.5–4.7 (1H, m), 6.8–7.1 (6H, m), 7.1–7.5 (18H, m)

MASS (m/z): 582 (M+2+H)$^+$, 580 (M+H)$^+$

Example 9

To a solution of (1R,6′R)- and (1R,6′S)-2-[N-benzyl-(3-hydroxy-6,7,8,9-tetrahydro-5H-benzocyclohepten-6-yl)-amino]-1-(3-chlorophenyl)ethanol (0.42 g) in N,N-dimethylformamide (5 ml) was added potassium carbonate (0.15 g). After the mixture was stirred at ambient temperature for 0.5 hour, bromoacetone (0.1 ml) was added, and the mixture was stirred at ambient temperature for 18 hours. The mixture was poured into water and extracted once with ethyl acetate. The extract was washed with water and brine, dried over anhydrous sodium sulfate, and concentrated in vacuo. The residue was purified by column chromatography on silica gel eluting with chloroform-methanol (100:1). The obtained free amine was converted to its hydrochloride in a usual manner. The resulting solid was triturated with diisopropyl ether to give a mixture of (1R,6′R)- and (1R,6′S)-2-[N-benzyl-[3-(2-oxopropoxy)-6,7,8,9-tetrahydro-5H-benzocyclohepten-6yl]amino]-1-(3-chlorophenyl)ethanol hydrochloride.

mp: 66°–75° C.

IR (Nujol): 3200, 2600, 1725 cm$^{-1}$

NMR (DMSO-d$_6$, δ): 0.9–1.3 (2H, m), 1.8–2.25 (10H, m), 2.5–2.9 (6H, m), 2.9–3.65 (10H, m), 4.4–5.55 (10H, m), 6.3–7.95 (26H, m), 9.9–10.3 (2H, m)

MASS (m/z): 478 (M$^+$+1-HCl)

Example 10

The following compounds were obtained according to a similar manner to that of Example 9.

1) (1R,6′R)- and (1R,6′S)-2-[N-Benzyl-[3-(2-oxobutoxy)-6,7,8,9-tetrahydro-5H-benzocyclohepten-6-yl]amino]-1-(3-chlorophenyl)ethanol hydrochloride mp: 81°–88° C.

IR (Nujol): 3200, 2570, 1715, 1600 cm$^{-1}$

NMR (DMSO-d$_6$, δ): 0.8–1.4 (8H, m), 1.65–2.25 (4H, m), 2.25–2.8 (10H, m), 2.9–3.7 (10H, m), 4.4–5.6 (10H, m), 6.2–8.0 (26H, m), 10.0–10.9 (2H, m)

MASS (m/z): 492 (M$^+$-HCl)

2) (1R,6′R)- and (1R,6′S)-2-[N-Benzyl-[3-(3,3-dimethyl-2-oxobutoxy) -6,7,8,9-tetrahydro-5H-benzocyclohepten-6-yl]amino]-1-(3-chlorophenyl)ethanol hydrochloride mp: 93°–101° C.

IR (Nujol): 3180, 2580, 1710, 1600 cm$^{-1}$

NMR (DMSO-d$_6$, δ): 1.0–1.3 (20H, m), 1.9–2.2 (4H, m), 2.4–2.8 (6H, m), 2.8–3.7 (10H, m), 4.4–5.5 (10H, m), 6.3–8.0 (26H, m), 9.9–10.8 (2H, m)

Example 11

To an ice-cooled solution of (1R,6′R)- and (1R,6′S)-2-[[2-bis(ethoxycarbonyl)methoxy-6,7,8,9-tetrahydro-5H-benzocyclohepten-6-yl]amino]-1-(3-chlorophenyl)ethanol (0.63 g) in ethanol (6.3 ml) was added 1N sodium hydroxide (2.6 ml). After stirring at ambient temperature for 5 hours, the reaction mixture was concentrated in vacuo to afford a greenish solid, which was washed with ethanol and dried to give the crude product (0.59 g). The crude product was purified by reverse phase HPLC (C$_{18}$ silica gel, 15% acetonitrile in water),to disodium (2R,6′R)- and (2R,6′S)-6-[2-(3-chlorophenyl)-2-hydroxyethylamino]-6,7,8,9-tetrahydro-5H-benzocyclohepten-2-yloxy]malonate (0.38 g) as a white solid.

IR (Nujol): 3380, 1620 cm$^{-1}$

NMR (D$_2$O, δ): 1.4-2.3 (8H, m), 2.6-3.3 (14H, m), 6.6-6.9 (4H, m), 7.09 (2H, d, J=8 Hz), 7.2-7.6 (8H, m)

Example 12

A mixture of (1R,6′R)-2-[(3-ethoxycarbonylmethoxy-6,7,8,9-tetrahydro-5H-benzocyclohepten-6-yl)amino]-1-(3chlorophenyl)ethanol (0.30 g) and 2-methoxyethylamine (6 ml) was stirred at ambient temperature for 72 hours. After removal of the solvent, the residue was purified by column chromatography on silica gel (gradient elution, ethyl acetate then 50:1 to 25:1 to 5:1 ethyl acetate-ethanol) to give the desired product, which was solidified by the addition of chloroform. The solid was suspended in diisopropyl ether-chloroform (10:1, 11 ml) and the mixture was stirred for 3 hours at ambient temperature. The precipitate was collected by filteration and dried in vacuo to give (1R,6′R)-1-(3-chlorophenyl)-2-[[3-(2-methoxyethyl)aminocarbonylmethoxy-6,7,8,9-tetrahydro-5H-benzocyclohepten-6-yl]amino]ethanol (0.21 g).

mp: 55° C.

[α]$_D^{31}$ = -33.6° (c=0.25 EtOH)

NMR (CDCl$_3$, δ): 1.2-2.2 (5H, m), 2.5-2.9 (7H, m), 3.1-3.4 (4H, m), 3.22 (3H, s), 4.39 (2H, s), 4.5-4.7 (1H, m), 5.39 (1H, d, J=4 Hz), 6.64 (1H, dd, J=2 Hz, 8 Hz), 6.67 (1H, d, J=2 Hz), 6.98 (1H, d, J=8 Hz), 7.2-7.4 (4H, m), 7.9-8.1 (1H, m)

MASS (m/z): 449 (M+2+H)$^+$, 447 (M+H)$^+$

Example 13

A solution of (1R,2′S)-2-[(7-ethoxycarbonylmethoxy-1,2,3,4-tetrahydro-2-naphthyl)amino]-1-(3-chlorophenyl)ethanol (30 mg) and 2-methoxyethylamine (300 mg) in ethanol (0.5 ml) was stirred at ambient temperature for 22 hours and evaporated in vacuo. The residue was partitioned between ethyl acetate and sodium bicarbonate aqueous solution. The organic layer was washed twice with brine, dried over magnesium sulfate, and evaporated in vacuo. The residue was converted to the oxalate in a usual manner. The oxalate was washed with diethyl ether to afford (1R,2′S)-1-(3-chlorophenyl)-2-[[7-(2-methoxyethyl)-aminocarbonylmethoxy-1,2,3,4-tetrahydro-2-naphthyl]amino]ethanol oxalate (20 mg) as a colorless powder.

mp: 120°-124° C.

[α]$_D^{30.4}$ = -69.75° (c=0.205, MeOH)

IR (CHCl$_3$): 3430, 3400, 3250, 2950-2400, 1735, 1650, 1605, 1240 cm$^{-1}$

NMR (DMSO-d$_6$, δ): 1.75 (1H, m), 2.2 (1H, m), 2.65-2.95 (3H, m), 3.05-3.45 (11H, m), 4.42 (2H, s), 4.98 (1H, d, J=9.4 Hz), 5.1 (4H, br), 6.65-6.8 (2H, m), 7.03 (1H, d, J=8.4 Hz), 7.35-7.55 (4H, m), 8.05 (1H, m)

Example 14

To a mixture of (R)-2-amino-1-(3-chlorophenyl)ethanol (172 mg), 3-nitro-6,7,8,9-tetrahydro-5H-benzocyclohepten-6-one (205 mg) and acetic acid (0.27 ml) in methanol (4 ml) was added portionwise sodium cyanoborohydride (94 mg) and the mixture was stirred at ambient temperature for 1.5 hours. The reaction mixture was diluted with water, made alkaline with 28% ammonia solution, and extracted with ethyl acetate. The extract was washed with brine, dried over magnesium sulfate and concentrated in vacuo. The residue was purified by column chromatography on silica gel eluting with chloroform-methanol (50:1). The obtained free amine was converted to its hydrochloride in a usual manner. The resulting solid was triturated with diethyl ether to give a mixture of (1R,6′R)- and (1R,6′S)-2-[(3-nitro-6,7,8,9-tetrahydro-5H-benzocyclohepten-6-yl)amino]-1-(3-chlorophenyl)ethanol hydrochloride (220 mg).

mp: 178°-182° C.

IR (Nujol): 3270, 1518, 1340 cm$^{-1}$

NMR (DMSO-d$_6$, δ): 1.17-1.47 (2H, m), 1.80-2.20 (4H, m), 2.25-2.45 (2H, m), 2.80-3.5 (14H, m), 5.0-5.18 (2H, m), 6.32-6.45 (2H, m), 7.33-7.6 (10H, m), 8.0-8.1 (2H, m), 8.1-8.3 (2H, m), 8.75-9.05 (2H, m), 9.3-9.7 (2H, m)

MASS (m/z): 361 (M$^+$+1-HCl)

Example 15

To a solution of (R)-2-amino-1-(3-chlorophenyl)ethanol (343 mg) and 7-nitro-2-tetralone (354 mg) in methanol (9 ml), sodium cyanoborohydride (189 mg) and acetic acid (0.6 ml) were added at 26°-29° C. and the whole was stirred at ambient temperature overnight. To the solution, conc. hydrochloric acid (1 ml) was added at 0° C. After stirring for 3.5 hours, water (10 ml) and 28% ammonium hydroxide (2 ml) were added. The solution was extracted with ethyl acetate and the extract was washed with brine, dried over potassium carbonate, and evaporated in vacuo. The residue was dissolved in ethyl acetate and 4N hydrogen chloride in ethyl acetate (0.6 ml) was added to the solution. The resulting precipitates were collected by filtration and dried to give (1R,2′R)- and (1R,2′S)-1-(3-chlorophenyl)-2-[(7-nitro-1,2,3,4-tetrahydro-2-naphthyl)amino]ethanol hydrochloride (0.60 g). The obtained powder was recrystallized from a mixture of ethanol (12 ml) and methanol (5 ml) to give (1R,2′R)-or (1R,2′S)-1-(3-chlorophenyl)-2-[(7-nitro-1,2,3,4-tetrahydro-2-naphthyl)amino]ethanol hydrochloride (0.17 g).

mp: 216°-219° C. (dec.)

[α]$_D^{21.2}$ = +18.5° (c=0.35, DMSO)

IR (Nujol): 3325, 2750, 2660 cm$^{-1}$

NMR (DMSO-d$_6$, δ): 1.71-2.03 (1H, m), 2.28-2.52 (1H, m), 2.76-3.69 (7H, m), 5.03-5.21 (1H, m), 6.39 (1H, d, J=3.8 Hz), 7.30-7.60 (5H, m), 7.92-8.13 (2H, m), 9.13 (1H, br s), 9.74 (1H, br s)

The filtrate was evaporated in vacuo and the residue was triturated with isopropanol and diethyl ether to give (1R,2′R) - and (1R,2′S)-1-(3-chlorophenyl)-2-[(7-nitro-1,2,3,4-tetrahydro-2-naphthyl)amino]ethanol hydrochloride (0.32 g).

diastereomer A: NMR (DMSO-d$_6$, δ): 1.72-2.05 (1H, m), 2.30-2.50 (1H, m), 2.78-3.69 (7H, m), 4.80-4.95 (1H, m), 6.24 (1H, d, J=4.3 Hz), 7.30-7.58 (5H, m), 7.94-8.10 (2H, m), 9.11 (1H, br s), 9.74 (1H, br s)

diastereomer B: NMR (DMSO-d$_6$, δ): 1.72-2.05 (1H, m), 2.30-2.50 (1H, m), 2.78-3.69 (7H, m), 5.02-5.21 (1H, m), 6.40 (1H, d, J=3.8 Hz), 7.30-7.58 (5H, m), 7.94-8.10 (2H, m), 9.11 (1H, br s), 9.74 (1H, br s)

diastereomer A: diastereomer B=1:7

Example 16

A solution of (1R,2'R)- and (1R,2'S)-1-(3-chlorophenyl)-2-[(7-nitro-1,2,3,4-tetrahydro-2-naphthyl)amino]ethanol hydrochloride (200 mg) in methanol (5 ml) was made alkaline with 28% ammonium hydroxide solution. The solution was extracted with ethyl acetate and the extract was washed with brine, dried over anhydrous sodium sulfate, and evaporated in vacuo. The residue was dissolved in a mixture of ethyl acetate and methanol and the solution was hydrogenated over 10% palladium on carbon (8.5 mg). After removing the catalyst by filtration, 4N hydrogen chloride in ethyl acetate (0.4 ml) was added to the filtrate. The solution was evaporated in vacuo and the residue was triturated with isopropanol and diethyl ether to give (1R,2'R)- and (1R,2'S)-2-[(7-amino-1,2,3,4-tetrahydro-2-naphthyl)amino]-1-(3-chlorophenyl)ethanol dihydrochloride (191 mg).

mp: 182°–185° C.
IR (Nujol): 2750–2500 cm$^{-1}$
NMR (DMSO-d$_6$, δ): 1.66–2.02 (2H, m), 2.24–2.46 (2H, m), 2.60–3.81 (16H, m), 5.12 (2H, br d, J=7.7 Hz), 6.40 (2H, br m), 7.06–7.60 (14H, m), 9.04 (2H, br s), 9.70 (2H, br s), 10.31 (4H, br s)

Example 17

The following compounds were obtained according to a similar manner to that of Example 14.

1) (1R,6'R)- and (1R,6'S)-2-[(3-Bromo-6,7,8,9-tetrahydro-5H-benzocyclohepten-6-yl)amino]-1-(3-chlorophenyl)ethanol
   mp: 107°–120° C.
   IR (Nujol): 3140, 3060, 1590, 1570 cm$^{-1}$
   NMR (CDCl$_3$ - D$_2$O, δ): 1.40–2.15 (8H, m), 2.48–3.10 (14H, m), 4.50–4.67 (2H, m), 6.95 (2H, d, J=7.8 Hz), 7.14–7.42 (12H, m)

2) Ethyl 3-{(RS)-8-[(R)-2-(3-chlorophenyl)-2-hydroxyethylamino]-6,7,8,9-tetrahydro-5H-benzocyclohepten-2-yl}propionate
   mp: 81°–85° C.
   IR (Nujol): 3300, 3100, 1720 cm$^{-1}$
   NMR (CDCl$_3$, δ): 1.23 (6H, t, J=7.1 Hz), 1.44–2.14 (6H, m), 1.60–2.90 (4H, br m), 2.49–3.10 (22H, m), 4.12 (4H, q, J=7.1 Hz), 4.50–4.66 (2H, m), 6.90–7.44 (14H, m)

Example 18

The following compound was obtained according to a similar manner to that of Example 15.
Ethyl (E)-3-{(RS)-8-[(R)-2-(3-chlorophenyl)-2-hydroxyethylamino]-6,7,8,9-tetrahydro-5H-benzocyclohepten-2-yl}acrylate oxalate (2:1)
mp: 123°–140° C.
IR (Nujol): 3250, 1700 cm$^{-1}$
NMR (DMSO-d$_6$, δ): 1.25 (6H, t, J=7.0 Hz), 1.13–1.44 (2H, m), 1.71–2.40 (6H, m), 2.65–3.36 (14H, m), 4.18 (4H, q, J=7.0 Hz), 4.88–5.07 (2H, m), 5.66–7.40 (10H, br m), 6.56 (2H, d, J=16.0 Hz), 7.12–7.70 (16H, m)

Example 19

A mixture of (1R,6'R)- or (1R,6'S)- or (1S,6'R)- or (1S,6'S)-1-(2-naphthyl)-2-[N-benzyl-13-hydroxy-6,7,8,9-tetrahydro-5H-benzocyclohepten-6-yl)amino]ethanol (isomer A) (1110 mg), 60% sodium hydride in oil (11 mg), ethyl bromoacetate (46 mg) in N,N-dimethylformamide (2 ml) was stirred at ambient temperature. The resulting mixture was diluted with water and extracted with ethyl acetate. The extract was washed with brine, dried, evaporated in vacuo to afford (1R,6'R)- or (1R,6'S)- or (1S,6'R)- or (1S,6'S)-1-(2-naphthyl-2-[N-benzyl-(3-ethoxycarbonylmethoxy-6,7,8,9-tetrahydro-5H-benzocyclohepten-6-yl)amino]ethanol as an oil. (single isomer A)

NMR (CDCl$_3$, δ): 1.29 (3H, t, J=7.1 Hz), 2.0–2.8 (11H, m), 3.74 (1H, d, J=13.7 Hz), 4.00 (1H, d, J=13.7 Hz), 4.27 (2H, q, J=7.1 Hz), 4.59 (2H, s), 4.72 (1H, dd, J=3.6 Hz, 9.9 Hz), 6.58 (1H, dd, J=2.7 Hz, 8.2 Hz), 6.78 (1H, d, J=2.7 Hz), 6.96 (1H, d, J=8.2 Hz), 7.2–7.5 (7H, m), 7.8 (4H, m), 8.01 (1H, s)
MASS (m/z): 524 (M$^+$+1), 506 and 366

Example 20

The following compound was obtained according to a similar manner to that of Example 19.
(1R,6'R)- or (1R,6'S)- or (1S,6'R)- or (1S,6'S)-1-(2-Naphthyl)-2-[N-benzyl-(3-ethoxycarbonylmethoxy-6,7,8,9-tetrahydro-5H-benzocyclohepten-6-yl)amino]ethanol. (single isomer B)

NMR (CDCl$_3$, δ): 1.2 (3H, t, J=7.1 Hz), 1.3–3.1 (12H, m), 3.70 (1H, d, J=13.7 Hz), 3.77 (1H, d, J=13.7 Hz), 4.20 (2H, q, J=7.1 Hz), 4.5 (2H, s), 4.5–4.7 (1H, m), 6.59 (1H, dd, J=2.6 Hz, 8.1 Hz), 6.73 (1H, d, J=2.6 Hz), 6.94 (1H, d, J=8.1 Hz), 7.2–7.5 (7H, m), 7.6–7.8 (4H, m), 8.01 (1H, s)
MASS (m/z): 524 (M$^+$+1), 506 and 366

Example 21

A mixture of 8-benzylamino-6,7,8,9-tetrahydro-5H-benzocyclohepten-2-ol hydrochloride (5.0 g), N,N-diisopropylethylamine (5.7 ml), (R)-3-chlorostyrene oxide (3.8 g), and ethanol (16.4 ml) was refluxed for 40 hours. After cooling, the reaction mixture was concentrated in vacuo. The residue was dissolved in ethyl acetate, washed with water and brine, dried over anhydrous sodium sulfate, and concentrated in vacuo. Purification of the crude product by column chromatography on silica gel (elution; 4:1 n-hexane-ethyl acetate) gave a diastereomeric mixtures of (1R,6'R)- and (1R,6'S)-2-[N-benzyl-(3-hydroxy-6,7,8,9-tetrahydro-5H-benzocyclohepten-6-yl)amino]-1-(3-chlorophenyl)ethanol (6.3 g) as an oil.

IR (Film): 3250 cm$^{-1}$
NMR (CDCl$_3$, δ): 0.8–1.0 (1H, m), 1.1–1.5 (3H, m), 1.5–1.8 (1H, m), 1.8–2.1 (4H, m), 2.1–2.4 (1H, m), 2.4–2.9 (11H, m), 3.07 (1H, dd, J=10 Hz, 13 Hz), 3.75 (2H, q, J=13 Hz), 3.80 (2H, q, J=13 Hz), 4.0–5.2 (2H, br m), 4.35 (1H, dd, J=4 Hz, 10 Hz), 4.46 (1H, dd, J=4 Hz, 10 Hz), 6.52 (2H, dd, J=2 Hz, 8 Hz), 6.61 (1H, d, J=2 Hz), 6.64 (1H, d, J=2 Hz), 6.89 (2H, d, J=8 Hz), 7.0–7.4 (18H, m)
MASS (m/z): 424 (M+2+H)$^+$, 422 (M+H)$^+$

Example 22

A solution of (R)-3-chlorostyrene oxide (48 mg), and 6,7-dihydro-2-nitro-5H-benzocyclohepten-7-amine (84 mg) in ethanol (3 ml) and dioxane (1 ml) was refluxed for 1 hour and evaporated in vacuo. The residue was chromatographed over silica gel using dichloromethane-methanol as an eluent and the obtained oil was converted to oxalate in a usual manner. The oxalate was crystallized from diethyl ether to afford (1R,7'R)- and (1R,7'S)-1-(3-chlorophenyl)-2-[(6,7-dihydro-2-nitro-5H-benzocyclohepten-7-yl)amino]ethanol oxalate (48 mg) as a pale brown powder.

mp: 100°–108° C. (dec.)

IR (Nujol): 3300, 2750–2300, 1710, 1600, 1515, 1350 cm$^{-1}$

NMR (DMSO-d$_6$, δ): 2.1 (2H, m), 2.35 (2H, m), 2.95–3.3 (5H m), 4.15 (2H, m), 4.95 (2H, m), 6.14 (1H, br d, J=12.8 Hz), 6.20 (1H, br d, J=12.8 Hz), 6.86 (2H, d, J=12.8 Hz), 7.25–7.55 (10H, m), 8.06 (2H, dd, J=8.4 Hz, 2.4 Hz), 8.19 (2H, d, J=2.4 Hz), 6.0–9.0 (8H br)

FAB-MASS (m/z): 361 and 359 (M$^+$-C$_2$H$_2$O$_4$+1)

Example 23

A solution of 2,2''-oxybis[2-hydroxy-2'-acetonaphthone] (77.3 mg), (S)-2-amino-7-ethoxycarbonylmethoxy-1,2,3,4-tetrahydronaphthalene hydrochloride (114.3 mg) and triethylamine (0.07 ml) in ethanol (3 ml) was stirred at ambient temperature for 30 minutes and cooled with ice water. Sodium borohydride (45.4 mg) was added to the mixture and the resulting mixture was stirred at ambient temperature for 1 hour. The reaction mixture was diluted with water and extracted with ethyl acetate. The extract was dried over magnesium sulfate and evaporated in vacuo. The obtained oil was converted to hydrochloride in a usual manner to give a colorless powder of (1R,2'S)- and (1S,2'S)-2-[(7-ethoxycarbonylmethoxy-1,2,3,4-tetrahydro-2-naphthyl)amino]-1-(2-naphthyl)ethanol hydrochloride (90.7 mg).

mp: 154°–156° C.

IR (Nujol): 3350, 2800–2300, 1730 cm$^{-1}$

NMR (DMSO-d$_6$, δ): 1.20 (6H, t, J=7.1 Hz), 1.7–2.0 (2H, m), 2.2–3.6 (16H, m), 4.15 (4H, q, J=7.1 Hz), 4.72 (4H, s), 5.2–5.4 (2H, m), 6.3–6.4 (2H, m), 6.6–6.8 (4H, m), 7.02 (2H, d, J=8.3 Hz), 7.5–7.7 (6H, m), 7.8–8.1 (8H, m), 9.03 (2H, br s), 9.6 (2H, br s)

MASS (m/z): 262, 233

Example 24

The following compounds were obtained according to similar manner to that of Example 23.

1) (1R,2'S)- and (1S,2'S)-2-[(7-Ethoxycarbonylmethoxy-1,2,3,4-tetrahydro-2-naphthyl)amino]-1-(1-naphthyl)ethanol hydrochloride mp: 70°–84° C.

IR (Nujol): 3300, 2750–2250, 1750 cm$^{-1}$

NMR (DMSO-d$_6$, δ): 1.20 (6H, t, J=7.1 Hz), 1.6–2.0 (2H, m), 2.2–3.6 (16H, m), 4.15 (4H, q, J=7.1 Hz), 4.70 (2H, s), 4.71 (2H, s), 5.8–6.0 (2H, m), 6.33 (2H, d, J=3.7 Hz), 6.6–6.8 (4H, m), 7.01 (2H, d, J=8.3 Hz), 7.5–7.7 (6H, m), 7.80 (2H, d, J=6.9 Hz), 7.9–8.1 (4H, m), 8.3–8.4 (2H, m), 8.91 (2H, br s), 9.96 (2H, br s)

MASS (m/z): 420 (M$^+$+1), 262, 233

2) (1R,2'S)- and (1S,2'S)-2-[(7-Ethoxycarbonylmethoxy-1,2,3,4-tetrahydro-2-naphthyl)amino]-1-(5-indanyl)ethanol hydrochloride mp: 141°–146° C.

IR (Nujol): 3325, 2750, 2510, 2490, 1740 cm$^{-1}$

NMR (CDCl$_3$, δ): 1.29 (6H, t, J=7.1 Hz), 2.01 (2H, t, J=7.4 Hz), 2.08 (2H, t, J=7.4 Hz), 2.00–2.28 (2H, m), 2.42–2.62 (2H, m), 2.65–3.02 (14H, m), 3.10–3.61 (10H, m), 4.25 (4H, q, J=7.1 Hz), 4.51 (4H, s), 5.44 (2H, br d, J=8.3 Hz), 6.55 (2H, d, J=2.5 Hz), 6.71 (2H, dd, J=2.5 Hz, 8.4 Hz), 6.97 (2H, d, J=8.4 Hz), 7.14–7.26 (4H, m), 7.31 (2H, s), 8.91 (2H, br s), 10.17 (2H, br s)

Example 25

A mixture of (1R,6'R)- and (1R,6'S)-2-[N-benzyl-(3-ethoxycarbonylmethoxy-6,7,8,9-tetrahydro-5H-benzocyclohepten-6-yl]amino-1-(3-chlorophenyl)ethanol (0.34 g), 10% palladium on carbon (50% wet; 68 mg), ammonium formate (0.25 g), and ethanol (17 ml) was refluxed for 20 minutes. The catalyst was filtered off and washed with ethanol. Removal of the solvent in vacuo afforded the residue, which was diluted with ethyl acetate, washed with saturated aqueous sodium bicarbonate and brine, dried over anhydrous sodium sulfate, and concentrated in vacuo. Purification of the crude product by column chromatography on silica gel (elution; 25:1 ethyl acetate-ethanol) gave a diastereomeric mixtures of (1R,6'R)- and (1R,6'S)-2-[(3-ethoxycarbonylmethoxy-6,7,8,9-tetrahydro-5H-benzocyclohepten-6-yl)amino]-1-phenylethanol (0.21 g) as an oil. This oil was dissolved in ethyl acetate (2.1 ml) and treated with 4N hydrogen chloride in ethyl acetate (1.4 ml). After removal of the solvent, the mixture was pulverized with diisopropyl ether-ethyl acetate (3:1, 2.0 ml). The precipitate was collected, washed with diisopropyl ether, and dried in vacuo to give a diastereomeric mixtures of (1R,6'R)- and (1R,6'S)-2-[(3-ethoxycarbonylmethoxy-6,7,8,9-tetrahydro-5H-benzocyclohepten-6-yl)amino]-1-phenylethanol hydrochloride as a white solid. Chiral HPLC analysis revealed that partial epimerization of the hydroxyl group at benzylic position of the product was occurred during the reaction.

mp: 152°–154° C.

IR (Nujol): 3350, 3270, 3160, 2770, 1730 cm$^{-1}$

NMR (DMSO-d$_6$, δ): 1.0–1.4 (2H, m), 1.19 (3H, t, J=7 Hz), 1.20 (3H, t, J=7 Hz), 1.7–2.1 (4H, m), 2.2–2.4 (2H, m), 2.5–2.8 (4H, m), 2.9–3.4 (10H, m), 4.15 (2H, q, J=7 Hz), 4.18 (2H, q, J=7 Hz), 4.70 (2H, s), 4.71 (2H, s), 4.9–5.1 (2H, m), 6.20 (2H, d, J=4 Hz), 6.67 (2H, dd, J=2 Hz, 8 Hz), 6.81 (1H, d, J=2 Hz), 6.87 (1H, d, J=2 Hz), 7.03 (2H, d, J=8 Hz), 7.2–7.5 (10H, m), 8.6–9.0 (2H, br m), 9.1–9.6 (2H, br m)

MASS (m/z): 384 (M+H)$^+$

Example 26

A mixture of (S)-N-benzyl-3-ethoxycarbonylmethoxy-6,7,8,9-tetrahydro-5H-benzocyclohepten-6-amine (35.3 g), (R)-3-chlorostylene oxide (>97% ee; 20.0 g), and ethanol (99 ml) was refluxed for 45 hours. After cooling, the reaction mixture was concentrated in vacuo to give the residue, which was purified by column chromatography on silica gel (SiO$_2$; 230–400 mesh, elution; dichloromethane) to give (1R,6'S)-2-[N-benzyl-(3-ethoxycarbonylmethoxy-6,7,8,9-tetrahydro-5H-benzocyclohepten-6-yl)amino]-1-(3chlorophenyl)ethanol (37.7 g) as a pale yellow oil. This oil was dissolved in ethyl acetate (340 ml) and treated with 4N hydrogen chloride in ethyl acetate (37 ml) in an ice-bath. Then the ice-bath was removed, and the solution was warmed to 40° C. and slowly diluted with pre-warmed (40° C.) diisopropyl ether (300 ml). The resulting suspension was allowed to cool to ambient temperature and stirred for a total of 3.5 hours. The mixture was filtered and the cake was washed with diisopropyl ether-ethyl acetate (4:5, 90 ml). The product was dried in vacuo to give (1R,6'S)-2-[N-benzyl-(3-ethoxycarbonylmethoxy-6,7,8,9-tetrahydro-5H-benzocyclohepten-6-yl)amino]-1-(3-chlorophenyl)ethanol hydrochloride (35.7 g) as a white solid. Chiral HPLC analysis indicated that the product was >99% diastereomerically pure.

$[\alpha]_D^{22} = +29.2°$ (c=0.40, EtOH)

mp: 152°–153° C.

IR (Nujol): 3270, 2670, 2600, 1750 cm$^{-1}$

NMR analysis revealed that the product consisted of two rotamers in dimethyl sulfoxide.

Chemical shifts are shown for the major rotamer.

NMR (DMSO-d$_6$, δ): 1.0–1.4 (1H, m), 1.22 (3H, t, J=7 Hz), 1.9–2.3 (2H, m), 2.3–2.5 (1H, m), 2.5–2.9 (2H, m), 2.9–3.7 (5H m), 4.18 (2H, q, J=7 Hz), 4.4–4.8 (3H, m), 4.73 (2H, s), 6.3–6.4 (1H, m), 6.6–6.8 (1H, m), 6.9–7.0 (1H, m), 7.03 (1H, d, J=8 Hz), 7.2–7.6 (7H, m), 7.8–8.0 (2H, m), 9.8–10.0 (1H, m)

MASS (m/z): 510 (M+2+H)+, 508 (M+H)+

Example 27

The following compounds were obtained according to a similar manner to that of Example 26.

1) (1R,6'R)-2-[N-Benzyl-(3-ethoxycarbonylmethoxy-6,7,8,9-tetrahydro-5H-benzocyclohepten-6-yl)amino]-1-(3-chlorophenyl)ethanol hydrochloride
$[\alpha]_D^{20} = -53.2°$ (c=0.53, EtOH)
mp: >128° C.
IR (Nujol): 3250, 2600, 1760 cm$^{-1}$ NMR analysis revealed that the product consisted of two rotamers in dimethyl sulfoxide.

Chemical shifts are shown for the major rotamer.

NMR (DMSO-d$_6$, δ): 1.0–1.4 (1H, m), 1.21 (3H, t, J=7 Hz), 1.9–2.3 (3H, m), 2.4–2.9 (3H, m), 2.9–4.0 (4H, m), 4.16 (2H, q, J=7 Hz), 4.70 (2H, s), 4.4–5.0 (3H, m), 6.49 (1H, br m), 6.64 (1H, dd, J=2 Hz, 8 Hz), 6.83 (1H, br s), 6.9–7.1 (1H, m), 7.2–7.6 (7H, m), 7.84 (2H, br s), 10.2–10.6 (1H, br m)

MASS (m/z): 510 (M+2+H)+, 508 (M+H)+

2) (1R, 6'R)- and (1R,6'S)-2-[N-Benzyl-(3-pentyloxy-6,7,8,9-tetrahydro-5H-benzocyclohepten-6-yl)amino]-1-(3-chlorophenyl)ethanol hydrochloride
mp: 154°–165° C.
IR (Nujol): 3280, 2600, 1600 cm$^{-1}$ NMR (DMSO-d$_6$, δ): 0.9–1.0 (6H, m), 1.0–1.5 (10H, m), 1.6–1.8 (4H, m), 1.85–2.2 (4H, m), 2.35–2.8 (6H, m), 2.95–3.7 (10H, m), 3.8–4.0 (4H, m), 4.4–5.5 (6H, m), 6.25–7.95 (26H, m), 9.9–10.2 (2H, m)

3) (1R,6'R )- and (1R,6'S)-2-[N-Benzyl-[3-(2-oxopentyloxy)-6,7,8,9-tetrahydro-5H-benzocyclohepten-6-yl]amino]-1-(3-chlorophenyl)ethanol hydrochloride
mp: 79°–85° C.
IR (Nujol): 3200, 2600, 1720, 1610 cm$^{-1}$ NMR (DMSO-d$_6$, δ): 0.87 (6H, t, J=7.3 Hz), 1.0–1.4 (2H, m), 1.4–1.7 (4H, m), 1.8–2.3 (4H, m), 2.3–2.9 (10H, m), 2.9–3.7 (10H, m), 4.4–5.6 (10H, m), 6.2–8.0 (26H, m), 10.1–11.1 (2H, m)

MASS (m/z): 506 (M+ +1-HCl)

4) (1R,6'R)- and (1R,6'S)-2-[N-Benzyl-[3-((RS)-2-oxopentan-3-yloxy)-6,7,8,9-tetrahydro-5H-benzocyclohepten-6-yl]amino]-1-(3-chlorophenyl)ethanol hydrochloride
mp: 104°–109° C.
IR (Nujol): 3200, 2580, 1710, 1600 cm$^{-1}$ NMR (DMSO-d$_6$, δ): 0.9–1.35 (8H, m), 1.6–2.25 (14H, m), 2.35–2.9 (6H, m), 2.9–3.7 (10H, m), 4.3–5.5 (8H, m), 6.3–8.0 (26H, m), 9 8–10.8 (2H, m)

MASS (m/z): 506 (M+ +1-HCl)

5) (1R,6'R)- and (1R,6'S)-2-[N-Benzyl-[2-bis(ethoxycarbonyl)methoxy-6,7,8,9-tetrahydro-5H-benzocyclohepten-6-yl]amino]-1-(3-chlorophenyl)ethanol hydrochloride
mp: >95° C.
IR (Nujol): 3400, 1740 cm$^{-1}$ NMR (DMSO-d$_6$, δ): 1.1–1.4 (2H, m), 1.19 (12H, t, J=7 Hz), 18-2 3 (4H, m), 2.3–2.9 (8H, 2.9–3.8 (8H, m), 4.22 (5H q, J=7 Hz), 4.3–4.8 (6H, m), 5.62 (1H, s), 5.64 (1H, s), 6.3–6.6 (2H, m), 6.7–6.9 (4H, m), 7.1–8.0 (20H, m), 9.7–10.1 (1H, m)

MASS (m/z): 582 (M+2+H)+, 580 (M+H)+

Example 28

The following compounds were obtained according to a similar manner to that of Example 21.

1) (1R,6'R)- and (1R,6'S)-2-[N-Benzyl-(3-ethoxycarbonylmethoxy-6,7,8,9-tetrahydro-5H-benzocyclohepten-6-yl)-amino]-1-(3-chlorophenyl)ethanol
IR (Film): 3400, 3000, 2900, 2830, 1740 cm$^{-1}$ NMR (CDCl$_3$, δ): 1.28 (3H, t, J=7 Hz), 1.30 (3H, t, J=7 Hz), 1.2–1.4 (2H, m), 1.5–3.0 (2H, br m), 1.6–1.8 (1H, m), 1.8–2.9 (18H, m), 3.09 (1H, dd, J=10 Hz, 13 Hz), 3.77 (2H, q, J=13 Hz), 3.82 (2H, q, J=13 Hz), 4.26 (2H, q, J=7 Hz), 4.28 (2H, q, J=7 Hz), 4.30 (1H, dd, J=3 Hz, 10 Hz), 4.48 (1H, dd, J=3 Hz, 10 Hz), 4.57 (2H, s), 4.59 (2H, s), 6.5–6.7 (2H, m), 6.73 (1H, d, J=2 Hz), 6.78 (1H, d, J=2 Hz), 6.95 (2H, d, J=8 Hz), 7.1–7.4 (18H, m)

MASS (m/z): 510 (M+2+H)+, 508 (M+H)+

2) (1R,6'R)- and (1R,6'S)-2-[N-Benzyl-[3-((RS)-1-ethoxycarbonyl)ethoxy-6,7,8,9-tetrahydro-5H-benzocyclohepten-2-yl]amino]-1-(3-chlorophenyl)ethanol
mp: 90°–99° C.
IR (Film): 3300, 2580, 1730 cm$^{-1}$ NMR (DMSO-d$_6$, δ): 1.0–1.4 (5H m), 1.4–1.6 (6H, m), 1.8–2.2 (4H, m), 2.4–2.9 (6H, m), 2.9–3.7 (10H, m), 4.0–4.3 (4H, m), 4.4–5.6 (5H, m), 6.3–8.0 (26H, m), 10–11.2 (2H, m)

Example 29

1) A mixture of (1R,6'R)- and (1R,6'S)-2-[N-benzyl-[3-(2-oxopropoxy)-6,7,8,9-tetrahydro-5H-benzocyclohepten-6yl]amino]-1-(3-chlorophenyl)ethanol hydrochloride (290 mg) was catalytically hydrogenated at ambient temperature in a mixture of ethanol (3 ml) and chlorobenzene (3 ml) using 10% palladium on carbon (50% wet, 20 mg). After removal of the catalyst, the solvent was removed by evaporation. To the residue, ethyl acetate and water were added and the organic layer was separated, washed with an aqueous solution of sodium hydrogen carbonate and concentrated in vacuo. The residue was purified by column chromatography on silica gel eluting with chloroform-methanol (50:1). The fractions containing object compound were collected and concentrated in vacuo to give (1R,6'R)- and (1R,6'S)-2-[[3-(2-oxopropoxy)-6,7,8,9-tetrahydro-5H-benzocyclohepten-6-yl]amino]-1-(3-chlorophenyl)ethanol.

2) The obtained free amine was converted to its hydrochloride in a usual manner. The resulting solid was triturated with diethyl ether to give a mixture of (1R,6'R)- and (1R,6'S)-2-[[3-(2-oxopropoxy)-6,7,8,9-tetrahydro-5H-benzocyclohepten-6-yl]amino]-1-(3-chlorophenyl)ethanol hydrochloride.
mp: 155°–161° C.
IR (Nujol): 1720, 1575 cm$^{-1}$ NMR (DMSO-d$_6$, δ): 1.1–1.35 (2H, m), 1.75–2.1 (4H, m), 2.1 4 (6H, s), 2.2–2.4 (2H, m), 2.6–2.8 (4H, m), 2.9–3.3 (10H, m), 4.73 (2H, s), 4.75 (2H, s), 4.9 5–5.1 (2H, m), 6.3–6.4 (2H, m), 6.6–6.7 (2H, m), 6.75–6.9 (2H, m), 6.95–7.1 (2H, m), 7.3–7.5 5 (5H m), 8.7–8.9 (2H, m), 9.05–9.35 (2H, m)

MASS (m/z): 388 (M+1-HCl)+

Example 30

The following compounds were obtained according to a similar manner to that of Example 29-1).

1) (1R,6'R)- and (1R,6'S)-2-[[3-(3,3-Dimethyl-2-oxobutoxy)-6,7,8,9-tetrahydro-5H-benzocyclohepten-6yl]amino]-1-(3-chlorophenyl)ethanol mp: 100°–103° C.
IR (Nujol): 1715, 1600 cm$^{-1}$
NMR (CDCl$_3$, δ): 1.24 (18H, s), 1.4–3.1 (22H, m), 4.5–4.65 (2H, m), 4.84 (4H, s), 6.55–6.75 (4H, m), 6.95–7.05 (2H, m), 7.15–7.4 (8H, m)
MASS (m/z): 430 (M+1)$^+$ 2) (1R,6'R)- and (1R,6'S)-2-[(3-Pentyloxy-6,7,8,9-tetrahydro-5H-benzocyclohepten-6-yl)amino]-1-(3-chlorophenyl)ethanol
mp: 102°–106° C.
IR (Nujol): 1605, 1570, 1285 cm$^{-1}$
NMR (CDCl$_3$, δ): 0.92 (6H, t, J=7.0 Hz), 1.3–2.1 (22H, m), 2.5–3.1 (14H, m), 3.92 (4H, t, J=6.8 Hz), 4.5–4.6 (2H, m), 6.6–6.75 (4H, m), 6.95–7.05 (2H, m), 7.15–7.40 (8H, m)

3) (1R,6'R )- and (1R,6'S)-2- [[3-(2-Oxopentyloxy)-6,7,8,9-tetrahydro-5H-benzocyclohepten-6-yl]amino]-1-(3-chlorophenyl)ethanol
mp: 94°–95° C.
IR (Nujol): 3320, 3260, 1720 cm$^{-1}$
NMR (CDCl$_3$, δ): 0.94 (6H, t, J=7.4 Hz), 1.4–2.1 (12H, m), 2.5–3.1 (18H, m), 4.51 (4H, s), 4.45–4.65 (2H, m), 6.55–6.75 (4H, m), 6.9–7.05 (2H, m), 7.15–7.4 (8H m)

4) (1R,6'R )- and (1R,6'S)-2-[[3-((RS)-1-Ethoxycarbonyl)ethoxy-6,7,8,9-tetrahydro-5H-benzocyclohepten-2-yl]amino]-1-(3-chlorophenyl)ethanol
mp: 97°–101° C.
IR (Nujol): 1742, 1605 cm$^{-1}$
NMR (CDCl$_3$, δ): 1.24 (6H, t, J=7.1 Hz), 1.60 (6H, d, J=6.8 Hz), 1.50–2.10 (10H, m), 2.45–3.1 (14H, m), 4.10–4.30 (4H, m), 4.50–4.65 (2H, m), 4.70 (2H, q, J=6.8 Hz), 6. 50–6.65 (2H, m), 6.65–6.75 (2H, m), 6.90–7.00 (2H, m), 7.15–7.40 (8H, m)

5) (1R,6'R)- and (1R,6'S)-2-[(3-Ethoxycarbonylmethylamino-6,7,8,9-tetrahydro-5H-benzocyclohepten-6-yl)amino]-1-(3-chlorophenyl)ethanol
IR (CHCl$_3$): 3420, 1735, 1615, 1580 cm$^{-1}$
NMR (CDCl$_3$, δ): 1.28 (6H, t, J=7.1 Hz), 1.34–2.20 (8H m), 2.54–3.16 (16H, m), 3.86 (4H, s), 4.22 (4H, q, J=7.1 Hz), 4.-31 (4H, br s), 4.72–4.89 (2H, m), 6.28–6.54 (4H, m), 6.89 (2H, d, J=8.0 Hz), 7.26–7.46 (8H m)
MASS (m/z): 417 (M$^+$), 275, 246

6) (1R,6'R)- or (1R,6'S)- or (1S,6'R)- or (1S,6'S)-1-(2-Naphthyl)-2-[(3-ethoxycarbonylmethoxy-6,7,8,9-tetrahydro-5H-benzocyclohepten-6-yl)amino]ethanol (single isomer B )
mp: 97°–99° C.
[α]$_D$= −26.42° (c=0.28, CH$_2$Cl$_2$)
IR (Nujol): 3200, 1778 cm$^{-1}$
NMR (CDCl$_3$, δ): 1.25 (3H, t, J=7.1 Hz), 1.48 (1H, br), 1.84 (2H, m), 2.11 (1H, m), 2.6–3.0 (7H, m), 3.17 (1H, dd, J=8.8 Hz, 3.2 Hz), 4.22 (2H, q, J=7.1 Hz), 4.55 (2H, s), 5.05 (1H, m), 6.62 (1H, dd, J=2.5 Hz, 8.1 Hz), 6.76 (1H, d, J=2.5 Hz), 6.96 (1H, d, J=8.1 Hz), 7.4–7.5 (3H, m), 7.8–7.8 (4H, m)
MASS (m/z): 434 (M$^+$+1) and 416

7) (1R,6'R)- and (1R,6'S)-2-[(3-Hydroxy-6,7,8,9-tetrahydro-5H-benzocyclohepten-6-yl)amino]-1-(3-chlorophenyl)ethanol
mp: 180°–181° C.
IR (Nujol): 3150, 2620 cm$^{-1}$
NMR (DMSO-d$_6$, δ): 1.2–2.0 (10H, .m), 2.4–2.9 (14H, m), 4.5–4.7 (2H, m), 5.39 (2H, br s), 6.43 (2H, dd, J=2 Hz, 8 Hz), 6.5–6.6 (2H, m), 6.83 (2H, d, J=8 Hz), 7.2–7.5 (5H m), 8.99 (2H, br s)
MASS (m/z): 334 (M+2+H)$^+$, 332 (M+H)$^+$ 8) (1R,6'R)- and (1R,6'S)-2-[[2-Bis(ethoxycarbonyl)methoxy-6,7,8,9-tetrahydro-5H-benzocyclohepten-6-yl]amino]-1-(3-chlorophenyl)ethanol
mp: 95° C.
IR (Nujol): 1700, 1740 cm$^{-1}$
NMR (CDCl$_3$, δ): 1.30 (12H, t, J=7 Hz), 1.4–1.7 (2H, m), 1.7–2.0 (4H, m), 2.0–2.3 (2H, m), 2.6–3.8 (18H, m), 4.31 (5H q, J=7 Hz), 4.7–4.9 (2H, m), 5.15 (2H, s), 6.65 (2H, dd, J=2 Hz, 8 Hz), 6.75 (2H, d, J=2 Hz), 7.06 (2H, d, J=8 Hz), 7.2–7.3 (6H, m), 7.37 (2H, br s)
MASS (m/z): 492 (M+2+H)$^+$, 490 (M+H)$^+$ 9) (1R,6'R)-2-[(3-Ethoxycarbonylmethoxy-6,7,8,9-tetrahydro-5H-benzocyclohepten-6-yl)amino]-1-(3-chlorophenyl)ethanol
mp: 98°–100° C.
[α]$_D^{29}$= −38.3° (c=0.62, EtOH)
IR (Nujol): 3500–2500, 1760, 1720 cm$^{-1}$
NMR (DMSO-d$_6$, δ): 1.18 (3H, t, J=7 Hz), 1.2–2.1 (6H, m), 2.4–2.9 (6H, m), 4.14 (2H, q, J=7 Hz), 4.5–4.6 (1H, m), 4.68 (2H, s), 5.40 (1H, d, J=4 Hz), 6.58 (1H, dd, J=2 Hz, 8 Hz), 6.72 (1H, d, J=2 Hz), 6.96 (1H, d, J=8 Hz), 7.2–7.5 (4H, m)
MASS (m/z): 420 (M+2+H)$^+$, 418 (M+H)$^+$ 10) (1R,6'R)- and (1R,6'S) -2- [[3-(2-Ethoxycarbonylpropan-2-yloxy)-6,7,8,9-tetrahydro-5H-benzocyclohepten-6-yl]amino]-1-(3-chlorophenyl)ethanol
mp: 101°–115° C.
IR (Nujol): 1735, 1600 cm$^{-1}$
NMR (CDCl$_3$, δ): 1.24 (6H, t, J=7.1 Hz), 1.57 (12H, s), 1.40–2.05 (5H m), 2.45–3.10 (14H, m), 4.21 (4H, q, J=7.1 Hz), 4.12 (2H, q, J=7.1 Hz), 4.50–4.60 (2H, m), 6.50–6.65 (2H, m), 6.65–6.70 (2H, m), 6.85–7.00 (2H, m), 7.15–7.40 (8H m)

Example 31

The following compounds were obtained according to a similar manner to that of Example 29.

1) (1R,6'S)-2-[(3-Ethoxycarbonylmethoxy-6,7,8,9-tetrahydro-5H-benzocyclohepten-6-yl)amino]-1-(3chlorophenyl)ethanol hydrochloride
mp: 103° C.
[α]$_D^{22}$= +11.5° (c=0.32, EtOH)
IR (Nujol): 3380, 2400, 1760 cm$^{-1}$
(DMSO-d$_6$, δ): 1.1–1.4 (1H, m), 1.19 (3H, t, J=7 Hz), 1.7–2.1 (2H, m), 2.2–2.4 (1H, m), 2.6–2.8 (2H, m), 2.9–3.3 (5H, m), 4.15 (2H, q, J=7 Hz), 4.70 (2H, s), 5.0–5.2 (1H, br m), 6.34 (1H, br d, J=4 Hz), 6.67 (1H, dd, J=2 Hz, 8 Hz), 6.88 (1H, d, J=2 Hz), 7.03 (1H, d, J=8 Hz), 7.3–7.6 (4H, m), 8.6–9.4 (2H, br m)
MASS (m/z): 420 (M+2+H)$^+$, 418 (M+H)$^+$ 2) (1R,6'R)- and (1R,6'S)-2-[[3-(2-Oxobutoxy)-6,7,8,9-tetrahydro-5H-benzocyclohepten-6-yl]amino]-1-(3-chlorophenyl)ethanol hydrochloride
mp: 119°–121° C.
IR (Nujol): 3400.3190, 1715 cm$^{-1}$
NMR (DMSO-d$_6$, δ): 0.95 (3H, t, J=7.3 Hz), 0.96 (3H, t, J=7.3 Hz), 1.1–1.35 (2H, m), 1.75–2.1 (4H, m), 2.2–2.4 (2H, m), 2.5–2.8 (5H m), 2.95–3.3 (10H, m), 4.74 (2H, s), 4.75 (2H, s), 4.95–5.1 (2H, m), 6.3–6.4 (2H, m), 6.6–6.7 (2H, m), 6.75–6.9 (2H, m), 6.95–7.1 (2H, m), 7.3–7.55 (8H, m), 8.7–8.95 (2H, m), 9.1–9.4 (2H, m)
MASS (m/z): 402 (M+1-HCl)$^+$ Example 32

The following compounds were obtained by reacting the compounds, which were prepared according to a similar manner to that of Example 29-1), with oxalic acid.

1) (1R,6'R)- and (1R,6'S)-2-[[3-Bis(ethoxycarbonyl)methoxy-6,7,8,9-tetrahydro-5H-benzocyclohepten-6-yl]amino]-1-(3-chlorophenyl)ethanol oxalate NMR (DMSO-d$_6$+D$_2$O, δ): 1.1–1.4 (14H, m), 1.7–2.1 (4H, m), 2.1–2.4 (2H, m), 2.6–2.8 (4H, m), 2.9–3.4 (10H, m), 4.0–4.4 (8H, m), 4.8–5.0 (2H, m), 5.57 (2H, s), 6.6–7.2 (6H, m), 7.3–7.6 (8H m)

MASS (m/z): 492 (M+2+H)$^+$, 490 (M+H)$^+$ 2) (1R,6′R)- and (1R,6′S)-2-[[3-((RS)-2-Oxopentan-3-yloxy)-6,7,8,9-tetrahydro-5H-benzocyclohepten-6-yl]amino]-1-(3-chlorophenyl)ethanol oxalate
mp: 70°–79° C.

IR (Nujol): 1710 cm$^{-1}$

NMR (DMSO-d$_6$, δ): 0.75–1.0 (8H, m), 1.15–1.4 (2H, m), 1.7–2.05 (6H, m), 2.13 (6H, s ), 2.15–2.35 (2H, m), 2.4–3.35 (14H, m), 4.5–4.65 (2H, m), 4.85–5.0 (2H, m), 6.5–7.1 (6H, m), 7.3–7.6 (8H, m)

MASS (m/z): 416 (M+1-C$_2$H$_2$O$_4$)$^+$ 3) (1R,6′R)- or (1R,6′S)- or (1S,6′R)- or (1S,6′S)-1-(2-Naphthyl)-2-[(3-ethoxycarbonylmethoxy-6,7,8,9-tetrahydro- 5H-benzocyclohepten-6-yl)amino]ethanol oxalate (single isomer A)
mp 90°–99° C.

IR (KBr): 3183, 2856, 1751, 1207 cm$^{-1}$

NMR (CDCl$_3$, δ): 1.25 (3H, t, J=7.1 Hz), 1.5–3.4 (12H, m), 4.2 (2H, q, J=7.1 Hz), 4.46 (2H, s), 4.86 (1H, br), 6.5–6.9 (3H, m), 7.2–7.4 (3H, m), 7.6–7.8 (4H, m)

MASS (m/z): 434 (M$^+$+1) and 416

We claim:

1. A compound of the formula:

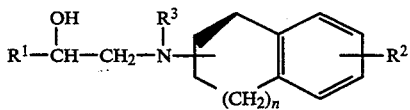

[I]

wherein

R$^1$ is aryl or a heterocyclic group, each of which may be substituted with halogen, hydroxy, protected hydroxy, aryloxy, lower alkoxy, halo(lowr)alkoxy, nitro, cyano, amino or acylamino, R$^2$ is hydrogen, halogen, nitro, hydroxy, lower alkyl optionally substituted with acyl, lower alkenyl optionally substituted with acyl, lower alkoxy optionally substituted with acyl, or amino optionally substituted with acyl(lower)alkyl, R$^3$ is hydrogen, an N-protective group, or lower alkyl optionally substituted with lower alkylthio, n is an integer of 0 to 3, and a heavy solid line means a single bond or a double bond, provided that when n is 1, then 1) R$^1$ is a condensed aromatic hydrocarbon group or a heterocyclic group, each of which may be substituted with halogen, hydroxy, protected hydroxy, aryloxy, lower alkoxy, halo(lowr)alkoxy, nitro, cyano, amino or acylamino, or 2) R$^2$ is halogen, nitro, lower alkyl optionally substituted with acyl, lower alkenyl optionally substituted with acyl, or amino optionally substituted with acyl(lower)alkyl, or 3) R$^3$ is an N-protective group or lower alkyl optionally substituted with lower alkylthio, or 4) a heavy solid line means a double bond, and pharmaceutically acceptable salts thereof.

2. A compound according to claim 1, wherein
R$^1$ is phenyl optionally substituted with halogen,
R$^2$ is lower alkoxy substituted with carboxy or esterified carboxy,
R$^3$ is hydrogen,
n is 0, 2 or 3, and
a heavy solid line means a single bond.

3. A compound according to claim 2, wherein
R$^1$ is phenyl substituted with halogen, and
R$^2$ is methoxy substituted with lower alkoxycarbonyl.

4. A compound according to claim 3, wherein
R$^1$ is phenyl substituted with chlorine,
R$^2$ is methoxy substituted with ethoxycarbonyl, and
n is 2.

5. A compound of claim 4, which is (1R,6′S)-2-[(3-ethoxycarbonylmethoxy-6,7,8,9-tetrahydro-5H-benzocyclohepten-6-yl)amino]-1-(3-chlorophenyl)ethanol or its hydrochloride.

6. A pharmaceutical composition comprising a compound of claim 1, as an active ingredient, in association with a pharmaceutically acceptable, substantially non-toxic carrier or excipient.

7. A method for therapeutic treatment and/or prevention of dysuria, spasm or hyperanakinesia which comprises administering the effective amount of a compound of claim 1 to human beings or animals.

* * * * *